US012746277B2

(12) United States Patent
Webber et al.

(10) Patent No.: US 12,746,277 B2
(45) Date of Patent: Sep. 29, 2026

(54) DYNAMIC-COVALENT HYDROGELS WITH GLUCOSE-SPECIFIC AND GLUCOSE-RESPONSIVE DIBORONATE CROSSLINKING

(71) Applicant: UNIVERSITY OF NOTRE DAME DU LAC, South Bend, IN (US)

(72) Inventors: Matthew Webber, South Bend, IN (US); Yuanhui Xiang, South Bend, IN (US); Sijie Xian, South Bend, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 223 days.

(21) Appl. No.: 18/729,853

(22) PCT Filed: Feb. 8, 2023

(86) PCT No.: PCT/US2023/012572
§ 371 (c)(1),
(2) Date: Jul. 17, 2024

(87) PCT Pub. No.: WO2023/154303
PCT Pub. Date: Aug. 17, 2023

(65) Prior Publication Data

US 2025/0114436 A1 Apr. 10, 2025

Related U.S. Application Data

(60) Provisional application No. 63/267,762, filed on Feb. 9, 2022.

(51) Int. Cl.

| | |
|---|---|
| ***A61K 38/28*** | (2006.01) |
| ***A61K 47/24*** | (2006.01) |
| ***A61K 47/59*** | (2017.01) |
| ***A61K 47/61*** | (2017.01) |
| ***A61K 47/69*** | (2017.01) |
| ***A61P 3/10*** | (2006.01) |

(52) U.S. Cl.
CPC .............. *A61K 38/28* (2013.01); *A61K 47/24* (2013.01); *A61K 47/595* (2017.08); *A61K 47/61* (2017.08); *A61K 47/6903* (2017.08); *A61P 3/10* (2018.01)

(58) Field of Classification Search
CPC .. A61K 47/61; A61K 47/6903; A61K 47/595; A61K 47/24; A61K 38/28; A61P 3/10
See application file for complete search history.

(56) References Cited

U.S. PATENT DOCUMENTS

| | | | |
|---|---|---|---|
| 6,756,360 | B1 | 6/2004 | Erion et al. |
| 6,927,246 | B2 | 8/2005 | Noronha et al. |
| 7,427,415 | B2 | 9/2008 | Scharp et al. |
| 7,442,515 | B2 | 10/2008 | Ratner et al. |
| 7,521,181 | B2 | 4/2009 | Yamada et al. |
| 7,544,695 | B2 | 6/2009 | Berk et al. |
| 7,790,140 | B2 | 9/2010 | Bolotin |
| 7,828,728 | B2 | 11/2010 | Boock et al. |
| 7,858,560 | B2 | 12/2010 | Köster et al. |
| 8,003,597 | B2 | 8/2011 | Chu et al. |
| 8,060,174 | B2 | 11/2011 | Simpson et al. |
| 8,088,928 | B2 | 1/2012 | Nunes et al. |
| 8,101,626 | B2 | 1/2012 | Chu et al. |
| 8,476,308 | B2 | 7/2013 | Shi et al. |
| 8,557,766 | B2 | 10/2013 | Ohkouchi |
| 8,598,374 | B2 | 12/2013 | Shi et al. |
| 8,623,345 | B2 | 1/2014 | Zion et al. |
| 8,929,968 | B2 | 1/2015 | Brister et al. |
| 9,068,013 | B2 | 6/2015 | Lancaster et al. |
| 9,114,177 | B2 | 8/2015 | Kataoka et al. |
| 9,309,550 | B2 | 4/2016 | Cooper et al. |
| 9,486,506 | B2 | 11/2016 | Lau et al. |
| 9,604,964 | B2 | 3/2017 | Ellsworth et al. |
| 9,714,231 | B2 | 7/2017 | Ellsworth et al. |
| 9,732,101 | B2 | 8/2017 | Raines et al. |
| 9,867,869 | B2 | 1/2018 | Anderson et al. |
| 9,986,942 | B2 | 6/2018 | Brauker et al. |
| 9,994,615 | B2 | 6/2018 | Langer et al. |
| 9,999,369 | B2 | 6/2018 | Ziaie et al. |
| 10,072,011 | B2 | 9/2018 | Ellis et al. |
| 10,197,498 | B2 | 2/2019 | Ruckh et al. |
| 10,584,156 | B2 | 3/2020 | Weiss |
| 10,683,379 | B2 * | 6/2020 | Anderson ............. C08F 120/56 |
| 10,759,777 | B2 | 9/2020 | Bersot et al. |
| 10,822,383 | B2 | 11/2020 | Cheng et al. |
| 10,877,035 | B2 | 12/2020 | Birnbaum et al. |

(Continued)

FOREIGN PATENT DOCUMENTS

| | | |
|---|---|---|
| AU | 2006201410 A1 | 4/2006 |
| AU | 2006249219 B2 | 3/2011 |

(Continued)

OTHER PUBLICATIONS

European Patent Office. Extended European Search Report for Application No. 23753385, dated May 15, 2025 (8 pages).
Hoffman, A. S. "Hydrogels for biomedical applications." Advanced drug delivery reviews 64 (2012): 18-23.
Horgan, A. M., et al. "Crosslinking of phenylboronic acid receptors as a means of glucose selective holographic detection." Biosensors and Bioelectronics 21.9 (2006): 1838-1845.
Hyman, A. A. et al. Liquid-Liquid Phase Separation in Biology. Annu. Rev. Cell Dev. Biol. 2014, 30, 39-58.
Ilavsky, J. et al. "Irena: tool suite for modeling and analysis of small-angle scattering." Journal of Applied Crystallography 42.2 (2009): 347-353.

(Continued)

*Primary Examiner* — Michael B. Pallay
(74) *Attorney, Agent, or Firm* — Michael Best & Friedrich LLP

(57) ABSTRACT

Described herein are di-phenylboronic acid (DiPBA) motifs that bind glucose with high affinity and improved specificity. The compounds can be used to prepare dynamic injectable materials with improved encapsulation and glucose-triggered release of insulin in vitro and in vivo.

21 Claims, 49 Drawing Sheets

(56) References Cited

U.S. PATENT DOCUMENTS

| | | | |
|---|---|---|---|
| 11,016,079 B2 | 5/2021 | Slouka et al. | |
| 11,052,133 B2 | 7/2021 | Mahdavi | |
| 11,147,483 B2 | 10/2021 | Boock et al. | |
| 11,179,475 B2 | 11/2021 | Hedrick et al. | |
| 11,191,841 B2 | 12/2021 | Webber et al. | |
| 11,351,230 B2 | 6/2022 | Gu et al. | |
| 11,484,493 B2 | 11/2022 | Friedman | |
| 11,697,007 B2 | 7/2023 | Gu et al. | |
| 11,730,407 B2 | 8/2023 | Boock et al. | |
| 11,752,098 B2 | 9/2023 | Gu et al. | |
| 11,813,352 B2 | 11/2023 | Gu et al. | |
| 2005/0042771 A1 | 2/2005 | Koster et al. | |
| 2005/0181009 A1 | 8/2005 | Hunter et al. | |
| 2005/0181977 A1 | 8/2005 | Hunter et al. | |
| 2005/0187140 A1 | 8/2005 | Hunter et al. | |
| 2005/0260259 A1 | 11/2005 | Bolotin | |
| 2006/0100218 A1 | 5/2006 | Ibrahim et al. | |
| 2007/0037809 A1 | 2/2007 | Nunes et al. | |
| 2007/0037827 A1 | 2/2007 | Nunes et al. | |
| 2007/0043050 A1 | 2/2007 | Nunes et al. | |
| 2007/0110728 A1 | 5/2007 | Austen et al. | |
| 2007/0149466 A1 | 6/2007 | Milburn et al. | |
| 2008/0200434 A1 | 8/2008 | Daniloff | |
| 2009/0197836 A1 | 8/2009 | Van Poelje et al. | |
| 2012/0053222 A1 | 3/2012 | Gorrell et al. | |
| 2012/0177576 A1 | 7/2012 | Hu | |
| 2012/0252780 A1 | 10/2012 | Ng et al. | |
| 2012/0322145 A1 | 12/2012 | Onofiok et al. | |
| 2013/0022592 A1 | 1/2013 | Vaughn et al. | |
| 2013/0245402 A1 | 9/2013 | Ziaie et al. | |
| 2014/0121159 A1 | 5/2014 | Zion et al. | |
| 2014/0213963 A1 | 7/2014 | Wu et al. | |
| 2015/0025005 A1 | 1/2015 | Langer et al. | |
| 2015/0320837 A1 | 11/2015 | Anderson et al. | |
| 2016/0002251 A1 | 1/2016 | Ohtake et al. | |
| 2016/0106676 A1 | 4/2016 | Hoare et al. | |
| 2016/0280827 A1 | 9/2016 | Anderson et al. | |
| 2017/0016885 A1* | 1/2017 | Chen-Izu | G01N 33/543 |
| 2017/0316487 A1 | 11/2017 | Mazed | |
| 2018/0044338 A1 | 2/2018 | Blum et al. | |
| 2018/0369276 A1 | 12/2018 | Lee et al. | |
| 2020/0009069 A1 | 1/2020 | Luo et al. | |
| 2020/0069809 A1 | 3/2020 | Shi et al. | |
| 2020/0360269 A1 | 11/2020 | Gu et al. | |
| 2021/0214412 A1 | 7/2021 | Chou | |
| 2021/0244658 A1 | 8/2021 | Gu et al. | |
| 2021/0267573 A1 | 9/2021 | Reiche et al. | |
| 2021/0369787 A1 | 12/2021 | Gu et al. | |
| 2021/0393543 A1 | 12/2021 | Wu et al. | |
| 2022/0003676 A1 | 1/2022 | Mazed | |
| 2022/0068452 A1 | 3/2022 | Simpson et al. | |
| 2022/0068453 A1 | 3/2022 | Simpson | |
| 2022/0142919 A1 | 5/2022 | Marco-Dufort et al. | |
| 2022/0144915 A1 | 5/2022 | Weiss et al. | |
| 2022/0160841 A1 | 5/2022 | Gu et al. | |
| 2022/0233646 A1 | 7/2022 | Carey | |
| 2022/0362238 A1 | 11/2022 | Gedulin et al. | |
| 2022/0384007 A1 | 12/2022 | Simpson et al. | |
| 2023/0045277 A1 | 2/2023 | Bourque et al. | |
| 2023/0212216 A1 | 7/2023 | Morris et al. | |
| 2023/0240981 A1 | 8/2023 | Gu et al. | |
| 2023/0265111 A1 | 8/2023 | Elliott et al. | |
| 2023/0357349 A1 | 11/2023 | Webber et al. | |
| 2023/0399373 A1 | 12/2023 | Weiss et al. | |

FOREIGN PATENT DOCUMENTS

| | | | |
|---|---|---|---|
| AU | 2015200071 | A1 | 2/2015 |
| CA | 2750115 | A1 | 8/2010 |
| CA | 2750223 | A1 | 8/2010 |
| CN | 101257897 | A | 9/2008 |
| CN | 101282974 | A | 10/2008 |
| CN | 105078890 | B | 7/2018 |
| CN | 109675185 | A | 4/2019 |
| CN | 110452390 | B | 4/2021 |
| CN | 113197838 | A | 8/2021 |
| CN | 113603826 | A | 11/2021 |
| EP | 1143955 | B1 | 7/2005 |
| EP | 1357115 | B1 | 6/2009 |
| EP | 2511844 | B1 | 8/2015 |
| EP | 3586876 | A1 | 1/2020 |
| IN | 2006KO01021 | A | 4/2009 |
| TR | 200202502 | A2 | 6/2004 |
| WO | 2002003978 | A2 | 1/2002 |
| WO | 2004064972 | A2 | 8/2004 |
| WO | 2005108368 | A1 | 11/2005 |
| WO | 2005117608 | A1 | 12/2005 |
| WO | 2006055008 | A2 | 5/2006 |
| WO | 2007008548 | A2 | 1/2007 |
| WO | 2007033353 | A2 | 3/2007 |
| WO | 2008100376 | A2 | 8/2008 |
| WO | 2009023718 | A2 | 8/2008 |
| WO | 2008156866 | A1 | 12/2008 |
| WO | 2009132153 | A2 | 10/2009 |
| WO | 2010088294 | A1 | 8/2010 |
| WO | 2010101949 | A1 | 9/2010 |
| WO | 2010148346 | A2 | 12/2010 |
| WO | 2011059839 | A1 | 5/2011 |
| WO | 2011159297 | A1 | 12/2011 |
| WO | 2012119046 | A2 | 9/2012 |
| WO | 2012174478 | A2 | 12/2012 |
| WO | 2014179344 | A1 | 11/2014 |
| WO | 2015157182 | A1 | 10/2015 |
| WO | 2016079711 | A1 | 5/2016 |
| WO | 2016081692 | A2 | 5/2016 |
| WO | 2016149222 | A2 | 9/2016 |
| WO | 2016172320 | A1 | 10/2016 |
| WO | 2017210168 | A1 | 12/2017 |
| WO | 2018024793 | A1 | 2/2018 |
| WO | 2019057920 | A1 | 3/2019 |
| WO | 2021022116 | A1 | 2/2021 |
| WO | 2021123229 | A1 | 6/2021 |
| WO | 2021202802 | A1 | 10/2021 |
| WO | 2022066938 | A1 | 3/2022 |
| WO | 2022109078 | A1 | 5/2022 |
| WO | 2022119868 | A2 | 6/2022 |
| WO | 2023285357 | A1 | 1/2023 |
| WO | 2023154303 | A2 | 8/2023 |
| WO | 2024026280 | A1 | 2/2024 |
| WO | 2024151722 | A1 | 7/2024 |

OTHER PUBLICATIONS

International Preliminary Report on Patentability for Application No. PCT/US2023012572 dated Aug. 22, 2024 (11 pages).

International Search Report and Written Opinion for Application No. PCT/US2023/012572 dated Jul. 20, 2023 (21 pages).

International Search Report and Written Opinion for Application No. PCT/US2023/070893 dated Dec. 15, 2023 (15 pages).

International Search Report and Written Opinion for Application No. PCT/US2024-011034 dated Jun. 10, 2024 (11 pages).

James, T. D., et al. "A glucose-selective molecular fluorescence sensor." (1994): 2207-2209.

Jin, Y., et al. "Recent advances in dynamic covalent chemistry." Chemical Society Reviews 42.16 (2013): 6634-6654.

Johnson, A. R. et al. Single-Step Fabrication of Computationally Designed Microneedles by Continuous Liquid Interface Production. PLoS One 2016, 11 (9), e0162518.

Jover, J. et al. "QSPR prediction of pKa for benzoic acids in different solvents." QSAR & Combinatorial Science 27.5 (2008): 563-581.

Jumper, J., et al. "Highly accurate protein structure prediction with AlphaFold." nature 596.7873 (2021): 583-589.

Kanaan, N. M. et al. Liquid-Liquid Phase Separation Induces Pathogenic Tau Conformations in Vitro. Nat. Commun. 2020, 11 (1), 2809.

Kataoka, K. et al. Totally Synthetic Polymer Gels Responding to External Glucose Concentration: Their Preparation and Application to On-Off Regulation of Insulin Release. Journal of the American Chemical Society. 1998, pp. 12694-12695.

(56) References Cited

OTHER PUBLICATIONS

Kim, W. J., et al. "Insulin smart drug delivery nanoparticles of aminophenylboronic acid-POSS molecule at neutral pH." Scientific reports 11.1 (2021): 21894.
Kim, Y.-C. et al. Microneedles for Drug and Vaccine Delivery. Advanced Drug Delivery Reviews. 2012, pp. 1547-1568.
Kitano, S., et al. "Effect of the incorporation of amino groups in a glucose-responsive polymer complex having phenylboronic acid moieties." Polymers for Advanced Technologies 2.5 (1991): 261-264.
Korn, E. D., et al. "Actin polymerization and ATP hydrolysis." Science 238.4827 (1987): 638-644.
Korsmeyer, R. W. et al. Mechanisms of Solute Release from Porous Hydrophilic Polymers. International Journal of Pharmaceutics. 1983, pp. 25-35.
Krysmann, M. J., et al. "Fibrillisation of hydrophobically modified amyloid peptide fragments in an organic solvent." Soft Matter 3.11 (2007): 1401-1406.
Lebedev, D. V., et al. "Analytical model for determination of parameters of helical structures in solution by small angle scattering: comparison of RecA structures by SANS." FEBS letters 537.1-3 (2003): 182-186.
Leckie, A. M. et al. Frequency, Severity, and Morbidity of Hypoglycemia Occurring in the Workplace in People with Insulin-Treated Diabetes. Diabetes Care 2005, 28 (6), 1333-1338.
Li, J. et al. "Designing hydrogels for controlled drug delivery." Nature Reviews Materials 1.12 (2016): 1-17.
Li, Y., et al. "Aggregation-Induced Asymmetric Charge States of Amino Acids in Supramolecular Nanofibers." The Journal of Physical Chemistry B 127.38 (2023): 8176-8184.
Li, Z., et al. "Supramolecular peptide nanostructures regulate catalytic efficiency and selectivity." Angewandte Chemie International Edition 62.26 (2023): e202303755.
Lim, S. H. et al. High Resolution Photopolymer for 3D Printing of Personalised Microneedle for Transdermal Delivery of Anti-Wrinkle Small Peptide. J. Control. Release 2021, 329, 907-918.
Lim, Z. W. et al. Glucose-Responsive Peptide Coacervates with High Encapsulation Efficiency for Controlled Release of Insulin. Bioconjugate chemistry 29.7 (2018): 2176-2180.
Liu, H. Y. et al. Lower Critical Solution Temperatures of N-Substituted Acrylamide Copolymers in Aqueous Solutions. Polymer. 1999, pp. 6985-6990.
Liu, J. et al. Peptide-Based Liquid Droplets as Emerging Delivery Vehicles. Nature Reviews Materials 2023, 8 (3), 139-141.
Liu, J. et al. Biomaterial Design Inspired by Membraneless Organelles. Matter 2022, 5 (9), 2787-2812.
Lou, J. et al. Predictably Engineering the Viscoelastic Behavior of Dynamic Hydrogels via Correlation with Molecular Parameters. Adv. Mater. 2021, 33 (51), e2104460.
Löwik, Dwpm, et al. "Stimulus responsive peptide based materials." Chemical Society Reviews 39.9 (2010): 3394-3412.
Ma, L. et al. Peptide-Based Coacervates in Therapeutic Applications. Front Bioeng Biotechnol 2022, 10, 1100365.
Ma, R. et al. "Phenylboronic acid-based glucose-responsive polymeric nanoparticles: synthesis and applications in drug delivery." Polymer Chemistry 5.5 (2014): 1503-1518.
Macewan, S. R. et al. Applications of Elastin-like Polypeptides in Drug Delivery. J. Control. Release 2014, 190, 314-330.
Maikawa, C. L. et al. A Co-Formulation of Supramolecularly Stabilized Insulin and Pramlintide Enhances Mealtime Glucagon Suppression in Diabetic Pigs. Nat Biomed Eng 2020, 4 (5), 507-517.
Mantooth, S. M. et al. "Dynamic hydrogels from host-guest supramolecular interactions." Macromolecular Bioscience 19.1 (2019): 1800281.
Marco-Dufort, B. et al. Linking Molecular Behavior to Macroscopic Properties in Ideal Dynamic Covalent Networks. J. Am. Chem. Soc. 2020, 142 (36), 15371-15385.
Marco-Dufort, B. et al. Design of Moldable Hydrogels for Biomedical Applications Using Dynamic Covalent Boronic Esters. Materials Today Chemistry 2019, 12, 16-33.
Marco-Dufort, B. et al. Environment Controls Biomolecule Release from Dynamic Covalent Hydrogels. Biomacromolecules 2021, 22 (1), 146-157.
Mart, R. J., et al. "Peptide-based stimuli-responsive biomaterials." Soft Matter 2.10 (2006): 822-835.
Mason, A. F. et al. Hierarchical Self-Assembly of a Copolymer-Stabilized Coacervate Protocell. J. Am. Chem. Soc. 2017, 139 (48), 17309-17312.
Matsumoto, A., et al. "A synthetic approach toward a self-regulated insulin delivery system." Angewandte Chemie 9.124 (2012): 2166-2170.
Matsumoto, A., et al. "Glucose-responsive polymer bearing a novel phenylborate derivative as a glucose-sensing moiety operating at physiological pH conditions." Biomacromolecules 4.5 (2003): 1410-1416.
McCutcheon's Volume 1, Emulsifiers & Detergents, 1994, North American Edition, pp. 236-239.
Micsonai, A, et al. "Accurate secondary structure prediction and fold recognition for circular dichroism spectroscopy." Proceedings of the National Academy of Sciences 112.24 (2015): E3095-E3103.
Mishra, A. et al. "Biomimetic temporal self-assembly via fuel-driven controlled supramolecular polymerization." Nature communications 9.1 (2018): 1295.
Mishra, A. et al. "ATP-Driven Synthetic Supramolecular Assemblies: From ATP as a Template to Fuel." Angewandte Chemie International Edition 60.6 (2021): 2740-2756.
Mo, R., et al. "Emerging micro-and nanotechnology based synthetic approaches for insulin delivery." Chemical society reviews 43.10 (2014): 3595-3629.
Abbas, M.; et al. Peptide-Based Coacervates as Biomimetic Protocells. Chem. Soc. Rev. 2021, 50 (6), 3690-3705.
Al-Japairai, K.A.S. et al. Current Trends in Polymer Microneedle for Transdermal Drug Delivery. Int. J. Pharm. 2020, 587, 119673.
Ancla, C. et al. "Designed glucose-responsive microgels with selective shrinking behavior." Langmuir 27.20 (2011): 12693-12701.
Andersen, L. W., et al. (2013). Etiology and Therapeutic Approach to Elevated Lactate Levels. In Mayo Clinic Proceedings (vol. 88, No. 10, pp. 1127-1140).
Arora, A.; et al. Micro-Scale Devices for Transdermal Drug Delivery. Int. J. Pharm. 2008, 364 (2), 227-236.
Ashami, K.; et al. Droplet and Fibril Formation of the Functional Amyloid Orb2. J. Biol. Chem. 2021, 297 (1), 100804.
Babinchak, W. M. et al. Liquid-Liquid Phase Separation and Its Mechanistic Role in Pathological Protein Aggregation. J. Mol. Biol. 2020, 432 (7), 1910-1925.
Banach, Ł. et al. "Insulin delivery using dynamic covalent boronic acid/ester-controlled release." Advanced Therapeutics 4.11 (2021): 2100118.
Biancalana, M., et al. "Molecular mechanism of thioflavin-T binding to the surface of β-rich peptide self-assemblies." Journal of molecular biology 385.4 (2009): 1052-1063.
Blocher, W. C. et al. Complex Coacervate-Based Materials for Biomedicine. Wiley Interdiscip. Rev. Nanomed. Nanobiotechnol. 2017, 9 (4) (35 pages).
Boeynaems, S. et al. Arginine-Rich Peptides Can Actively Mediate Liquid-Liquid Phase Separation. Bio Protoc 2017, 7 (17), e2525.
Boija, A. et al. Transcription Factors Activate Genes through the Phase-Separation Capacity of Their Activation Domains. Cell 2018, 175 (7), 1842-1855.e16.
Brebler, I. et al. "SASfit: a tool for small-angle scattering data analysis using a library of analytical expressions." Journal of applied crystallography 48.5 (2015): 1587-1598.
Brooks, W. L. A.; et al. Synthesis and Applications of Boronic Acid-Containing Polymers: From Materials to Medicine. Chem. Rev. 2016, 116 (3), 1375-1397.
Brunsveld, L.; et al. Supramolecular Polymers. Chem. Rev. 2001, 101 (12), 4071-4098.
C.T.F.A. Cosmetic Ingredient Handbook, 1992, pp. 587-592.
Cakmak, F. P.; et al. Prebiotically-Relevant Low Polyion Multivalency Can Improve Functionality of Membraneless Compartments. Nat. Commun. 2020, 11 (1), 5949.

(56) References Cited

OTHER PUBLICATIONS

Cerf, E., et al. "Antiparallel β-sheet: a signature structure of the oligomeric amyloid β-peptide." Biochemical Journal 421.3 (2009): 415-423.
Chabenne, J. R., et al. "Structural refinement of glucagon for therapeutic use." Journal of Medicinal Chemistry 63.7 (2019): 3447-3460.
Chen, G.; et al. Glucose-Responsive Microneedle Patches for Diabetes Treatment. J. Diabetes Sci. Technol. 2019, 13 (1), 41-48.
Cho, N. H. et al. IDF Diabetes Atlas: Global Estimates of Diabetes Prevalence for 2017 and Projections for 2045. Diabetes Res. Clin. Pract. 2018, 138, 271-281.
Chou, D. H.-C. et al. Glucose-Responsive Insulin Activity by Covalent Modification with Aliphatic Phenylboronic Acid Conjugates. Proc. Natl. Acad. Sci. U. S. A. 2015, 112 (8), 2401-2406.
Christopher, M. M., et al. "Increased serum D-lactate associated with diabetic ketoacidosis." Metabolism 44.3 (1995): 287-290.
Cui, H. et al. Self-Assembly of Peptide Amphiphiles: From Molecules to Nanostructures to Biomaterials. Biopolymers 2010, 94 (1), 1-18.
Das, K. et al. "Chemically fueled self-assembly in biology and chemistry." Angewandte Chemie International Edition 60.37 (2021): 20120-20143.
Deng, C. C., et al. "Boronic acid-based hydrogels undergo self-healing at neutral and acidic pH." ACS Macro Letters 4.2 (2015): 220-224.
Deng, J. et al. "ATP-responsive and ATP-fueled self-assembling systems and materials." Advanced Materials 32.42 (2020): 2002629.
Disanto, R. M. et al. Recent Advances in Nanotechnology for Diabetes Treatment. Wiley Interdisciplinary Reviews: Nanomedicine and Nanobiotechnology. 2015, pp. 548-564.
Dong, H., et al. "Self-assembly of multidomain peptides: balancing molecular frustration controls conformation and nanostructure." Journal of the American Chemical Society 129.41 (2007): 12468-12472.
Dong, Y. et al. Injectable and Glucose-Responsive Hydrogels Based on Boronic Acid-Glucose Complexation. Langmuir 2016, 32 (34), 8743-8747.
Drury, J. et al. "Hydrogels for tissue engineering: scaffold design variables and applications." Biomaterials 24.24 (2003): 4337-4351.
Emsley, P. et al. "Coot: model-building tools for molecular graphics." Acta crystallographica section D: biological crystallography 60.12 (2004): 2126-2132.
Fitzsimons, T. M., et al. "Preferential control of forward reaction kinetics in hydrogels crosslinked with reversible conjugate additions." Macromolecules 53.10 (2020): 3738-3746.
Friedman, S. et al. "Complexation of phenylboronic acid with lactic acid. Stability constant and reaction kinetics." Journal of the American Chemical Society 96.17 (1974): 5381-5384.
Fukushima, K. et al. Two-Layered Dissolving Microneedles for Percutaneous Delivery of Peptide/protein Drugs in Rats. Pharm. Res. 2011, 28 (1), 7-21.
Gao, Y., et al. "Enzyme-instructed self-assembly of peptide derivatives to form nanofibers and hydrogels." Peptide Science: Original Research on Biomolecules 94.1 (2010): 19-31.
Garabedian, M. V. et al. Designer Membraneless Organelles Sequester Native Factors for Control of Cell Behavior. Nat. Chem. Biol. 2021, 17 (9), 998-1007.
Ghanaati, S. et al. Dynamic in Vivo Biocompatibility of Angiogenic Peptide Amphiphile Nanofibers. Biomaterials 2009, 30 (31), 6202-6212.
Gleeson, T. T. "Post-exercise lactate metabolism: a comparative review of sites, pathways, and regulation." Annual Review of Physiology 58 (1996): 565-581.
Greenfield, M. A. et al. Tunable Mechanics of Peptide Nanofiber Gels. Langmuir 2010, 26 (5), 3641-3647.
Guo, Z. et al. "Recognition and sensing of various species using boronic acid derivatives." Chemical Communications 48.48 (2012): 5956-5967.
Guvendiren, M. et al. "Shear-thinning hydrogels for biomedical applications." Soft matter 8.2 (2012): 260-272.
Hamley, I. W. "Protein assemblies: nature-inspired and designed nanostructures." Biomacromolecules 20.5 (2019): 1829-1848.
Hannou, S. A., et al. "Fructose metabolism and metabolic disease." The Journal of clinical investigation 128.2 (2018): 545-555.
Hartgerink, J. D. et al. Peptide-Amphiphile Nanofibers: A Versatile Scaffold for the Preparation of Self-Assembling Materials. Proc. Natl. Acad. Sci. U. S. A. 2002, 99 (8), 5133-5138.
Hartgerink, J. D. et al. Self-Assembly and Mineralization of Peptide-Amphiphile Nanofibers. Science 2001, 294 (5547), 1684-1688.
Hendricks, M. P. et al. "Supramolecular assembly of peptide amphiphiles." Accounts of chemical research 50.10 (2017): 2440-2448.
Hennink, W. E., et al. "Novel crosslinking methods to design hydrogels." Advanced drug delivery reviews 64 (2012): 223-236.
Hirose, T. et al. A Guide to Membraneless Organelles and Their Various Roles in Gene Regulation. Nat. Rev. Mol. Cell Biol. 2022, 24 (4), 288-304.
Hoevelmann, U., et al. "Pharmacokinetic and pharmacodynamic characteristics of dasiglucagon, a novel soluble and stable glucagon analog." Diabetes Care 41.3 (2018): 531-537.
European Patent Office. Extended European Search Report for Application No. 23847489.4, dated Nov. 25, 2025 (10 pages).
Wang, Y., et al. "Self-assembled nanostructures regulate H2S release from constitutionally isomeric peptides." Journal of the American Chemical Society 140.44 (2018): 14945-14951.
Wang, Z., et al. "Dual self-regulated delivery of insulin and glucagon by a hybrid patch." Proceedings of the National Academy of Sciences 117.47 (2020): 29512-29517.
Webber, M. J.; et al. "Dynamic and reconfigurable materials from reversible network interactions." Nature Reviews Materials 7.7 (2022): 541-556.
Webber, M. J.; et al. "Engineering responsive supramolecular biomaterials: Toward smart therapeutics." Bioengineering & Translational Medicine 1.3 (2016): 252-266.
Webber, M. J.; et al. (Macro)molecular Self-Assembly for Hydrogel Drug Delivery. Adv. Drug Deliv. Rev. 2021, 172, 275-295.
Webber, M. J.; et al. Smart Approaches to Glucose-Responsive Drug Delivery. J. Drug Target. 2015, 23 (7-8), 651-655.
Webber, M. J.; et al. Supramolecular Nanofibers of Peptide Amphiphiles for Medicine. Isr. J. Chem. 2013, 53 (8), 530-554.
Whitesides, G. M., et al. "Self-assembly at all scales." Science 295.5564 (2002): 2418-2421.
Xiang, Y., et al. "Managing diabetes with hydrogel drug delivery." Advanced Therapeutics 7.1 (2024): 2300127.
Xiang, Y., et al. "Diboronate crosslinking: Introducing glucose specificity in glucose-responsive dynamic-covalent networks." Journal of Controlled Release 348 (2022): 601-611.
Yang, W. et al. "Computer-guided design in molecular recognition: Design and synthesis of a glucopyranose receptor." Angewandte Chemie 113.9 (2001): 1764-1768.
Yao, Y. et al. Glucose-Responsive Vehicles Containing Phenylborate Ester for Controlled Insulin Release at Neutral pH. Biomacromolecules 2012, 13 (6), 1837-1844.
Ye, Y. et al. Polymeric Microneedles for Transdermal Protein Delivery. Advanced Drug Delivery Reviews. 2018, pp. 106-118.
Yesilyurt, V. et al. Injectable Self-Healing Glucose-Responsive Hydrogels with pH-Regulated Mechanical Properties. Advanced Materials. 2016, pp. 86-91.
Yewdall, N. A. et al. Coacervates as Models of Membraneless Organelles. Curr. Opin. Colloid Interface Sci. 2021, 52, 101416.
You, Y. et al. Ultra-Stretchable Hydrogels with Hierarchical Hydrogen Bonds. Sci. Rep. 2020, 10 (1), 11727.
Yount, W. C. et al. Small-Molecule Dynamics and Mechanisms Underlying the Macroscopic Mechanical Properties of Coordinatively Cross-Linked Polymer Networks. J. Am. Chem. Soc. 2005, 127 (41), 14488-14496.
Yu, J. et al. Glucose-Responsive Insulin Patch for the Regulation of Blood Glucose in Mice and Minipigs. Nat Biomed Eng 2020, 4 (5), 499-506.

(56) References Cited

OTHER PUBLICATIONS

Yu, J. et al. Microneedle-Array Patches Loaded with Hypoxia-Sensitive Vesicles Provide Fast Glucose-Responsive Insulin Delivery. Proc. Natl. Acad. Sci. U. S. A. 2015, 112 (27), 8260-8265.
Yu, S., et al. "Glucose-fueled peptide assembly: glucagon delivery via enzymatic actuation." Journal of the American Chemical Society 143.32 (2021): 12578-12589.
Zhou, S. et al. Design and Preparation of 3D Printing Intelligent Poly N,NDimethylacrylamide Hydrogel Actuators. E-polymers 2020, 20(1), 273-281.
Zou, L. et al. Dynamic Supramolecular Hydrogels Spanning an Unprecedented Range of Host-Guest Affinity. ACS Applied Materials & Interfaces. 2019, pp. 5695-5700.
Chen, C.-S., et al. "Nanofibers Self-assembled from Structural Complementary Borono-decapeptides." Macromolecular rapid communications 31.21 (2010): 1903-1908.
Drucker DJ. The role of gut hormones in glucose homeostasis. J Clin Invest. American Society for Clinical Investigation; 2007;117:24-32.
Holst JJ, et al. The role of incretins on insulin function and glucose homeostasis. Endocrinology [Internet]. The Endocrine Society; 2021;162.
International Search Report and Written Opinion for Application No. PCT/US2024/059543 dated Feb. 6, 2025 (11 pages).
IUPAC 1974 Recommendations for Section E, Fundamental Stereochemistry, in Pure Appl. Chem., 1976, 45: 13-30.
Koetting MC, et al. Stimulus-responsive hydrogels: Theory, modern advances, and applications. Mater Sci Eng R Rep. 2015;93:1-49.
Lee NR, et al. Effects of varied sequence pattern on the self-assembly of amphipathic peptides. Biomacromolecules. 2013;14:3267-77.
Levin A, et al. Biomimetic peptide self-assembly for functional materials. Nat Rev Chem. Springer Science and Business Media LLC; 2020;4:615-34.
Li Y, et al. Peptide-based supramolecular hydrogels for delivery of biologics. Bioeng Transl Med. Wiley; 2016;1:306-22.
Li, Z. et al. "pH-responsive self-assembling peptide-based biomaterials: designs and applications." ACS applied bio materials 5.10 (2022): 4635-4651.
Matson JB, et al. Peptide Self-Assembly for Crafting Functional Biological Materials. Curr Opin Solid State Mater Sci. 2011;15:225-35.
Pashuck ET, et al. Tuning supramolecular rigidity of peptide fibers through molecular structure. J Am Chem Soc. 2010;132:6041-6.
Röder PV, et al. Pancreatic regulation of glucose homeostasis. Exp Mol Med. Springer Science and Business Media LLC; 2016;48:e219.
Walther A. Viewpoint: From Responsive to Adaptive and Interactive Materials and Materials Systems: A Roadmap. Adv Mater. 2020;32:e1905111.
Webber MJ, et al. Supramolecular biomaterials. Nat Mater. 2016; 15:13-26.
Yu S, et al. "Engineering disease analyte response in peptide self-assembly." Journal of Materials Chemistry B 12.42 (2024): 10757-10769.
Yu, S., et al. "Glucose-driven droplet formation in complexes of a supramolecular peptide and therapeutic protein." Journal of the American Chemical Society 146.11 (2024): 7498-7505.
Zhang S. Fabrication of novel biomaterials through molecular self-assembly. Nat Biotechnol. Springer Science and Business Media LLC; 2003;21:1171-8.
Badeau BA, et al. Programming stimuli-responsive behavior into biomaterials. Annu Rev Biomed Eng. Annual Reviews; 2019;21:241-65.
Blair HA. Dasiglucagon: First Approval. Drugs. 2021;81:1115-20.
Fu M, et al. Injectable self-assembled peptide hydrogels for glucose-mediated insulin delivery. Biomater Sci. 2018;6:1480-91.
Hovelmann, U.; et al. Pharmacokinetic and Pharmacodynamic Characteristics of Dasiglucagon, a Novel Soluble and Stable Glucagon Analog. Diabetes Care 2018, 41 (3), 531-537.
Jin H, et al. Reduction-responsive amphiphilic polymeric prodrugs of camptothecin-polyphosphoester for cancer chemotherapy. Biomater Sci. 2018;6:1403-13.
Li X, et al. pH-sensitive peptide hydrogel for glucose-responsive insulin delivery. Acta Biomater. Elsevier BV; 2017;51:294-303.
Myers MG Jr, et al. Central nervous system regulation of organismal energy and glucose homeostasis. Nat Metab. 2021;3:737-50.
Webber MJ, et al. Drug delivery by supramolecular design. Chem Soc Rev. 2017;46:6600-20.
Zelzer M, et al. Enzyme responsive materials: design strategies and future developments. Biomater Sci. 2013;1:11-39.
International Search Report and Written Opinion for Application No. PCT/US2024/057860 dated Jan. 22, 2025 (7 pages).
Wu, X., et al. "Selective sensing of saccharides using simple boronic acids and their aggregates." Chemical Society Reviews 42.20 (2013): 8032-8048.
Yu, S., et al. "Glucose-triggered gelation of supramolecular peptide nanocoils with glucose-binding motifs." Advanced Materials 36.16 (2024): 2311498.
Modern Pharmaceutics, Chapters 9 and 10, Banker & Rhodes, eds. (1979).
Mohanty N.A. et al. "Recent advances in glucose-responsive insulin delivery systems: novel hydrogels and future applications." Regen. Biomater. Aug. 2, 20223. 9: rbac056. pp. 1-47.
Mohler, L. K., et al. "Ribonucleoside membrane transport by a new class of synthetic carrier." Journal of the American Chemical Society 115.7 (1993): 2998-2999.
Muggeo, M. et al. Fasting Plasma Glucose Variability Predicts 10-Year Survival of Type 2 Diabetic Patients: The Verona Diabetes Study. Diabetes Care 2000, 23 (1), 45-50.
Muzzopappa, F. et al. Detecting and Quantifying Liquid-Liquid Phase Separation in Living Cells by Model-Free Calibrated Half-Bleaching. Nat. Commun. 2022, 13 (1), 7787.
Norrild, J. C., et al. "Evidence for mono-and bisdentate boronate complexes of glucose in the furanose form. Application of 1JC-C coupling constants as a structural probe." Journal of the American Chemical Society 117.5 (1995): 1479-1484.
Pahal, S. et al. Microneedles for Extended Transdermal Therapeutics: A Route to Advanced Healthcare. Eur. J. Pharm. Biopharm. 2021, 159, 151-169.
Park, S. et al. Dehydration Entropy Drives Liquid-Liquid Phase Separation by Molecular Crowding. Commun Chem 2020, 3 (1), 83.
Peppas, N. A., et al. "Physicochemical foundations and structural design of hydrogels in medicine and biology." Annual review of biomedical engineering 2.1 (2000): 9-29.
Pettus, J., et al. "The past, present, and future of basal insulins." Diabetes/metabolism research and reviews 32.6 (2016): 478-496.
Phypers, B. et al. "Lactate physiology in health and disease." Continuing education in Anaesthesia, critical care & pain 6.3 (2006): 128-132.
Pontiroli, A. E., et al. "Pharmacokinetics of intranasal, intramuscular and intravenous glucagon in healthy subjects and diabetic patients." European journal of clinical pharmacology 45 (1993): 555-558.
Prausnitz, M. R. et al. Current Status and Future Potential of Transdermal Drug Delivery. Nat. Rev. Drug Discov. 2004, 3 (2), 115-124.
Priftis, D. et al. Phase Behaviour and Complex Coacervation of Aqueous Polypeptide Solutions. Soft Matter 2012, 8 (36), 9396-9405.
Punjani, A., et al. "cryoSPARC: algorithms for rapid unsupervised cryo-EM structure determination." Nature methods 14.3 (2017): 290-296.
Rajangam, K. et al. Heparin Binding Nanostructures to Promote Growth of Blood Vessels. Nano Lett. 2006, 6 (9), 2086-2090.
Reinkemeier, C. D. et al. Designer Membraneless Organelles Enable Codon Reassignment of Selected mRNAs in Eukaryotes. Science 2019, 363 (6434).
Remington's Pharmaceutical Sciences, 15th Ed. 1975, pp. 335-337.
Remington's Pharmaceutical Sciences, 18th ed., Mack Printing Company, 1990, pp. 1289-1329.

(56) References Cited

OTHER PUBLICATIONS

Rosales, A. M. et al. "The design of reversible hydrogels to capture extracellular matrix dynamics." Nature Reviews Materials 1.2 (2016): 1-15.
Rowan, S. J., et al. "Dynamic covalent chemistry." Angewandte Chemie International Edition 41.6 (2002): 898-952.
Roxhed, N. et al. Penetration-Enhanced Ultrasharp Microneedles and Prediction on Skin Interaction for Efficient Transdermal Drug Delivery. J. Microelectromech. Syst. 2007, 16 (6), 1429-1440.
Sahoo, J. K., et al. "Injectable network biomaterials via molecular or colloidal self-assembly." Advanced drug delivery reviews 127 (2018): 185-207.
Shen, D. et al. Recent Progress in Design and Preparation of Glucose-Responsive Insulin Delivery Systems. J. Control. Release 2020, 321, 236-258.
Shiino, D. et al. Amine Effect on Phenylboronic Acid Complex with Glucose under Physiological pH in Aqueous Solution. J. Biomater. Sci. Polym. Ed. 1996, 7 (8), 697-705.
Shin, Y. et al. Liquid Phase Condensation in Cell Physiology and Disease. Science 2017, 357 (6357).
Sing, C. E. et al. Recent Progress in the Science of Complex Coacervation. Soft Matter 2020, 16 (12), 2885-2914.
Sis, M. J., et al. "Drug delivery with designed peptide assemblies." Trends in pharmacological sciences 40.10 (2019): 747-762.
Sorrenti, A., et al. "Non-equilibrium steady states in supramolecular polymerization." Nature communications 8.1 (2017): 15899.
Sorrenti, A., et al. "Non-equilibrium supramolecular polymerization." Chemical Society Reviews 46.18 (2017): 5476-5490.
Springsteen, G., et al. "A detailed examination of boronic acid-diol complexation." Tetrahedron 58.26 (2002): 5291-5300.
Stanhope, K. L., et al. "Fructose consumption: recent results and their potential implications." Annals of the New York Academy of Sciences 1190.1 (2010): 15-24.
Stendahl, J. C. et al. Intermolecular Forces in the Self-Assembly of Peptide Amphiphile Nanofibers. Adv. Funct. Mater. 2006, 16 (4), 499-508.
Tang, C., et al. "Fmoc-diphenylalanine self-assembly mechanism induces apparent p K a shifts." Langmuir 25.16 (2009): 9447-9453.
Tang, S., et al. "Dynamic covalent hydrogels as biomaterials to mimic the viscoelasticity of soft tissues." Progress in Materials Science 120 (2021): 100738.
Taylor, N. O. et al. Quantifying Dynamics in Phase-Separated Condensates Using Fluorescence Recovery after Photobleaching. Biophys. J. 2019, 117 (7), 1285-1300.
Tena-Solsona, M., et al. "Non-equilibrium dissipative supramolecular materials with a tunable lifetime." Nature communications 8.1 (2017): 15895.
Titus, A. R. et al. Interfacial Tension and Mechanism of Liquid-Liquid Phase Separation in Aqueous Media. Phys. Chem. Chem. Phys. 2020, 22 (8), 4574-4580.
Trief, P. M. et al. Incorrect Insulin Administration: A Problem That Warrants Attention. Clin. Diabetes 2016, 34 (1), 25-33.
Ulijn, R. V. et al. "Designing peptide based nanomaterials." Chemical Society Reviews 37.4 (2008): 664-675.
Vandenberg, M. A. et al. Biologically Inspired and Chemically Derived Methods for Glucose-Responsive Insulin Therapy. Adv. Healthc. Mater. 2019, 8 (12), e1801466.
Vora, L. K. et al. Novel Bilayer Dissolving Microneedle Arrays with Concentrated PLGA Nano-Microparticles for Targeted Intradermal Delivery: Proof of Concept. J. Control. Release 2017, 265, 93-101.
Wang, B. et al. Glucose-Responsive Micelles from Self-Assembly of Poly(ethylene Glycol)-B-Poly(acrylic Acid-Co-Acrylamidophenylboronic Acid) and the Controlled Release of Insulin. Langmuir 2009, 25 (21), 12522-12528.
Wang, B., et al. "Molecular design of a new diboronic acid for the electrohydrodynamic monitoring of glucose." Angewandte Chemie International Edition 58.31 (2019): 10612-10615.
Wang, H.-W., et al. "Nucleotide-dependent bending flexibility of tubulin regulates microtubule assembly." Nature 435.7044 (2005): 911-915.
Wang, J. et al. "A combined experimental and computational approach reveals how aromatic peptide amphiphiles self-assemble to form ion-conducting nanohelices." Materials chemistry frontiers 4.10 (2020): 3022-3031.
Wang, J. et al. "Peptide self-assembly: thermodynamics and kinetics." Chemical Society Reviews 45.20 (2016): 5589-5604.
Wang, J. et al. Charge-Switchable Polymeric Complex for Glucose-Responsive Insulin Delivery in Mice and Pigs. Sci Adv 2019, 5 (7), eaaw4357.
Wang, J. et al. Core-Shell Microneedle Gel for Self-Regulated Insulin Delivery. ACS Nano 2018, 12 (3), 2466-2473.
Wang, J. et al. Glucose-Responsive Insulin and Delivery Systems: Innovation and Translation. Adv. Mater. 2020, 32 (13), e1902004.

* cited by examiner

FPBA-4aPEG DiPBA-4aPEG Diol-4aPEG PyPBA-4aPEG

DiPBA$_{sm}$

PyPBA$_{sm}$

FPBA$_{sm}$

DiPBA1$_{sm}$

DiAPBA$_{sm}$

DiPBA3$_{sm}$

Diol$_{sm}$

Glucose

Fructose

Sodium Lactate

| ITC: $K_{eq}$ | DiPBA | FPBA | PyPBA |
|---|---|---|---|
| Glucose | 1295.0 $M^{-1}$ | 8.6 $M^{-1}$ | 164.7 $M^{-1}$ |
| Fructose | 745.0 $M^{-1}$ | 673.7 $M^{-1}$ | 367.3 $M^{-1}$ |
| Lactate | 44.6 $M^{-1}$ | 66.9 $M^{-1}$ | 34.9 $M^{-1}$ |
| GdL-diol | 5375.0 $M^{-1}$ | 4922.0 $M^{-1}$ | 5280.0 $M^{-1}$ |

DiPBA:GdL-diol Binding: *Small Molecules*

Fitting a 1:1 binding model:

$\Delta H$ = -4.158 kcal/mol $\Delta S$ = 3.124 cal/mol*K $K_{eq} = 5.4 \times 10^3\ M^{-1}$ DiPBA:GdL-diol Binding: *5kDa PEG chains*

Fitting a 1:1 binding model:

$\Delta H$ = -4.688 kcal/mol $\Delta S$ = 0.349 cal/mol*K $K_{eq} = 3.3 \times 10^3\ M^{-1}$ PBS 22mM Glu PBS 22mM Glu $K_{eq}$ = 6120 M^-1

$K_{eq}$ = 201.1 M^-1

$K_{eq}$ = 382.3 M^-1

$K_{eq}$ = 4568 M^-1

| | DPBA 1 | DiAPBA | DPBA 3 |
|---|---|---|---|
| GdL | 6120 $M^{-1}$ | 1574 $M^{-1}$ | 4568 $M^{-1}$ |
| Glucose | 201.1 $M^{-1}$ | 382.3 $M^{-1}$ | 1035 $M^{-1}$ |

DYNAMIC-COVALENT HYDROGELS WITH GLUCOSE-SPECIFIC AND GLUCOSE-RESPONSIVE DIBORONATE CROSSLINKING

CROSS-REFERENCE TO RELATED APPLICATIONS

This application is a U.S. national stage entry of International Patent Application No. PCT/US2023/012572, filed on Feb. 8, 2023, which claims priority to U.S. Provisional Patent Application No. 63/267,762 filed on Feb. 9, 2022, the entire contents of each of which are fully incorporated herein by reference.

FEDERALLY SPONSORED RESEARCH

This invention was made with government support under grant number 1944875 awarded by the National Science Foundation. The government has certain rights in the invention.

BACKGROUND

Hydrogels are a common class of biomaterials, with their network structure offering a surrogate of the natural extracellular matrix and their highly hydrated porosity enabling controlled release of encapsulated macromolecules. The polymers used in composing hydrogels are typically hydrophilic, and once crosslinked afford a material that can imbue water in an amount many times the dry weight of the polymer itself. Hydrogels can be characterized by their mode of crosslinking; chemical crosslinking entails the permanent formation of covalent crosslinks between polymer chains, while physical crosslinking arises from transient and reversible interactions or entanglements. The mechanical properties of the bulk hydrogel materials usually follow directly from their mode of crosslinking. Covalent crosslinks commonly yield materials with higher modulus that do not flow or permanently deform under moderate strain but exhibit permanent loss of mechanical character under high strain. Conversely, physical crosslinking typically gives rise to materials with more dynamic viscoelastic behavior, enabling flow under applied strain and exhibiting self-healing character.

Dynamic-covalent chemistry encompasses a number of equilibrium-governed covalent bonds, including many classical organic reaction mechanisms. Recently, dynamic-covalent crosslinking has gained attention for its use in the preparation of hydrogels. When used in the context of hydrogel crosslinking, this approach enables covalent bonding interactions with dynamic exchange and finite average lifetime. Accordingly, this mode of crosslinking, in principle, affords aspects of both chemical and physical crosslinking in yielding dynamic viscoelastic materials with well-defined crosslinking interactions and excellent mechanical properties while also undergoing equilibrium-governed bond exchange that enables network restructuring and self-healing. Certain of these dynamic-covalent interactions are further modulated by competition from naturally occurring analytes, enabling their equilibrium-governed bond exchange to be integrated into stimuli-responsive platforms. One such chemistry that has been explored in this regard is dynamic-covalent bonding between phenylboronic acids (PBAs) and cis-1,2 or cis-1,3 diols. In the context of drug delivery for diabetes, PBA-diol chemistry is susceptible to competition from glucose (a cis-1,2 diol), which in turn affords hydrogels where the extent of network crosslinking is rendered glucose-dependent.

Prior reports have described hydrogel materials crosslinked using PBA-diol interactions and explored glucose-responsive release of encapsulated macromolecules from these networks. Rich phenomena in polymer physics have also been elucidated from ideal network platforms prepared using this chemistry. At the same time, PBA chemistry presents two key drawbacks in its application for use in glucose-responsive materials. First, common diol chemistries used for polymer crosslinking have affinity for PBA significantly higher than that of glucose, which itself does not typically bind PBA with affinity sufficient for optimal function under physiological glucose concentrations. This challenge, in turn, limits glucose-responsive function of the material. Second, the non-specific nature of the PBA-glucose interaction means these linkages are subject to interference from binding of common analytes such as fructose and lactate, which actually bind with higher affinity than glucose to most PBA chemistries. Accordingly, limited glucose-responsiveness and sensitivity to non-glucose analytes present in the body act contrary to the envisioned application of these materials for stimuli-responsive release of insulin to control blood glucose levels in diabetes.

What is needed are boronic acid motifs that bind glucose with high affinity and improved specificity and that can be used to prepare dynamic injectable materials with improved function in encapsulation and glucose-triggered release of insulin in vitro and in vivo.

SUMMARY

One embodiment described herein is hydrogel, the hydrogel comprising:

(i) a diboronate compound of formula (I):

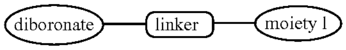 , (I)

wherein:

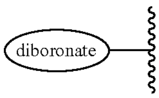 is 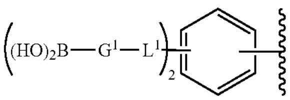 , wherein:

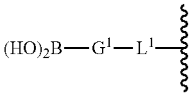 is 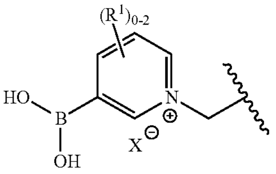 or

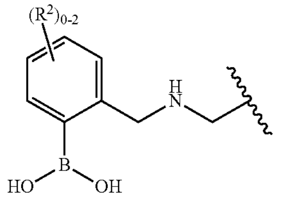 ;

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$;

$X^{\ominus}$ is an anion having a net charge of −1;

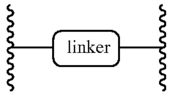

is a linking moiety; and

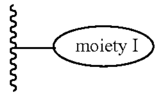

is a first moiety comprising a hydrophilic polymer, a hyperbranched macromolecule, or a combination thereof; and (ii) a diol compound of formula (II):

(II)

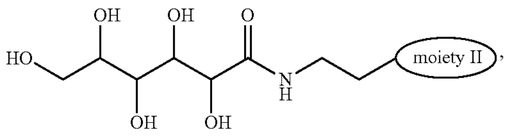

wherein:

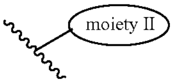

is a second moiety comprising a hydrophilic polymer, a hyperbranched macromolecule, or a combination thereof;

wherein the diboronate compound of formula (I) and the diol compound of formula (II) form crosslinks by dynamic-covalent bonds.

In another aspect,

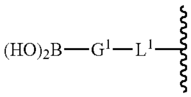

is

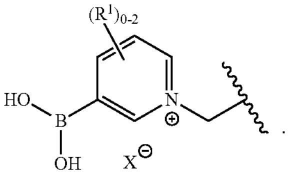

.

In another aspect,

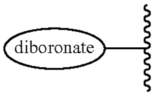

is

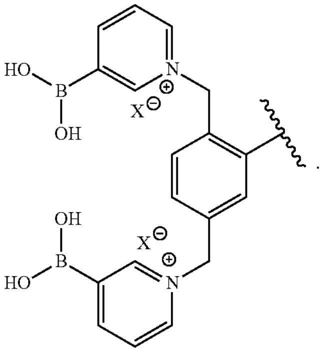

.

In another aspect, $X^{\ominus}$ is $Br^-$, $Cl^-$, $NO_3^-$, $H_2PO_4^-$, $H_2PO_3^-$, $HSO_4^-$, $HSO_3^-$, $H_3C^-$, $SO_3^-$, $HCO_3^-$, $HCO_2^-$, $H_3C—CO_2^-$, $HC_2O_4^-$, or $TsO^-$. In another aspect, $X^{\ominus}$ is $Br^-$ or $Cl^-$. In another aspect,

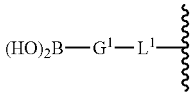

is

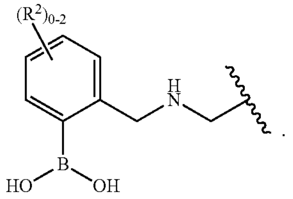

.

In another aspect,

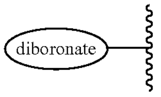

i

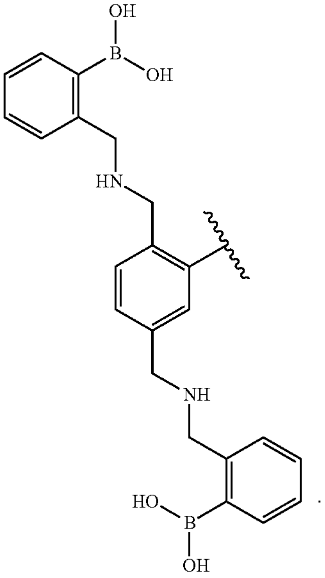

.

In another aspect,

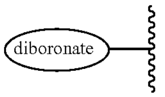

has an equilibrium constant ($K_{eq}$) for binding glucose of at least 350 $M^{-1}$. In another aspect,

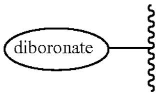

has an equilibrium constant ($K_{eq}$) for binding glucose of at least 1000 $M^{-1}$. In another aspect,

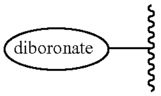

has an equilibrium constant ($K_{eq}$) for binding glucose that is at least 20 times greater than equilibrium constant of

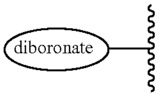

for binding lactate. In another aspect,

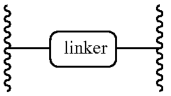

comprises:

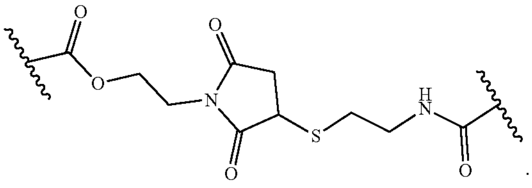 [SMILES: *C(=O)NCCSC1CC(=O)N(CCOC(*)=O)C1=O]

.

In another aspect,

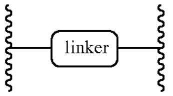

comprises:

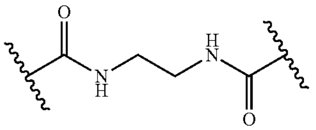

.

In another aspect,

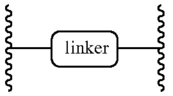

comprises

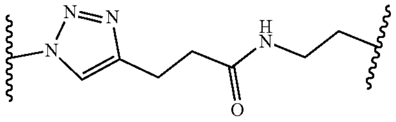

.

In another aspect,

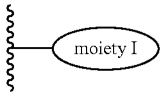

comprises a branched polymer. In another aspect, the branched polymer comprises a polyalkylene glycol. In another aspect, the branched polymer is a four-armed polymer. In another aspect, the diboronate compound of formula (I) comprises:

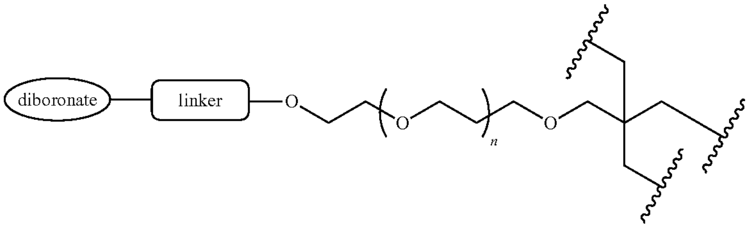

, wherein n is 2 to 250. In another aspect,

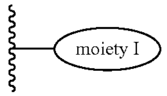

comprises a dendrimer. In another aspect, the dendrimer is a polyamidoamine dendrimer. In another aspect,

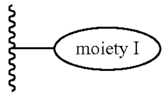

comprises a linear polymer. In another aspect, the linear polymer comprises a polysaccharide. In another aspect, the polysaccharide comprises hyaluronic acid. In another aspect, the molar ratio of the diboronate compound of formula (I) to the diol compound of formula (II) is 1:1. In another aspect,

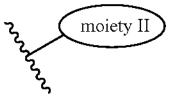

comprises a branched polymer. In another aspect, the branched polymer is a four-armed or an eight-armed polymer. In another aspect, the branched polymer comprises polyethylene glycol. In another aspect, the diol compound of formula (II) comprises:

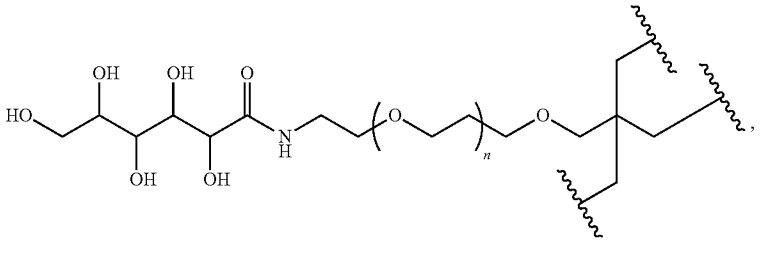

wherein n is 2 to 250. In another aspect,

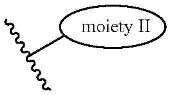

comprises a dendrimer. In another aspect, the dendrimer is a polyamidoamine dendrimer. In another aspect,

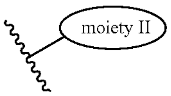

comprises a linear polymer.

Another embodiment described herein is a pharmaceutical composition comprising insulin encapsulated within a hydrogel.

Another embodiment described herein is a method of delivering insulin to a subject in need thereof, the method comprising: administering a pharmaceutical composition to a subject in need thereof, the pharmaceutical composition comprising insulin encapsulated within a hydrogel, the hydrogel comprising:

(i) a diboronate compound of formula (I):

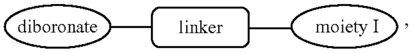

(I)

wherein:

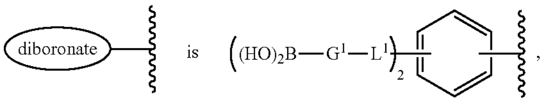

wherein:

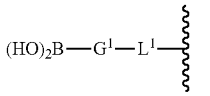

is

-continued

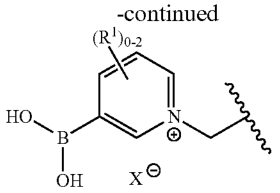

or

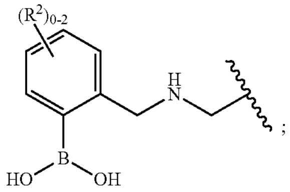

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$; and $X^{\ominus}$ is an anion having a net charge of −1;

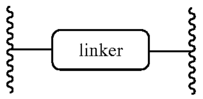

a linking moiety; and

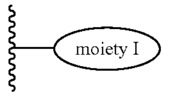

is a first moiety comprising a hydrophilic polymer, a hyperbranched macromolecule, or a combination thereof; and (ii) a diol compound of formula (II):

(II)

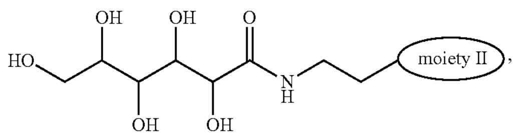

wherein:

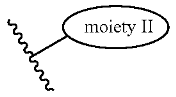

is a second moiety comprising a hydrophilic polymer, a hyperbranched macromolecule, or a combination thereof;

wherein the diboronate compound of formula (I) and the diol compound of formula (II) form crosslinks by dynamic-covalent bonds. In another aspect, the subject in need thereof has diabetes. In another aspect, the insulin is administered to the subject at 0.05-10 international units (IU)/kg. In another aspect, following administration of the pharmaceutical composition, the subject has blood glucose levels of about 60-110 mg/dL.

Another embodiment described herein is the use of a hydrogel, a pharmaceutical composition, or a method for delivering insulin to a subject in need thereof.

DESCRIPTION OF THE DRAWINGS

FIG. 1A illustrates network hydrogels prepared from dynamic-covalent crosslinking interactions between aryl boronates and diols, each appended to a 4-arm (4a) polyethylene glycol (PEG) macromer. As these interactions are susceptible to competition from free diols such as glucose, this approach offers a route to materials for glucose-responsive delivery of insulin. However, tradition phenylboronic acids (PBAs) used thus far do not bind glucose with affinity ($K_{eq}$) necessary for optimal function in physiologic conditions, and also bind to non-glucose analytes such as fructose and lactate with high affinity. The present work instead explores dynamic-covalent crosslinking with a diboronate (DiPBA) group, offering high-affinity glucose binding and being more resistant to binding non-glucose analytes, with the goal of more sensitive and specific glucose-responsive function. FIG. 1B shows chemical structures of 4-arm PEG (4aPEG) macromers used in this work, bearing a fluorine-substituted PBA (FPBA), diboronate motif (DiPBA), pyridinium-PBA (PyPBA), or glucose-like diol ("Diol") moiety. FIG. 1C shows the preparation of hydrogels crosslinked using diboronate motifs affords more glucose-specific and glucose-responsive function compared to traditional routes based on phenylboronic acid that suffer from interference by non-glucose analytes.

FIG. 15A shows a DiPBA network prepared in PBS (left) and 22 mM glucose/PBS solution (right). FIG. 15B shows a FPBA network prepared in PBS (left) and 22 mM glucose/PBS solution (right).

DETAILED DESCRIPTION

Figure 1A:
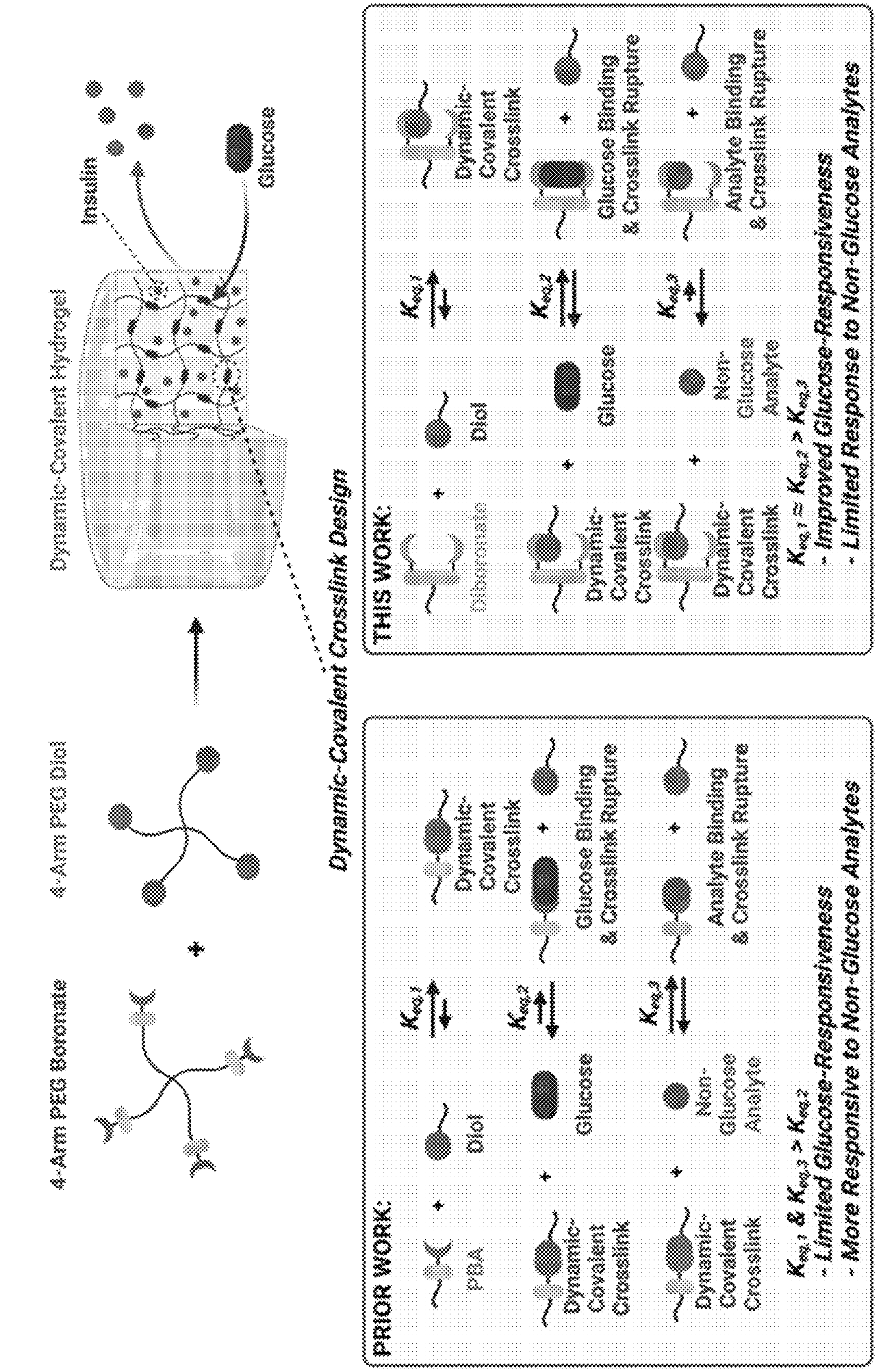
FIGS. 1A-C show conceptual schematics of exemplary hydrogels.

Unless otherwise defined, all technical and scientific terms used herein have the same meaning as commonly understood by one of ordinary skill in the art. For example, any nomenclatures used in connection with, and techniques of biochemistry, molecular biology, immunology, microbiology, genetics, cell and tissue culture, and protein and nucleic acid chemistry described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "-" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refers to a substantially non-toxic, but sufficient amount of an action, agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

As used herein, "treating or preventing a disease or disorder" includes alleviating and mitigating a disease or disorder, and improving symptoms, and also includes lowering the probability of getting a disease or disorder.

As used herein, the terms "pharmaceutically acceptable carrier" or "pharmaceutically acceptable excipient" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see e.g., *Remington's Pharmaceutical Sciences,* $18^{th}$ ed., Mack Printing Company, 1990, pp. 1289-1329). Except insofar as any conventional carrier is incompatible with the active ingredient, its use in the therapeutic or pharmaceutical compositions is contemplated.

As used herein, the terms "salt" or "salts" refers to an acid addition or base addition salt of a compound of the invention. "Salts" include in particular "pharmaceutical acceptable salts." The term "pharmaceutically acceptable salts" refers to salts that retain the biological effectiveness and properties of the compounds of this invention and, which typically are not biologically or otherwise undesirable. In many cases, the compounds described herein are capable of forming acid and/or base salts by virtue of the presence of amino and/or carboxyl groups or groups similar thereto.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* $3^{rd}$ Edition, Cambridge University Press, Cambridge, 1987; the entire contents of each of which are incorporated herein by reference.

The term "alkoxy," as used herein, refers to a group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_4$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, $—CH_2—$, $—CD_2$-, $—CH_2CH_2—$, $—CH_2CH_2CH_2—$, $—CH_2CH_2CH_2CH_2—$, and $—CH_2CH_2CH_2CH_2CH_2—$.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means $—NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be $—NR_x^-$, wherein $R_x$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1] heptanyl).

Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1] heptenyl).

Exemplary monocyclic cycloalkenyl rings include cyclopentenyl, cyclohexenyl or cycloheptenyl. Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The terms cycloalkylene and heterocyclylene refer to divalent groups derived from the base ring, i.e., cycloalkane, heterocycle. For purposes of illustration, examples of cycloalkylene and heterocyclylene include, respectively,

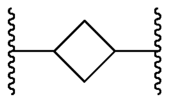

and

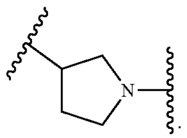

.

Cycloalkylene and heterocyclylene include a geminal divalent groups such as 1,1-$C_{3-6}$cycloalkylene (i.e.,

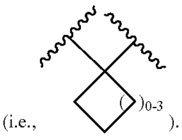

).

A further example is 1,1-cyclopropylene (i.e.,

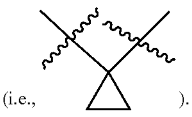

).

The term "fluoroalkyl," as used herein, means an alkyl group, as defined herein, in which one, two, three, four, five, six, seven or eight hydrogen atoms are replaced by fluorine.

Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkylene," as used herein, means an alkylene group, as defined herein, in which one, two, three, four, five, six, seven or eight hydrogen atoms are replaced by fluorine.

Representative examples of fluoroalkyl include, but are not limited to $—CF_2—$, $—CH_2CF_2—$, 1,2-difluoroethylene, 1,1,2,2-tetrafluoroethylene, 1,3,3,3-tetrafluoropropylene, 1,1,2,3,3-pentafluoropropylene, and perfluoropropylene such as 1,1,2,2,3,3-hexafluoropropylene.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaromatic ring (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g., 1, 2, 3, or 4 heteroatoms independently selected from O, S, and N). The five membered aromatic monocyclic rings have two double bonds, and the six membered aromatic monocyclic rings have three double bonds. The bicyclic heteroaryl is an 8- to 12-membered ring system and includes a fused bicyclic heteroaromatic ring system (i.e., 10π electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, tetrahydroisoquinolinyl, 7-oxabicyclo[2.2.1]heptanyl, hexahydro-2H-cyclopenta[b]furanyl, 2-oxaspiro[3.3]heptanyl, 3-oxaspiro[5.5]undecanyl, 6-oxaspiro[2.5]octan-1-yl, and 3-oxabicyclo[3.1.0]hexan-6-yl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocyclyls are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Dynamic-covalent chemistry is valuable for hydrogel crosslinking, leveraging equilibrium-governed reversible interactions to realize viscoelastic materials with dynamic properties and self-healing character. The bonding between aryl boronates and diols is one particular dynamic-covalent chemistry of interest. The extent of network crosslinking using this motif can be subject to competition from ambient diols such as glucose, offering a strategy for glucose-directed release of insulin to control diabetes. However, the majority of work to—date uses phenylboronic acids (PBAs) that suffer from low-affinity glucose binding relative to their binding of the synthetic diols used in crosslinking, limiting material responsiveness. Moreover, PBA chemistry is also subject to competition from binding non-glucose analytes such as fructose and lactate, limiting the specificity of sensing. Here, dynamic-covalent hydrogels are prepared that, for the first time, leverage a diboronate motif with enhanced glucose binding and improved glucose specificity.

This crosslinking yields hydrogels that, when compared to traditional PBA crosslinking, offer more glucose-responsive insulin release that is minimally impacted by non-glucose analytes.

Figure 1B:
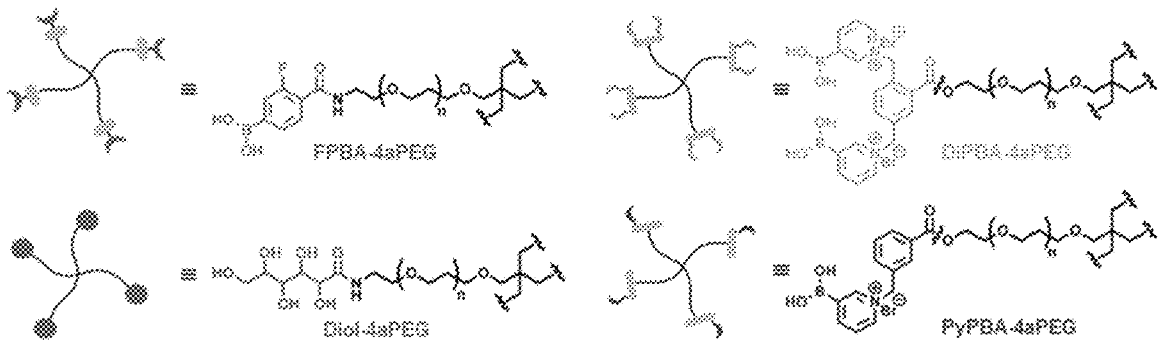
Figure 1C:
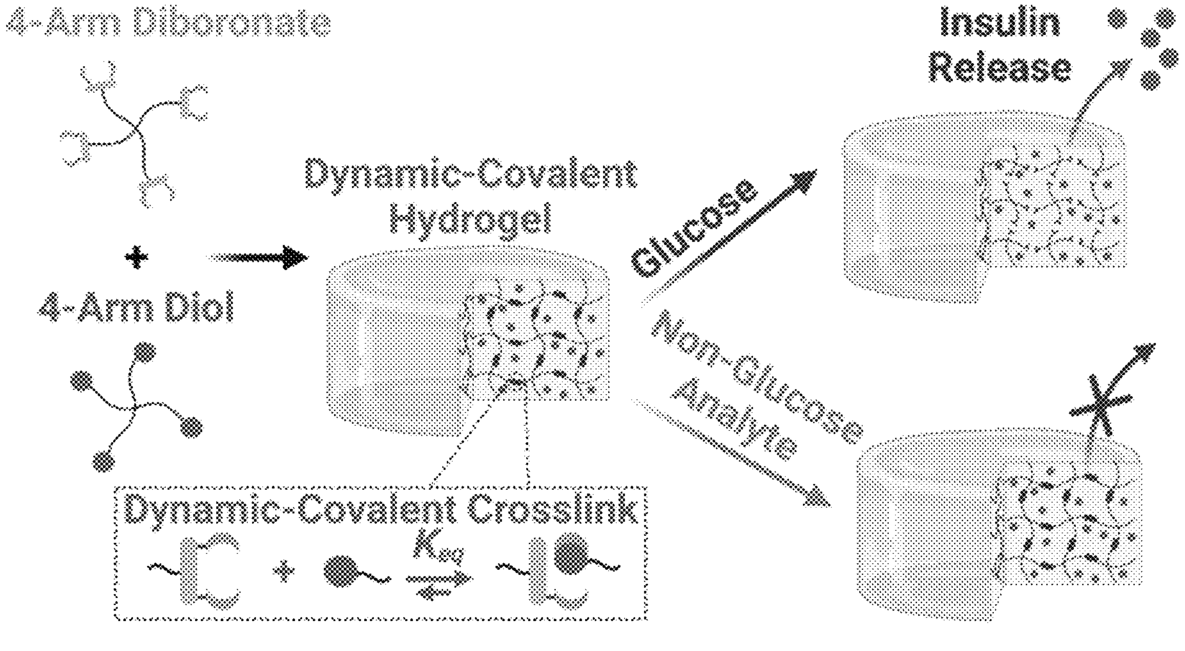

A dynamic-covalent crosslinking chemistry is disclosed that leverages high-affinity and glucose-specific interactions from di-phenylboronic acid (DiPBA) motifs (FIG. 1A). Inspired by work using rigid aromatic diboronates as fluorescent or electrochemical glucose sensors, the present study explores the use of a related motif in the formation of ideal network hydrogels. By appending a DiPBA motif on a 4-arm polyethylene glycol (4aPEG), its mixture with a Diol-4aPEG yields dynamic and self-healing hydrogels (FIG. 1B). These materials exhibit improved glucose-responsivity when compared to a standard PBA chemistry (FPBA) used in previous studies and are more resistant to physiologically relevant concentrations of fructose and lactate. This design uses motifs that bind glucose with high affinity and improved specificity and offers dynamic injectable materials with improved function in encapsulation and glucose-triggered release of insulin in vitro and in vivo.

Compounds

In one aspect, the invention provides hydrogels. Exemplary hydrogels of the present invention comprise a diboronate compound (e.g., a diboronate compound of formula (I)) and a diol compound (e.g., a diol compound of formula (II)). In various instances, the diboronate compound and the diol compound form crosslinks by dynamic-covalent bonds. In various instances, the molar ratio of the diboronate compound to the diol compound is 1:1.

Diboronate Compounds of Formula (1)

In one aspect, the invention provides diboronate compounds of formula (I):

(I)

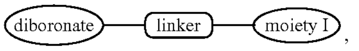, wherein:

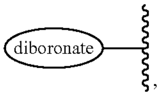, 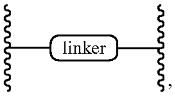, and 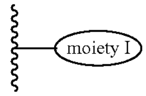

are as defined herein.

In various instances,

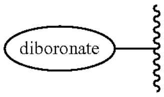 is 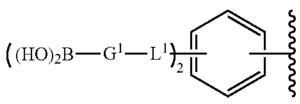, wherein:

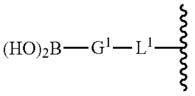 is 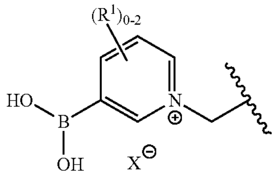 or

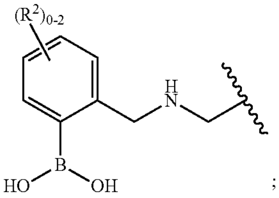 ;

$R^1$, at each occurrence, is independently $C_{1-4}$alkyl, cyclopropyl, $C_{1-2}$fluoroalkyl, —F, —CN, or —$NO_2$; and $R^2$, at each occurrence, is independently $C_{1-4}$alkyl, cyclopropyl, $C_{1-2}$fluoroalkyl, —F, —CN, or —$NO_2$; and $X^{\ominus}$ is an anion having a net charge of −1.

In various instances,

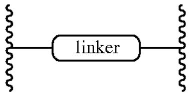

is a linking moiety.

In various instances,

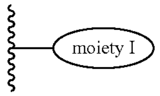

is a first moiety comprising a hydrophilic polymer, a hyperbranched macromolecule, or a combination thereof.

In some instances,

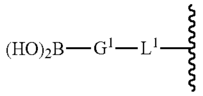

may be

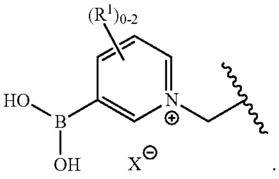.

In some instances

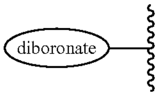

may be

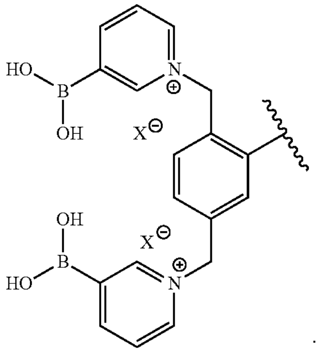

.

In various instances, $X^{\ominus}$ may be $Br^-$, $Cl^-$, $NO_3^-$, $H_2PO_4^-$, $H_2PO_3^-$, $HSO_4^-$, $HSO_3^-$, $H_3C—SO_3^-$, $HCO_3$, $HCO_2^-$, $H_3C—CO_2^-$, $HC_2O_4^-$, or $TsO^-$.

In some instances, $X^{\ominus}$ may be $Br^-$ or $Cl^-$.

In various instances,

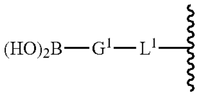

may be

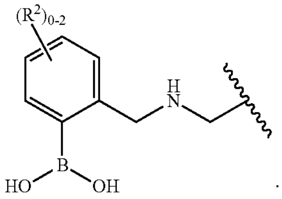

.

In some instances,

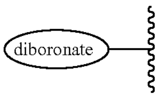

may be

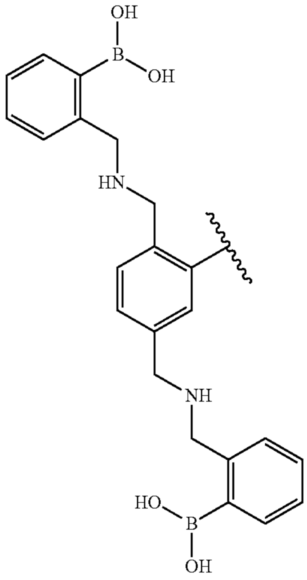

.

In various instances,

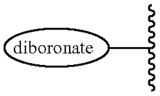

may have an equilibrium constant ($K_{eq}$) for binding glucose of at least 350 $M^{-1}$.

In some instances,

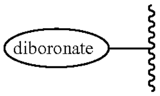

may have an equilibrium constant ($K_{eq}$) for binding glucose of at least 1000 $M^{-1}$.

In some instances,

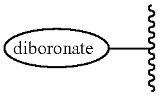

may have an equilibrium constant ($K_{eq}$) for binding glucose that is at least 20 times greater than equilibrium constant of

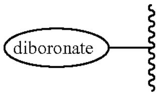

for binding lactate.

In various instances,

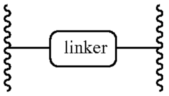

may comprise:

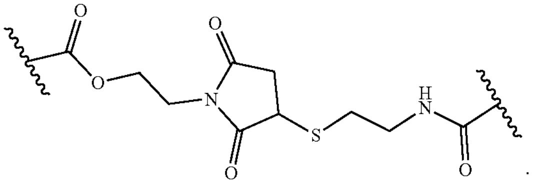 [SMILES: *C(=O)NCCSC1CC(=O)N(CCOC(*)=O)C1=O]

In some instances,

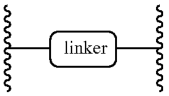

may comprise:

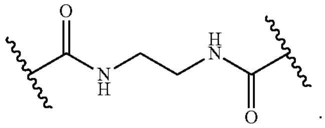 [SMILES: *C(=O)NCCNC(*)=O]

In some instances,

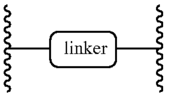

may comprise:

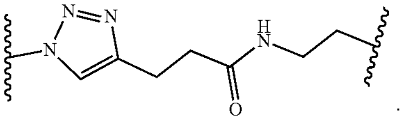 [SMILES: *CCNC(=O)CCc1cn(*)nn1]

In some instances,

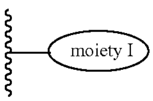

may comprise a branched polymer. The branched polymer may comprise a polyalkylene glycol. The polyalkylene glycol may comprise polyethylene glycol. The branched polymer may be a four-armed polymer.

In some instances, the diboronate compound of formula (I) may comprise:

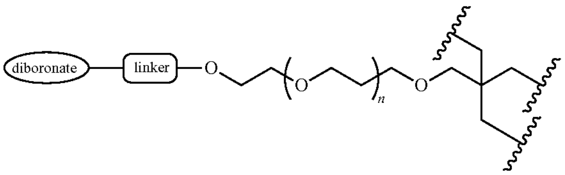

wherein n is 2 to 250.

In some instances,

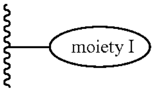

may comprise a dendrimer. The dendrimer may be a polyamidoamine dendrimer.

In some instances,

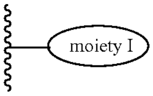

may comprise a linear polymer. The linear polymer may comprise a polysaccharide. The polysaccharide may comprise hyaluronic acid.

Diol Compounds of Formula (II)

In another aspect, the invention provides diols of formula (II):

(II)

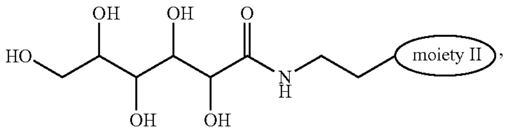

wherein

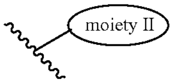

is as defined

In various instances

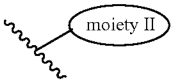

is a second moiety comprising a hydrophilic polymer, a hyperbranched macromolecule, or a combination thereof.

In various instances,

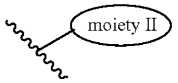

comprises a branched polymer. The branched polymer may comprise polyethylene glycol.

In some instances, the diol compound of formula (II) may comprise:

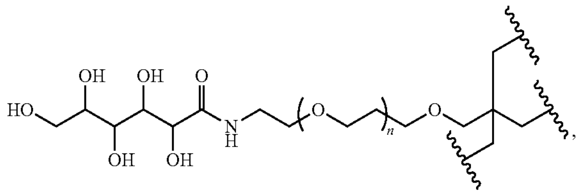

wherein n is 2 to 250.

In some instances,

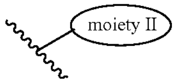

may comprise a dendrimer. The dendrimer may be a polyamidoamine dendrimer.

In some instances,

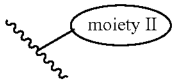

may comprise a linear polymer.

Compound names can be assigned by using Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

In the compounds of formula (I), formula (II), and any subformulas, any "hydrogen" or "H," whether explicitly recited or implicit in the structure, encompasses hydrogen isotopes 1H (protium) and $^{2}H$ (deuterium).

The present disclosure also includes isotopically-labeled compounds (e.g., deuterium labeled), where an atom in the isotopically-labeled compound is specified as a particular isotope of the atom. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Isotopically-enriched forms of compounds of formula (I), or any subformulas, may generally be prepared by conventional techniques known to those skilled in the art or by processes analogous to those described in the accompanying Examples using an appropriate isotopically-enriched reagent in place of a non-isotopically-enriched reagent. The extent of isotopic enrichment can be characterized as a percent incorporation of a particular isotope at an isotopically-labeled atom (e.g., % deuterium incorporation at a deuterium label).

Pharmaceutical Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides, and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

General Synthesis of Compounds

Optimum reaction conditions and reaction times for each individual step can vary depending on the particular reactants employed and substituents present in the reactants used.

Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature.

Starting materials, if not commercially available, can be prepared by procedures selected from standard organic chemical techniques, techniques that are analogous to the synthesis of known, structurally similar compounds, or techniques that are analogous to the above-described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and TW Greene, in Greene's book titled Protective Groups in Organic Synthesis (4th ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization, or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

Pharmaceutical Compositions

Pharmaceutical compositions of the present invention comprise insulin encapsulated within the hydrogels disclosed herein (i.e., "hydrogel-encapsulated insulin").

Hydrogel-encapsulated insulin may be incorporated into pharmaceutical compositions suitable for administration to a subject (such as a patient, which may be a human or non-human). The pharmaceutical compositions may include a "therapeutically effective amount" or a "prophylactically effective amount" of the active agent (insulin). A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A "therapeutically effective amount" is also one in which any toxic or detrimental effects are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical compositions may include pharmaceutically acceptable carriers. The term "pharmaceutically acceptable carrier," as used herein, means a non-toxic, inert solid, semi-solid or liquid filler, diluent, encapsulating material, or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the hydrogels and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "*Remington's Pharmaceutical Sciences*," (Meade Publishing Co., Easton, Pa.). Therapeutic compositions must typically be sterile and stable under the conditions of manufacture and storage.

The route by which the hydrogel-encapsulated insulin is administered, and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions. Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%. Suitable colorants include a colorant such as an FD&C dye. When used, the amount of colorant in a systemic or topical composition is typically about 0.005 to about 0.1%. Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%. Suitable antioxidants include butylated hydroxyanisole ("BHA"), butylated hydroxytoluene ("BHT"), and vitamin E. The amount of antioxidant(s) in a systemic or topical composition is typically about 0.1 to about 5%. Suitable preservatives include benzalkonium chloride, methyl paraben and sodium benzoate. The amount of preservative(s) in a systemic or topical composition is typically about 0.01 to about 5%. Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%. Suitable suspending agents include AVICEL RC-591 (from FMC Corporation of Philadelphia, PA) and sodium alginate. The amount of suspending agent(s) in a systemic or topical composition is typically about 1 to about 8%. Suitable surfactants include lecithin, Polysorbate 80, and sodium lauryl sulfate, and the TWEENS from Atlas Powder Company of Wilmington, Delaware. Suitable surfactants include those disclosed in the C.T.F.A. *Cosmetic Ingredient Handbook,* 1992, pp. 587-592*; Remington's Pharmaceutical Sciences,* 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of actives and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose, and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active and a carrier including one or more diluents disclosed above in a capsule comprising gelatin. Granules typically comprise an active, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention. Solid compositions may be coated by conventional methods, typically with pH or time-dependent coatings, such that the hydrogel-encapsulated insulin is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include the hydrogel-encapsulated insulin and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol, and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compositions can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed hydrogel and a carrier. The carrier of the topical composition preferably aids penetration of the hydrogels into the skin. The carrier may further include one or more optional components.

The amount of the carrier employed in conjunction with the hydrogel-encapsulated insulin is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* $2^{nd}$ ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof.

Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%. The amount of thickener(s) in a topical composition is typically about 0% to about 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%. The amount of fragrance in a topical composition is typically about 0% to about 0.5%, particularly, about 0.001% to about 0.1%. Suitable pH adjusting additives include HCl or NaOH in amounts sufficient to adjust the pH of a topical pharmaceutical composition.

Methods of Treatment

The disclosed insulin-encapsulated hydrogels may be used to deliver insulin to a subject. The methods of treatment may comprise administering to a subject in need of insulin a pharmaceutical composition comprising insulin encapsulated within a hydrogel, as described herein. In various instances, subject in need thereof may have diabetes (e.g., Type 1 diabetes).

In various instances, insulin may be administered to the subject at 0.05-10 international units (IU)/kg. In various instances, insulin may be administered to the subject at 0.10-10 IU/kg; 1-10 IU/kg; 1-9 IU/kg; 2-8 IU/kg; 2-7 IU/kg; 3-7 IU/kg; 3-6 IU/kg; or 4-6 IU/kg. In various instances, insulin may be administered to the subject at no greater than 10 IU/kg; no greater than 9 IU/kg; no greater than 8 IU/kg; no greater than 7 IU/kg; no greater than 6 IU/kg; no greater than 5 IU/kg; no greater than 4 IU/kg; no greater than 3 IU/kg; no greater than 2 IU/kg; no greater than 1 IU/kg; no greater than 0.50 IU/kg; no greater than 0.10 IU/kg; or no greater than 0.05 IU/kg. In various instances, insulin may be administered to the subject at no less than 0.05 IU/kg; no less than 0.10 IU/kg; no less than 0.50 IU/kg; no less than 1 IU/kg; no less than 2 IU/kg; no less than 3 IU/kg; no less than 4 IU/kg; no less than 5 IU/kg; no less than 6 IU/kg; no less than 7 IU/kg; no less than 8 IU/kg; no less than 9 IU/kg; or no less than 10 IU/kg.

In various instances, following administration of the pharmaceutical composition, the subject has blood glucose levels of about 60-110 mg/dL. In various instances, following administration of the pharmaceutical composition, the subject has blood glucose levels of about 65-105 mg/dL; about 70-100 mg/dL; about 75-95 mg/dL; or about 80-90 mg/dL. In various instances, following administration of the pharmaceutical composition, the subject has blood glucose levels of no greater than about 110 mg/dL; no greater than about 100 mg/dL; no greater than about 90 mg/dL; no greater than about 80 mg/dL; no greater than about 70 mg/dL; or no greater than about 60 mg/dL.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A hydrogel, the hydrogel comprising:

(i) a diboronate compound of formula (I):

(I)

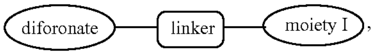, wherein:

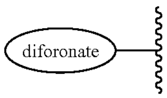 is 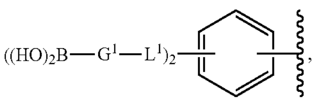, wherein:

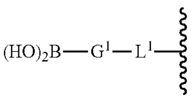 is 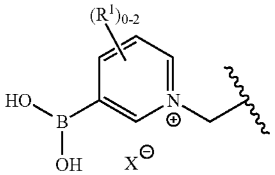 or

-continued

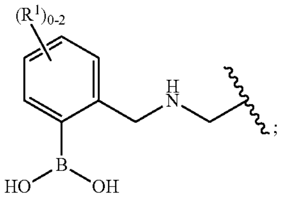;

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$;

$X^{\ominus}$ is an anion having a net charge of −1;

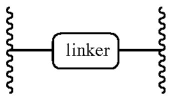

is a linking moiety; and

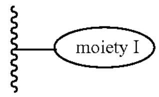

is a first moiety comprising a hydrophilic polymer, a hyperbranched macromolecule, or a combination thereof; and (ii) a diol compound of formula (II):

(II)

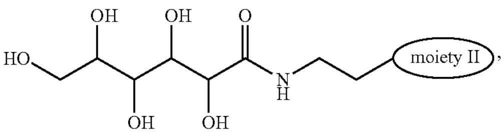, wherein:

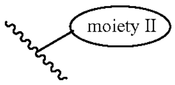

is a second moiety comprising a hydrophilic polymer, a hyperbranched macromolecule, or a combination thereof;

wherein the diboronate compound of formula (I) and the diol compound of formula (II) form crosslinks by dynamic-covalent bonds.

Clause 2. The hydrogel of clause 1, wherein

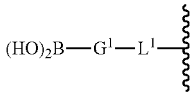 is 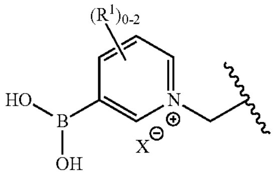 .

Clause 3. The hydrogel of clause 1 or 2, wherein

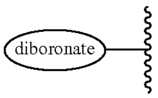 is 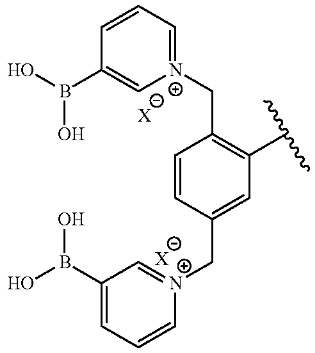 .

Clause 4. The hydrogel of any one of clauses 1-3, wherein $X^{\ominus}$ is $Br^-$, $Cl^-$, $NO_3^-$, $H_2PO_4^-$, $H_2PO_3^-$, $HSO_4$, $HSO_3^-$, $H_3C—SO_3^-$, $HCO_3^-$, $HCO_2^-$, $H_3C—CO_2^-$, $HC_2O_4^-$, or $TsO^-$.

Clause 5. The hydrogel of any one of clauses 1-4, wherein $X^{\ominus}$ is $Br^-$ or $Cl^-$.

Clause 6. The hydrogel of clause 1, wherein

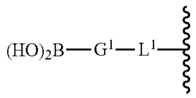 is 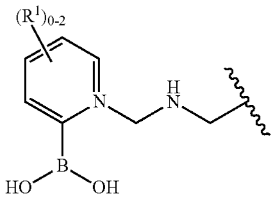 .

Clause 7. The hydrogel of clause 1 or 6, wherein

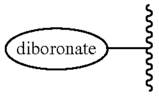 is 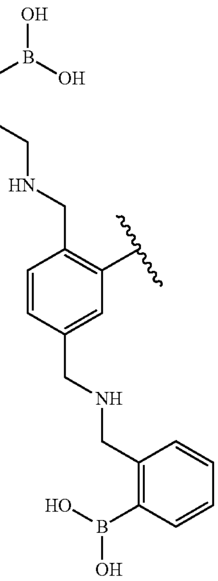 .

Clause 8. The hydrogel of any one of clauses 1-7, wherein

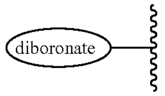

has an equilibrium constant ($K_{eq}$) for binding glucose of at least 350 $M^{-1}$.

Clause 9. The hydrogel of any one of clauses 1-8, wherein

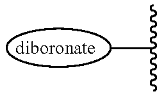

has an equilibrium constant ($K_{eq}$) for binding glucose of at least 1000 $M^{-1}$.

Clause 10. The hydrogel of any one of clauses 1-9, wherein

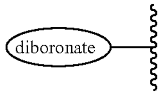

has an equilibrium constant ($K_{eq}$) for binding glucose that is at least 20 times greater than equilibrium constant of

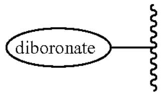

for binding lactate.

Clause 11. The hydrogel of any one of clauses 1-10, wherein

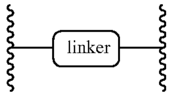

comprises:

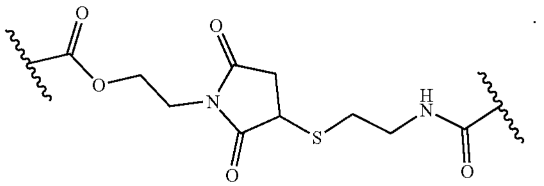

.

Clause 12. The hydrogel of any one of clauses 1-11, wherein

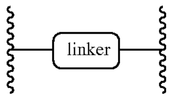

comprises:

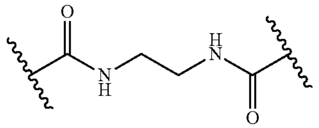

.

Clause 13. The hydrogel of any one of clauses 1-12, wherein

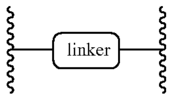

comprises:

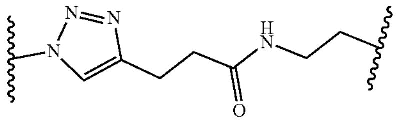

.

Clause 14. The hydrogel of any one of clauses 1-13, wherein

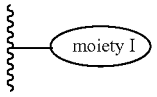

comprises a branched polymer.

Clause 15. The hydrogel of clause 14, wherein the branched polymer comprises a polyalkylene glycol.

Clause 16. The hydrogel of clause 15, wherein the polyalkylene glycol comprises polyethylene glycol.

Clause 17. The hydrogel of clause 14, wherein the branched polymer is a four-armed polymer.

Clause 18. The hydrogel of any one of clauses 1-17, wherein the diboronate compound of formula (I) comprises:

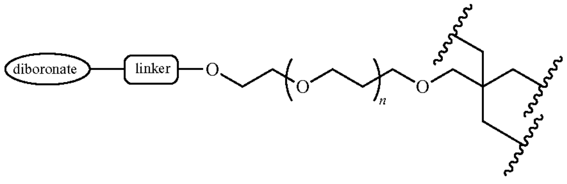

, wherein n is 2 to 250.

Clause 19. The hydrogel of any one of clauses 1-18, wherein

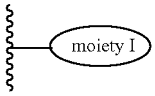

comprises a dendrimer.

Clause 20. The hydrogel of clause 19, wherein the dendrimer is a polyamidoamine dendrimer.

Clause 21. The hydrogel of any one of clauses 1-21, wherein

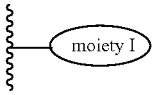

comprises a linear polymer.

Clause 22. The hydrogel of clause 21, wherein the linear polymer comprises a polysaccharide.

Clause 23. The hydrogel of clause 22, wherein the polysaccharide comprises hyaluronic acid.

Clause 24. The hydrogel of any one of clauses 1-23, wherein the molar ratio of the diboronate compound of formula (I) to the diol compound of formula (II) is 1:1.

Clause 25. The hydrogel of any one of clauses 1-24, wherein

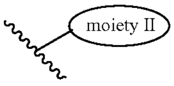

comprises a branched polymer.

Clause 26. The hydrogel of any one of clauses 1-25, wherein the branched polymer is a four-armed or an eight-armed polymer.

Clause 27. The hydrogel of any one of clauses 1-26, wherein the branched polymer comprises polyethylene glycol.

Clause 28. The hydrogel of any one of clauses 1-27, wherein the diol compound of formula (II) comprises:

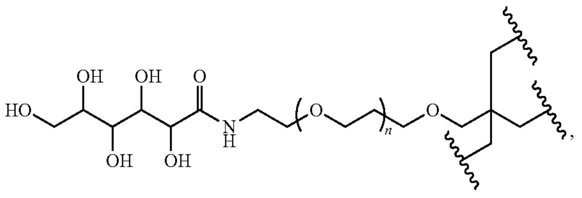

wherein n is 2 to 250.

Clause 29. The hydrogel of any one of clauses 1-28, wherein

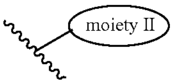

comprises a dendrimer.

Clause 30. The hydrogel of clause 29, wherein the dendrimer is a polyamidoamine dendrimer.

Clause 31. The hydrogel of any one of clauses 1-30, wherein

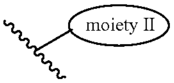

comprises a linear polymer.

Clause 32. A pharmaceutical composition comprising insulin encapsulated within the hydrogel of any one of clauses 1-31.

Clause 33. A method of delivering insulin to a subject in need thereof, the method comprising: administering a pharmaceutical composition to a subject in need thereof, the pharmaceutical composition comprising insulin encapsulated within a hydrogel, the hydrogel comprising:

(i) a diboronate compound of formula (I):

(I)

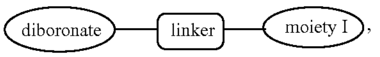

wherein:

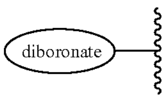 is 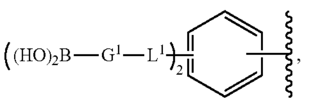

wherein:

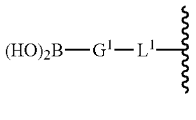 is 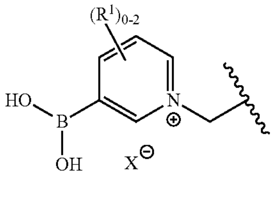 or

-continued

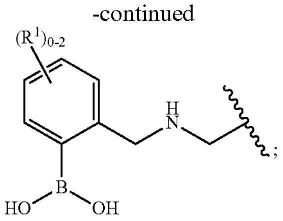

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$; and $X^{\ominus}$ is an anion having a net charge of −1;

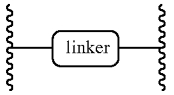

is a linking moiety; and

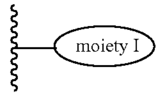

is a first moiety comprising a hydrophilic polymer, a hyperbranched macromolecule, or a combination thereof; and (ii) a diol compound of formula (II):

(II)

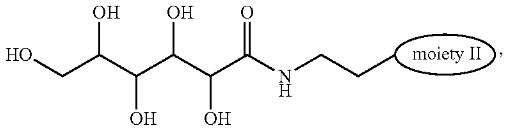

wherein:

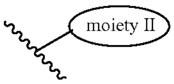

is a second moiety comprising a hydrophilic polymer, a hyperbranched macromolecule, or a combination thereof;

wherein the diboronate compound of formula (I) and the diol compound of formula (II) form crosslinks by dynamic-covalent bonds.

Clause 34. The method of clause 33, wherein the subject in need thereof has diabetes.

Clause 35. The method of clause 33 or 34, wherein the insulin is administered to the subject at 0.05-10 international units (IU)/kg.

Clause 36. The method of any one of clauses 33-35, wherein following administration of the pharmaceutical composition, the subject has blood glucose levels of about 60-110 mg/dL.

Clause 37. Use of the hydrogels of any one of clauses 1-31, the pharmaceutical composition of clause 32, or the methods of any one of clauses 33-36 for delivering insulin to a subject in need thereof.

EXAMPLES

Example 1

All purchased chemicals were used directly as received unless otherwise stated. All reactions were performed under an inert atmosphere with dry solvents in anhydrous conditions.

Dry tetrahydrofuran (THF), chloroform, N,N'-dimethylformamide (DMF), and methylene chloride (DCM) were purchased from VWR in sure-seal bottles. N-bromosuccinimide (NBS); Oxalyl chloride, 2,5-dimethylbenzoic acid, N-(2-hydroxyethyl)maleimide, 3-pyridylboronic acid, 2-(bromomethyl)benzoic acid, 3-(bromomethyl)benzoic acid, hydroxybenzotriazole monohydrate (HOBt) were purchased from VWR. 4-Arm-PEG-NH2 (4aPEG-NH2) was purchased from Laysan Bio, Inc. 4-Arm-PEG-SH (4aPEG-SH) was purchased from Biopharma PEG. 4-carboxy-3-fluorophenylboronic acid (FPBA) was purchased from Synthonix. Tetramethyluroniumhexaflurophosphate (HBTU) was purchased from Chem-Impex. Benzoyl peroxide was purchased from Alfa Aesar. Phosphate Buffered Saline (PBS) was purchased from VWR. Regenerated cellulose dialysis tubing (molecular weight cutoff (MWCO) of 3.5 kDa) was purchased from Spectrum Labs. D-(−)-fructose ($C_6H_{12}O_6$) was purchased from Sigma-Aldrich. D-Glucose (Dextrose) Anhydrous ($C_6H_{12}O_6$) was purchased from VWR. Fluorescein isothiocyanate isomer I (90%, pure) was purchased from Sigma-Aldrich. Recombinant Human Insulin AOF (Lot No. 1987626) from *Saccharomyces cerevisiae* was purchased from ThermoFisher. Sodium L-lactate ($C_3H_5NaO_3$) was purchased from Sigma-Aldrich. Streptozotocin (STZ, batch 0610596-17) was purchased from Cayman Chemical Company.

$^1$H NMR Spectroscopy

Spectra were recorded on Bruker 400 MHz instrument and calibrated using residue undeuterated solvent (($CDCl_3$: δH=7.26 ppm; $D_2O$: δH=4.79 ppm; $d_4$-MeOD: δH=3.34 ppm).

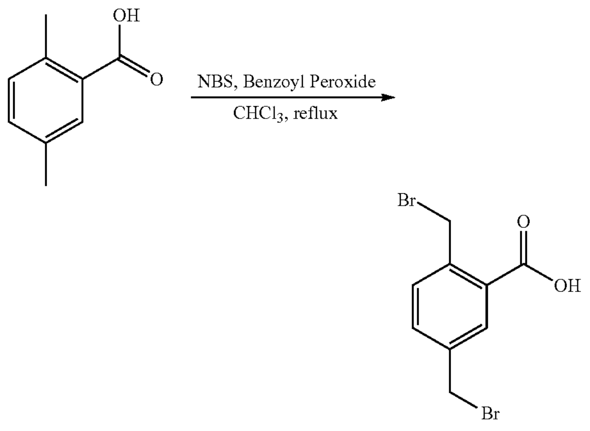

1

Synthesis of 2,5-bis(bromomethyl)benzoic acid (1)

A mixture of 2,5-dimethylbenzoic acid (3 g, 20 mmol), NBS (8.9 g, 50 mmol), and benzoyl peroxide (0.24 g, 1 mmol) were charged in an oven-dried 250 mL round-bottom flask and suspended with 90 mL chloroform. The mixture was heated to reflux for 4 h until a clear solution was observed. Then the mixture was cooled to ambient temperature and solvent was removed under reduced pressure. The residue was treated with 90 mL $Et_2O$, and the undissolved solids were filtered. The filtrate was then transferred to a separation funnel and washed with 90 mL water. The aqueous layer was then washed with 30 mL $Et_2O$. The organic layers were combined and washed with an aqueous solution of saturated NaCl (90 mL). The organic layer was then dried with $Na_2SO_4$, filtered, and the solvent was removed under reduced pressure. The residue was then recrystallized with hexaness and ethyl acetate at −20° C. After two days, the mixture was filtered, and the undissolved solids were then recrystallized with DCM and acetone at −20° C. The product was then filtered as a white solid with yields of 2 g (6 mmol, 30%). 1H NMR (400 MHz, Chloroform-d) δ 8.10 (d, J=2.0 Hz, 1H), 7.56 (dd, J=7.9, 2.1 Hz, 1H), 7.47 (d, J=7.9 Hz, 1H), 4.96 (d, J=2.2 Hz, 2H), 4.47 (s, 2H).

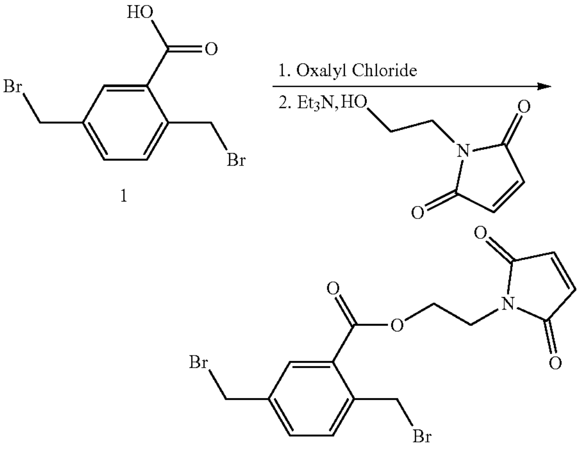

1

2

Synthesis of 2-(2,5-dioxo-2,5-dihydro-1H-pyrrol-1-yl)ethyl 2,5-bis(bromomethyl)benzoate (2)

An oven-dried 100 mL round-bottom flask was charged with compound 1 (1 g, 3.25 mmol), DMF (20 μL), and dissolved with 15 mL mixed solvent of THF:DCM (1:4). The mixture was then stirred at 0° C. for 10 min before the dropwise addition of oxalyl chloride (1.3 mL, 16.2 mmol). After the addition, the mixture was allowed to stir at ambient temperature for 90 min and the solvent was then removed under reduced pressure. The residue was diluted with 20 mL DCM, transferred to an addition funnel, and added to a mixture of N-(2-hydroxyethyl)maleimide (0.56 g, 4 mmol), triethylamine (0.58 mL, 4 mmol) and DCM (20 mL) at 0° C. After addition, the mixture was stirred at 0° C. for another 5 min before warming to ambient temperature. After 2 h, the mixture was transferred to a separation funnel and washed with 1 N HCl (25 mL). The aqueous layer was washed with DCM (20 mL). The organic layer was then combined and washed with water (25 mL) and an aqueous solution of saturated NaCl (25 mL) and dried over $Na_2SO_4$. The mixture was filtered, and the solvent was removed under reduced pressure. Then the residue was loaded on the column eluting with hexaness and ethyl acetate to obtain the product as white solids with yields of 0.86 g (2 mmol, 62%). $^1$H NMR (400 MHz, Chloroform-d) δ 7.96 (s, 1H), 7.57-7.41 (m, 2H), 6.74 (d, J=0.8 Hz, 2H), 5.00 (d, J=2.9 Hz, 1H), 4.91 (s, 1H), 4.55-4.42 (m, 4H), 3.98 (dt, J=5.3, 2.6 Hz, 2H).

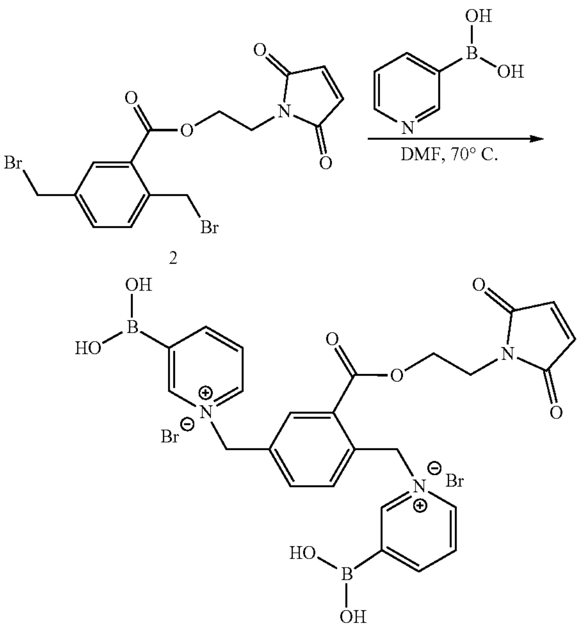

2
3

Synthesis of DiPBA-Maleimide (3)

A mixture of compound 2 (0.86 g, 2 mmol) and 3-pyridylboronic acid (0.52 g, 4.2 mmol) was charged to a 100 mL oven-dried round-bottom flask and diluted with 40 mL DMF. The mixture was stirred at 70° C. for 24 hours. Then the mixture was filtered, and the filtered solids was washed with THF and filtered to recover a white solid as the product with the yield of 1 g (1.5 mmol, 75%). $^1$H NMR (400 MHz, Methanol-$d_4$) δ 8.95 (d, J=6.2 Hz, 1H), 8.91 (s, 1H), 8.86 (s, 1H), 8.79 (d, J=8.6 Hz, 3H), 8.67 (dd, J=16.1, 7.7 Hz, 2H), 8.21 (s, 1H), 8.05 (q, J=6.3 Hz, 2H), 8.00-7.93 (m, 1H), 7.86 (d, J=7.9 Hz, 1H), 7.57 (d, J=7.9 Hz, 1H), 6.84 (s, 2H), 6.17 (s, 2H), 5.94 (s, 2H), 4.47-4.33 (m, 2H), 3.89 (t, J=4.9 Hz, 2H).

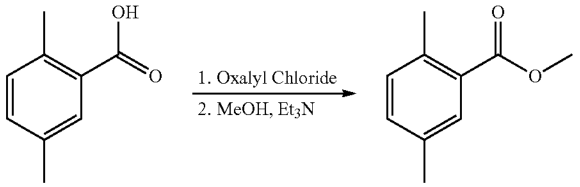

4

Synthesis of methyl 2,5-dimethylbenzoate (4)

An oven-dried 100 mL round bottom flask was charged with 2,5-dimethylbenzoic acid (1.5 g, 10 mmol), DMF (20 μL), and dissolved with 15 mL mixed solvent of THF:DCM (1:4). The mixture was then stirred at 0° C. for 10 min before the dropwise addition of oxalyl chloride (4 mL, 50 mmol). After the addition, the mixture was allowed to stir at ambient temperature for 90 min and the solvent was then removed under reduced pressure. The residue was treated with MeOH (40 mL) and triethylamine (1.7 mL, 12 mmol) and stirred at 0° C. for another 5 min before warming to ambient temperature. After 16 h, the solvent was removed under reduced pressure and the residue was diluted with 40 mL DCM. The mixture was transferred to a separation funnel and washed with 1 N HCl (25 mL). The aqueous layer was washed with DCM (20 mL). The organic layer was then combined and washed with water (25 mL) and an aqueous solution of saturated NaCl (25 mL) and dried over $Na_2SO_4$. The mixture was then filtered, and the solvent was removed under reduced pressure. Then the residue was loaded on the column eluting with hexaness and ethyl acetate to obtain the product as a transparent oil with yields of 1.6 g (10 mmol, 100%). $^1$H NMR (400 MHz, Chloroform-d) δ 7.72 (d, J=1.9 Hz, 1H), 7.21 (dd, J=7.7, 1.9 Hz, 1H), 7.13 (d, J=7.7 Hz, 1H), 3.88 (s, 3H), 2.55 (s, 3H), 2.34 (s, 3H).

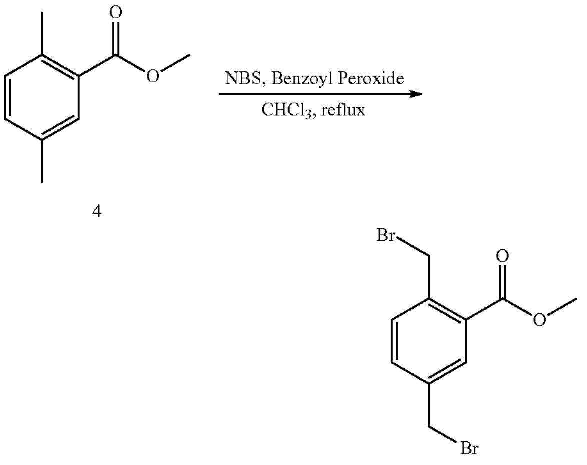

4
5

Synthesis of methyl 2,5-bis(bromomethyl)benzoate (5)

A mixture of compound 4 (1.6 g, 10 mmol), NBS (4.45 g, 20 mmol), and benzoyl peroxide (0.12 g, 0.5 mmol) was charged into an oven-dried 250 mL round-bottom flask and suspended with 45 mL chloroform. The mixture was heated to reflux for 4 h until a clear solution was observed. Then the mixture was cooled to ambient temperature and the solvent was removed under reduced pressure. The residue was treated with 90 mL $Et_2O$, and the undissolved solids were filtered. The filtrate was then transferred to a separation funnel and washed with the aqueous solution of saturated $NaHCO_3$ (45 mL). The aqueous layer was then washed with 15 mL $Et_2O$. The organic layers were combined and washed with an aqueous solution of saturated NaCl (45 mL). The organic layer was then dried with $Na_2SO_4$, filtered, and the solvent was removed under reduced pressure. The residue was then loaded on the column, eluting with hexaness and ethyl acetate to obtain the target product as white solids with a yield of 1.48 g (4.6 mmol, 46%). $^1$H NMR (400 MHz, Chloroform-d) δ 8.00 (d, J=2.0 Hz, 1H), 7.53 (dd, J=7.9, 2.0 Hz, 1H), 7.45 (d, J=7.9 Hz, 1H), 4.94 (s, 2H), 4.48 (s, 2H), 3.96 (s, 3H).

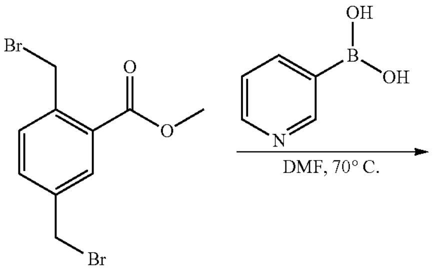

5

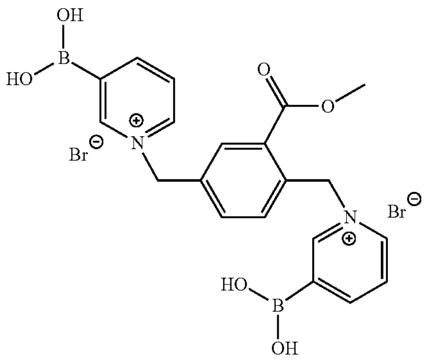

6

Synthesis of DiPBA$_{sm}$ (6)

A mixture of compound 5 (0.24 g, 0.74 mmol) and 3-pyridylboronic acid (0.19 g, 1.5 mmol) was charged to a 50 mL oven-dried round-bottom flask and diluted with 10 mL DMF. The mixture was then stirred at 70° C. for 24 h. Then the mixture was filtered and the filtered solid was washed with THF to recover a white solid as the product with the yield of 0.3 g (0.53 mmol, 70%). $^1$H NMR (400 MHz, Methanol-$d_4$) δ 8.96 (d, J=8.7 Hz, 2H), 8.93-8.78 (m, 3H), 8.70 (t, J=7.8 Hz, 2H), 8.29 (d, J=2.0 Hz, 1H), 8.01 (dt, J=20.8, 7.0 Hz, 2H), 7.84 (dd, J=8.0, 2.1 Hz, 1H), 7.61 (d, J=7.9 Hz, 1H), 6.18 (d, J=3.2 Hz, 2H), 5.96 (d, J=4.6 Hz, 2H), 3.89 (s, 3H).

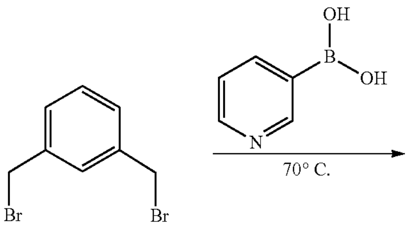

-continued

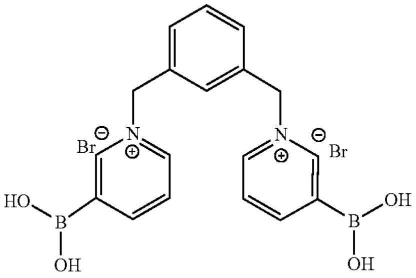

DiPBA1$_{sm}$

Synthesis of DiPBA1$_{sm}$

A mixture of 1,3-bis(bromomethyl)benzene (0.5 g, 1.9 mmol) and 3-pyridylboronic acid (0.48 g, 3.9 mmol) was charged to a 50 mL oven-dried round-bottom flask and diluted with 20 mL DMF. The mixture was stirred at 70° C. for 24 hours. Then the mixture was filtered, and the filtered solids was washed with $Et_2O$ and filtered to recover a white solid as the product. $^1$H NMR (400 MHz, Methanol-d4) δ 8.90 (t, J=5.4 Hz, 4H), 8.78 (d, J=5.8 Hz, 2H), 8.71 (d, J=7.6 Hz, 2H), 8.00 (q, J=8.8, 8.0 Hz, 3H), 7.67-7.63 (m, 1H), 7.57 (d, J=1.6 Hz, 3H), 5.85 (s, 4H).

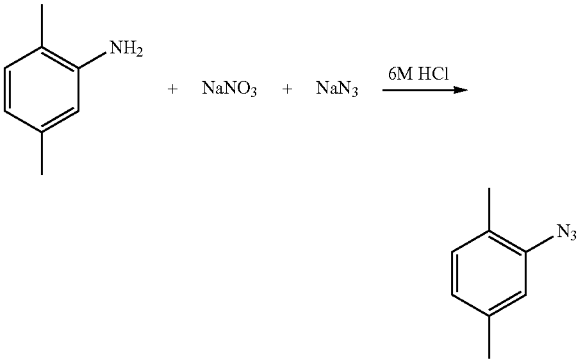

Synthesis of 2-azido-1,4-dimethylbenzene

In a 50 mL round bottom flask, 2,5-dimethylaniline (1.21 g, 0.01 mol) was charged and dissolved with 10 mL 6 M HCl. The mixture was kept stirred at 0° C. for 5 min before the dropwise addition of the $NaNO_3$ solution in water (1 g, 0.012 mol). After the addition, the mixture was kept at the same temperature and stirred for 30 mins. Then the reaction was treated with $NaN_3$ (0.04 mmol in 50 mL water) solution dropwise and was kept stirring for another hour. The mixture was then washed with ethyl acetate three times and the organic layer was combined, washed with water, and dried over $Na_2SO_4$. The mixture was filtered, concentrated, and loaded on the column eluting with hexaness to get the final product as light yellow oil with yield of 33% (0.49 g, 3.33 mmol). $^1$H NMR (400 MHz, DMSO-d6) δ 7.11 (d, J=7.6 Hz, 1H), 7.04 (s, 1H), 6.92-6.88 (m, 1H), 2.30 (s, 3H), 2.11 (s, 3H).

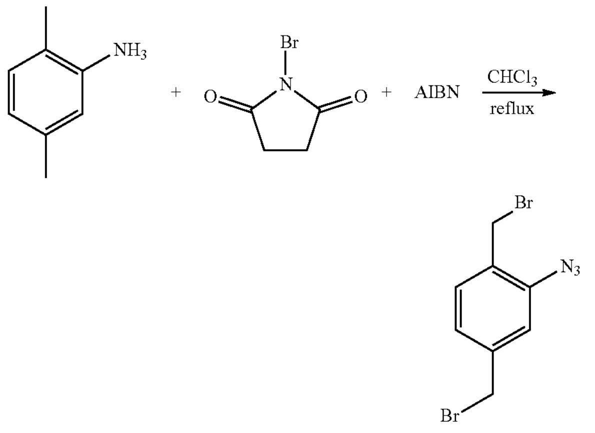

Synthesis of 2-azido-1,4-bis(bromomethyl)benzene

A mixture of 2-azido-1,4-dimethylbenzene (0.49 g, 3.33 mmol), NBS (1.27 g, 7.16 mmol), and azobisisobutyronitrile (AIBN, 0.1 g, 0.62 mmol) were charged in an oven-dried 250 mL round-bottom flask and suspended with 80 mL chloroform. The mixture was heated to reflux for 12 h and the solvent was removed. The residue was suspended in hexanes and the resulting solids were filtered. The hexanes solution was washed with sat. $NaHCO_3$, water, sat. NaCl, and dried over $Na_2SO_4$. The mixture was filtered, concentrated, and loaded on the column eluting with hexanes to provide the target product as a white solid with a 31% yield (0.18 g, 0.59 mmol). $^1H$ NMR (400 MHz, Chloroform-d) δ 7.35 (d, J=7.8 Hz, 1H), 7.18 (s, 1H), 7.14 (d, J=8.0 Hz, 1H), 4.46 (s, 2H), 4.45 (s, 2H).

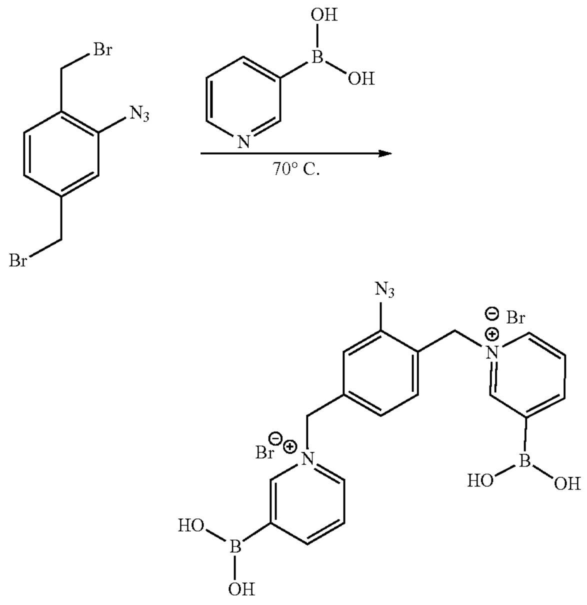

$DiPBA3_{sm}$

Synthesis of $DiPBA3_{sm}$

A mixture of 2-azido-1,4-bis(bromomethyl)benzene (0.18 g, 0.59 mmol) and 3-pyridylboronic acid (0.15 g, 1.2 mmol) was charged to a 50 mL oven-dried round-bottom flask and diluted with 20 mL DMF. The mixture was stirred at 70° C. for 24 hours. Then the mixture was filtered. The filtered solids were then washed with THF and filtered to recover the product as a white solid. $^1H$ NMR (400 MHz, Methanol-$d_4$) δ 8.89 (td, J=12.6, 5.5 Hz, 4H), 8.81-8.74 (m, 2H), 8.68 (t, J=8.9 Hz, 2H), 8.05-7.94 (m, 3H), 7.69 (d, J=7.9 Hz, 1H), 7.57 (d, J=1.7 Hz, 1H), 7.40-7.33 (m, 1H), 5.87 (s, 2H), 5.77 (s, 2H).

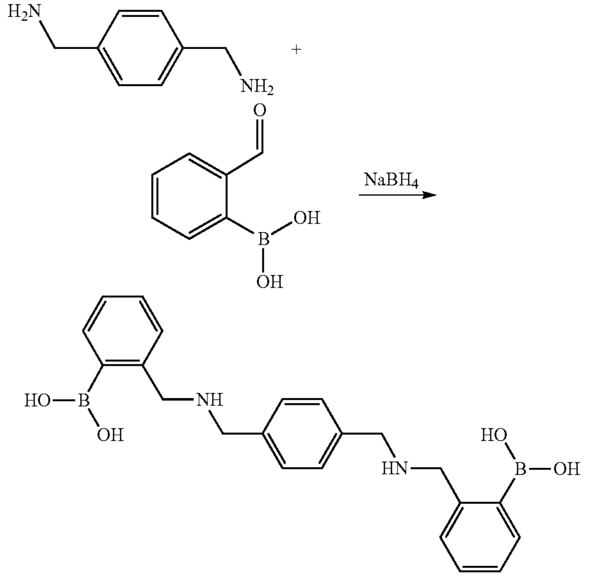

$DiAPBA_{sm}$

Synthesis of $DiAPBA_{sm}$

A mixture of 1,4-phenylenedimethanamine (0.28 g, 2.06 mmol) and (2-formylphenyl)boronic acid (0.64 g, 4.22 mmol) was charged to a 100 mL oven-dried round-bottom flask and diluted with 20 mL MeOH. The mixture was stirred overnight. Then the mixture was treated with $NaBH_4$ (0.12 g, 3.15 mmol) and stirred for another hour. The precipitate was filtered, washed with deionized (DI) water, and recovered as the target product. $^1H$ NMR (400 MHz, Deuterium Oxide/Deuterium Chloride) 6 7.73 (dd, J=7.3, 1.7 Hz, 2H), 7.52-7.35 (m, 10H), 4.31 (d, J=8.2 Hz, 8H).

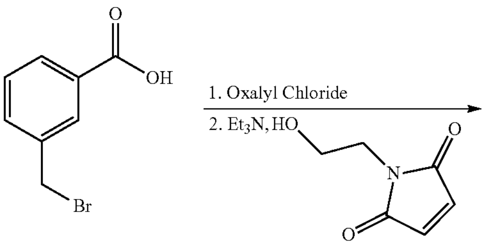

-continued

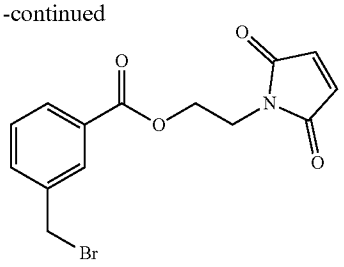

7

Synthesis of 2-(2,5-dioxo-2,5-dihydro-1H-pyrrol-1-yl)ethyl 3-(bromomethyl)benzoate (7)

An oven-dried 100 mL round-bottom flask was charged with 3-(bromomethyl)benzoic acid (1 g, 4.6 mmol) and DMF (20 μL), and dissolved with 20 mL THF. The mixture was then stirred at 0° C. for 10 min before the dropwise addition of oxalyl chloride (1.9 mL, 23 mmol). After the addition, the mixture was stirred at ambient temperature for 90 min and the solvent was then removed under reduced pressure. The residue was then diluted with 20 mL DCM and transferred to an addition funnel and added to a mixture of N-(2-hydroxyethyl)maleimide (0.78 g, 5.5 mmol), triethylamine (0.79 mL, 5.5 mmol) and DCM (20 mL) at 0° C. After the addition, the mixture was stirred at 0° C. for another 5 min before being warmed to ambient temperature. After 2 h, the mixture was transferred to a separation funnel and washed with 1 N HCl (25 mL). The aqueous layer was washed with DCM (20 mL). The organic layer was then combined and washed with water (25 mL) and an aqueous solution of saturated NaCl (25 mL) and dried over $Na_2SO_4$. The mixture was filtered, and the solvent was removed under reduced pressure. Then the residue was loaded to a silica column and eluted with hexanes and ethyl acetate to obtain the product as a white solid with yield of 1 g (2.9 mmol, 64%). $^1H$ NMR (400 MHz, Chloroform-d) δ 8.02 (t, J=1.8 Hz, 1H, Ar H), 7.93 (ddt, J=10.6, 7.7, 1.4 Hz, 1H, Ar H), 7.60 (dq, J=7.7, 1.6 Hz, 1H, Ar H), 7.43 (q, J=7.7 Hz, 1H, Ar H), 6.74 (d, J=0.7 Hz, 2H, CH═CH), 4.62 (s, 1H, Ar—$CH_2$—), 4.52 (s, 1H, Ar—$CH_2$—), 4.49-4.42 (m, 2H, —O—$CH_2$—), 4.00-3.92 (m, 2H, —$CH_2$—N—).

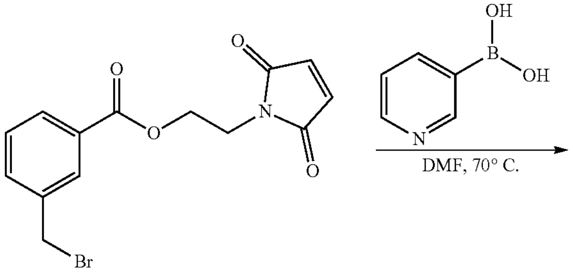

7

-continued

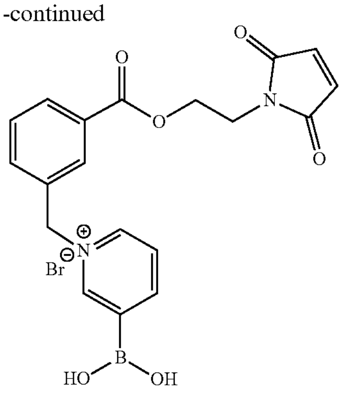

8

Synthesis of PyPBA-maleimide (8)

A mixture of compound 7 (1.04 g, 3.08 mmol) and 3-pyridylboronic acid (0.79 g, 6.46 mmol) was charged to a 100 mL oven-dried round-bottom flask and diluted with 40 mL DMF. The mixture was stirred at 70° C. for 24 h. Then the mixture was concentrated to a small volume and treated with 80 mL THF. The undissolved solids were filtered and washed with THF and recovered as product with a yield of 1 g (2.3 mmol, 75%). $^1H$ NMR (400 MHz, $D_2O$) δ 8.87 (s, 1H), 8.79 (s, 1H), 8.77-8.69 (m, 2H), 8.66 (d, J=7.3 Hz, 1H), 8.02-7.89 (m, 3H), 7.69 (d, J=7.8 Hz, 1H), 7.56 (t, J=7.8 Hz, 1H), 6.80 (s, 2H), 5.82 (s, 2H), 4.46 (t, J=5.0 Hz, 2H), 3.89 (t, J=5.0 Hz, 2H).

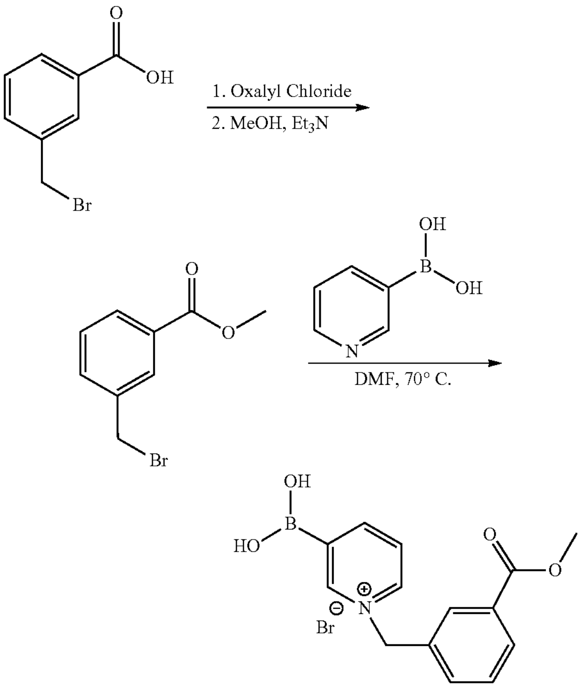

9

Synthesis of $PyPBA_{sm}$ (9)

An oven-dried 100 mL round bottom flask was charged with (0.5 g, 2.32 mmol) and DMF (20 μL) and dissolved with 15 mL mixed solvent of THF:DCM (1:4). The mixture was then stirred at 0° C. for 10 min before dropwise addition of oxalyl chloride (5 eq). After the addition, the mixture was allowed to stir at ambient temperature for 90 min and the solvent was then removed under reduced pressure. The residue was treated with MeOH (80 eq) and triethylamine (1.2 eq) and stirred at 0° C. for another 5 min before warming to ambient temperature. After 16 h, the solvent was removed under reduced pressure and the residue was diluted with 40 mL DCM. The mixture was then transferred to a separation funnel and washed with 1 N HCl (25 mL). The aqueous layer was washed with DCM (20 mL). The organic layer was then combined and washed with water (25 mL) and an aqueous solution of saturated NaCl (25 mL) and dried over $Na_2SO_4$. The mixture was then filtered, and the solvent was removed under reduced pressure and used directly for the next step. Methyl 3-(bromomethyl)benzoate was then mixed with 3-pyridylboronic acid (0.3 g, 2.44 mmol) in a 100 mL oven-dried round-bottom flask diluted with 20 mL DMF. The mixture was then stirred at 70° C. for 24 h. Then the mixture was concentrated to a small volume and treated with 40 mL THF. The undissolved solid was filtered and washed with THF and recovered as the product with a yield of 0.56 g (1.6 mmol, 70%). $^1$H NMR (400 MHz, Methanol-$d_4$) δ 8.96 (s, 1H), 8.93 (dd, J=6.1, 1.6 Hz, 1H), 8.88 (s, 1H), 8.79 (d, J=5.8 Hz, 1H), 8.74 (d, J=7.7 Hz, 1H), 8.69 (d, J=7.6 Hz, 1H), 8.16-8.09 (m, 2H), 8.01 (ddd, J=10.3, 7.7, 6.1 Hz, 2H), 7.76 (dt, J=7.9, 1.4 Hz, 1H), 7.62 (t, J=7.7 Hz, 1H), 5.91 (s, 2H), 3.94 (s, 3H). 1H NMR (400 MHz, Methanol-$d_4$) δ 8.96-8.86 (m, 2H), 8.77 (dd, J=19.3, 6.8 Hz, 1H), 8.69 (d, J=7.6 Hz, 1H), 8.16-8.09 (m, 2H), 8.01 (ddd, J=10.3, 7.7, 6.1 Hz, 2H), 7.76 (dt, J=7.9, 1.4 Hz, 1H), 7.62 (t, J=7.7 Hz, 1H), 5.91 (s, 2H), 3.94 (s, 3H).

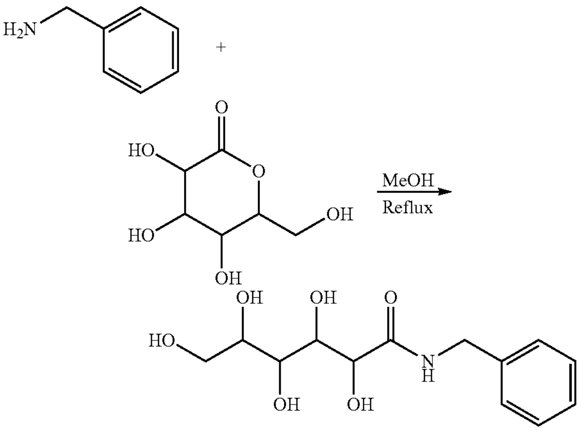

10

Synthesis of $Diol_{sm}$ (10)

Benzoyl amine (1.02 mL, 9.3 mmol) and D-gluconolactone (1.51 g, 8.8 mmol) were charged to a 50 mL oven-dried round-bottom flask and diluted with 10 mL MeOH. The mixture was then heated to reflux and stirred for 3 h. The solvent was removed under reduced pressure and the residue was recrystallized with EtOH to obtain the target product as a white solid with the yield of 2 g (7 mmol, 80%). $^1$H NMR (400 MHz, $D_2O$) δ 7.32-7.19 (m, 5H), 4.34 (d, J=1.7 Hz, 2H), 4.24 (d, J=3.7 Hz, 1H), 3.98 (t, J=3.2 Hz, 1H), 3.68 (dd, J=11.5, 2.3 Hz, 1H), 3.62 (dd, J=5.6, 2.5 Hz, 2H), 3.55-3.47 (m, 1H).

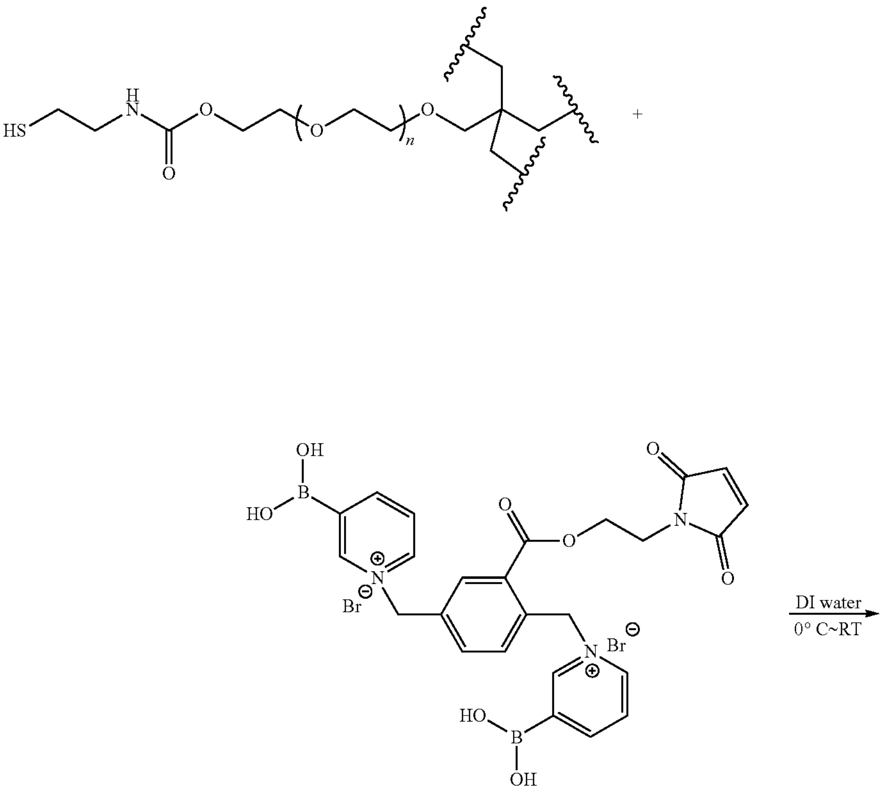

3

-continued

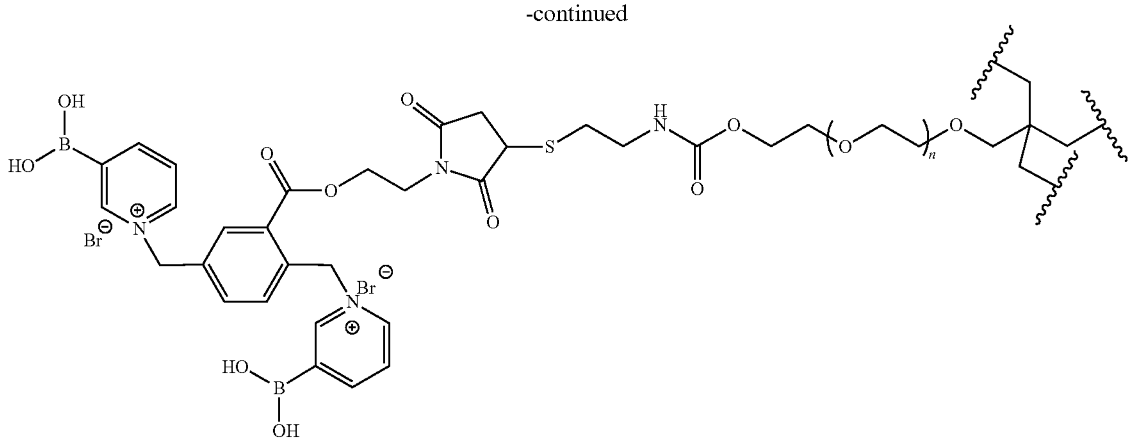

11

Synthesis of 4aPEG-DiPBA (11)

In a 50 mL oven-dried round-bottom flask, compound 3 (162 mg, 0.24 mmol) was diluted with 10 mL DI water and stirred at 0° C. A mixture of 4aPEG-thiol (0.4 g, 0.04 mmol) and DI water (10 mL) was prepared in an addition funnel and added dropwise to the solution of compound 3. After the addition, the mixture was warmed to ambient temperature and stirred for 6 h. The mixture was then dialyzed against DI water (MWCO of 3,500) for 8 h, and then lyophilized. $^{1}$H NMR (500 MHz, $D_2O$) δ 8.65 (s, 1H), 8.56 (d, J=6.3 Hz, 1H), 8.52 (s, 1H), 8.48 (dd, J=15.3, 7.6 Hz, 2H), 8.40 (d, J=6.3 Hz, 1H), 8.02 (s, 1H), 7.83-7.78 (m, 1H), 7.76-7.72 (m, 1H), 7.64 (d, J=7.9 Hz, 1H), 7.32 (d, J=7.9 Hz, 1H), 5.96 (d, J=3.1 Hz, 2H), 5.73 (s, 2H), 4.41 (d, J=9.2 Hz, 1H), 4.31 (d, J=11.8 Hz, 1H), 4.05 (s, 2H), 3.87 (d, J=8.7 Hz, 2H), 3.59 (s, 219H), 3.15 (dd, J=19.1, 9.0 Hz, 1H), 3.01 (dd, J=13.5, 6.8 Hz, 2H), 2.61-2.54 (m, 1H), 2.49 (s, 1H), 2.38 (s, 1H).

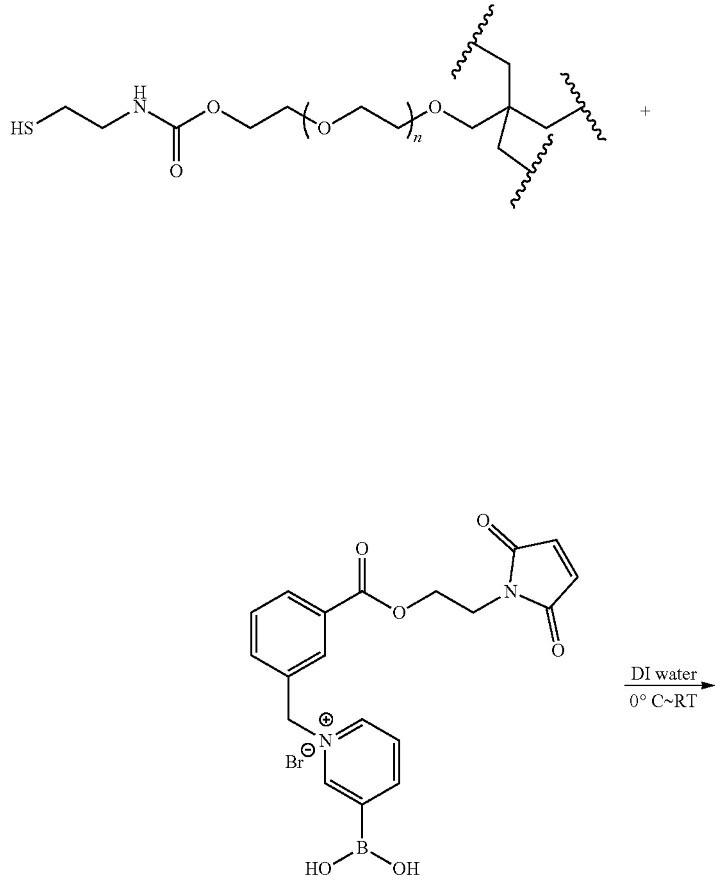

8

-continued

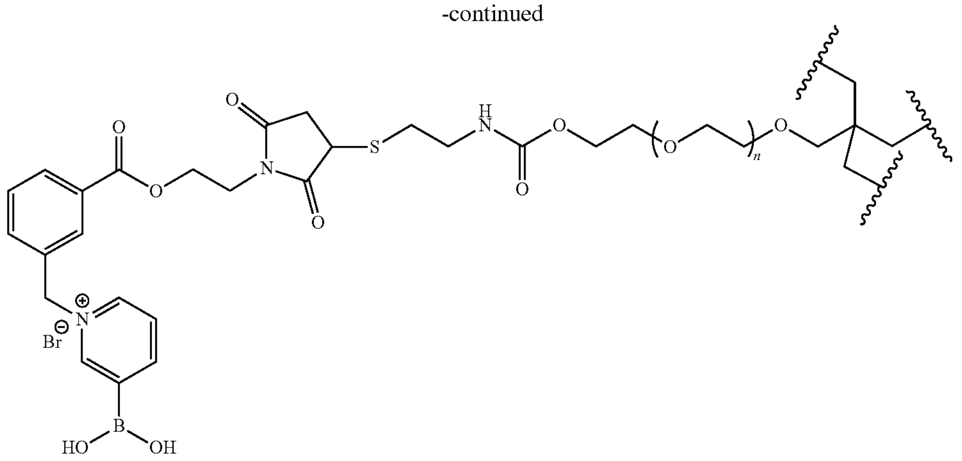

12

Synthesis of 4aPEG-PyPBA (12)

In a 50 mL oven-dried round-bottom flask, compound 8 (111 mg, 0.24 mmol) was diluted with 10 mL DI water and stirred at 0° C. A mixture of 4aPEG-thiol (0.4 g, 0.04 mmol) and DI water (10 mL) was prepared in an addition funnel and added dropwise to the solution of compound 8. After addition, the mixture was warmed to ambient temperature and stirred for 6 h. The mixture was then dialyzed against DI water (MWCO of 3,500) for 8 h, and then lyophilized. $^1$H NMR (400 MHz, $D_2O$) δ 8.75 (s, 1H), 8.58 (dd, J=29.4, 7.0 Hz, 2H), 7.91 (d, J=9.1 Hz, 2H), 7.84 (t, J=6.8 Hz, 1H), 7.64 (d, J=7.9 Hz, 1H), 7.50 (t, J=7.7 Hz, 1H), 5.72 (s, 2H), 4.46 (s, 1H), 4.36 (d, J=11.9 Hz, 1H), 4.04 (s, 2H), 3.90 (dd, J=9.1, 3.8 Hz, 2H), 3.59 (s, 192H), 3.18 (dd, J=19.1, 9.0 Hz, 1H), 3.01 (d, J=5.7 Hz, 2H), 2.64-2.54 (m, 1H), 2.46-2.37 (m, 1H).

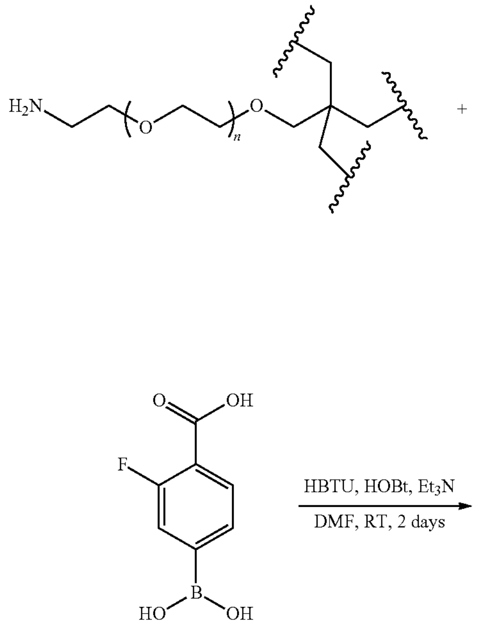

-continued

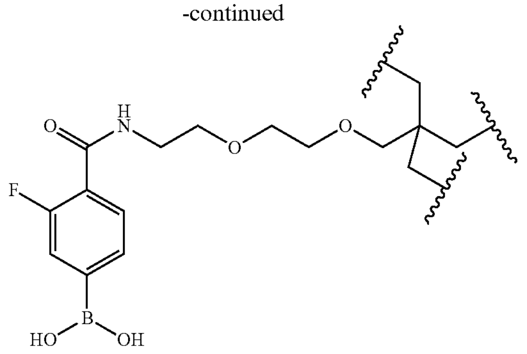

13

Synthesis of 4aPEG-FPBA (13)

A mixture of 4aPEG-$NH_2$ (10 kDa, 3 g, 3 mmol), 4-formylphenylboronic acid (FPBA, 0.33 g, 1.8 mmol), hydroxybenzotriazole (HOBt, 0.24 g, 1.8 mmol), and triethylamine (0.26 mL, 1.8 mmol) was added to a 100 mL oven-dried round-bottom flask and diluted with 25 mL DMF. The mixture was stirred for 5 min before the addition of (2-(1H-benzotriazol-1-yl)-1,1,3,3-tetramethyluronium hexafluorophosphate (HBTU, 0.68 g, 1.8 mmol). After the addition, the mixture was then stirred for 2 d and the solvent was removed under reduced pressure. The residue was then diluted with 20 mL MeOH and the mixture was dialyzed against MeOH for 24 h, followed by further dialysis against DI water for 2 d, and then lyophilized. $^1$H NMR (400 MHz, Chloroform-d) δ 8.00 (t, J=7.6 Hz, 1H), 7.71 (d, J=7.8 Hz, 1H), 7.58 (d, J=12.6 Hz, 1H), 6.66 (s, 1H), 3.65 (s, 211H).

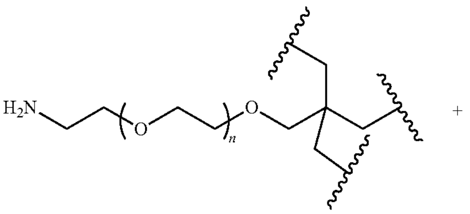

-continued

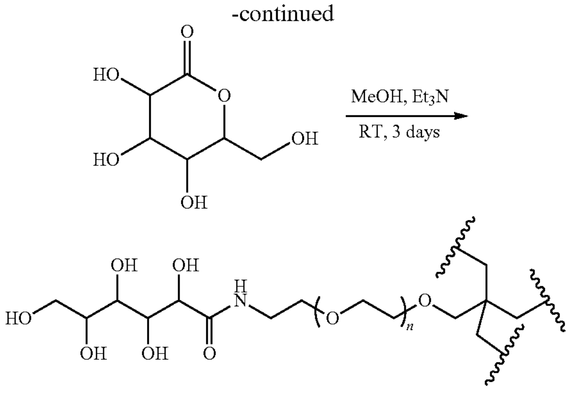

14

Synthesis of 4aPEG-Diol (14)

A mixture of 4aPEG-$NH_2$ (10 kDa, 3.0 g, 0.3 mmol), D-gluconolactone (0.3 g, 4.8 mmol), and triethylamine (0.7 mL, 4.8 mmol) was added to a 100 mL oven-dried round-bottom flask and diluted with 50 mL MeOH. The mixture was allowed to stir at ambient temperature for 3 days before being transferred to a dialysis tube (MWCO of 3,500) and dialyzed against MeOH for 24 hours, followed by further dialyzed against DI water for 24 hours, and lyophilized. $^1H$ NMR (400 MHz, 020) δ 4.29 (d, J=3.7 Hz, 1H), 4.05 (t, J=3.2 Hz, 1H), 3.67 (s, 193H), 3.51-3.38 (m, 5H).

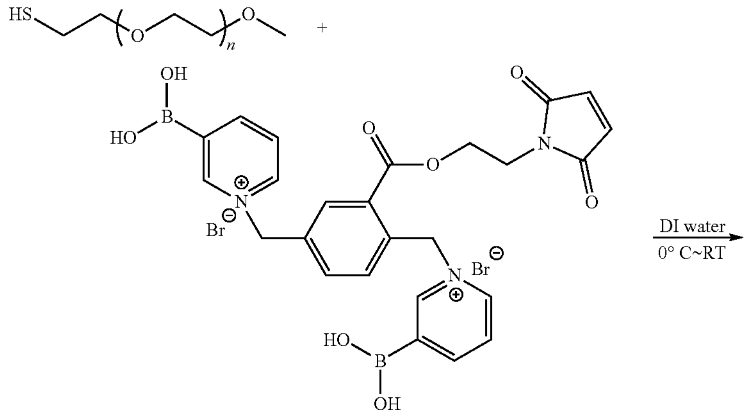

3

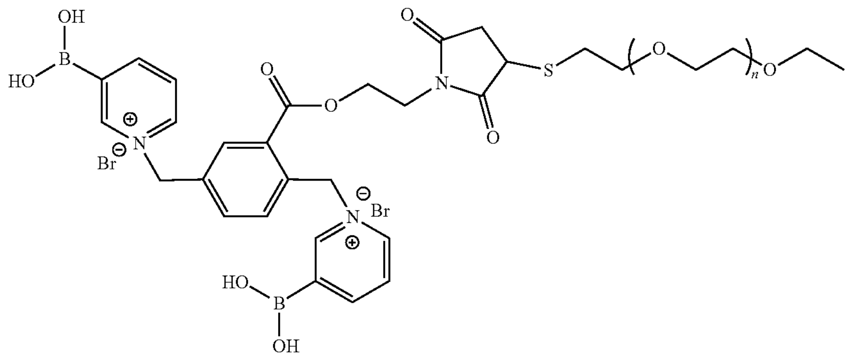

15

Synthesis of mPEG-DiPBA (15)

In a 50 mL oven-dried round-bottom flask, compound 3 (81 mg, 0.12 mmol) was diluted with 10 mL DI water and stirred at 0° C. A mixture of mPEG-thiol (5k Da, 0.5 g, 0.1 mmol) and DI water (10 mL) was prepared in an addition funnel and added dropwise to the solution of compound 3. After the addition, the mixture was warmed to ambient temperature and stirred for 6 h. The mixture was then dialyzed against DI water (MWCO of 3,500) for 8 h, and then lyophilized. $^{1}H$ NMR (400 MHz, $D_2O$) δ 8.71 (s, 1H), 8.67-8.48 (m, 4H), 8.45 (d, J=6.2 Hz, 1H), 8.11 (d, J=2.0 Hz, 1H), 7.91-7.84 (m, 1H), 7.84-7.78 (m, 1H), 7.76-7.68 (m, 1H), 7.39 (d, J=8.0 Hz, 1H), 6.04 (s, 2H), 5.81 (s, 2H), 3.67 (s, 405H), 3.35 (s, 3H), 2.82 (dt, J=12.3, 6.0 Hz, 1H), 2.62 (ddd, J=18.0, 12.2, 4.9 Hz, 2H).

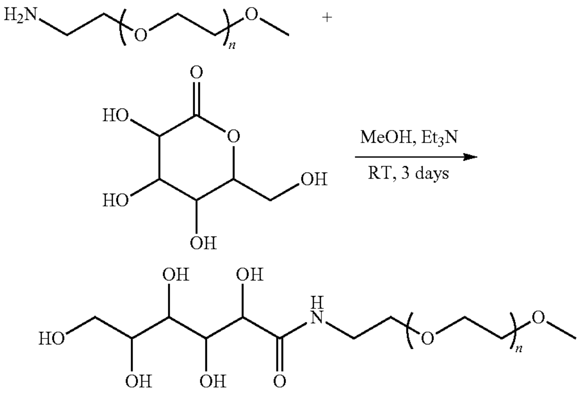

16

Synthesis of mPEG-Diol (16)

A mixture of mPEG-$NH_2$ (5 kDa, 0.5 g, 0.1 mmol), d-gluconolactone (71.2 mg, 0.4 mmol), and triethylamine (58 μL, 0.4 mmol) was added to a 50 mL oven-dried round-bottom flask and diluted with 10 mL MeOH. The mixture was allowed to stir at ambient temperature for 3 days before being transferred to a dialysis tube (MWCO of 3,500) and dialyzed against MeOH for 24 hours, followed by further dialyzed against DI water for 24 hours, and lyophilized. $^{1}H$ NMR (400 MHz, $D_2O$) δ 4.29 (d, J=3.6 Hz, 1H), 4.05 (s, 1H), 3.67 (s, 382H), 3.35 (s, 3H).

-continued

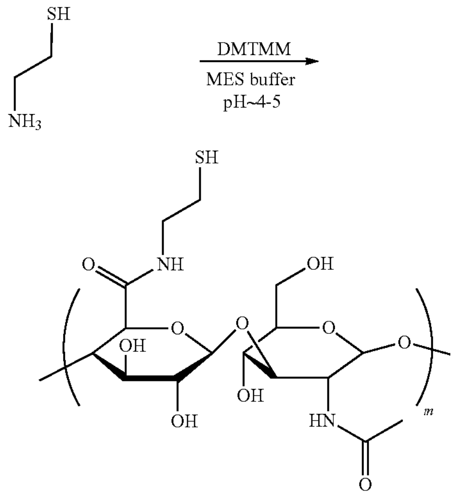

HA-thiol

Synthesis of HA-thiol

Hyaluronic acid (HA, 60 kDa, 0.23 g, 0.004 mmol) and 4-(4,6-dimethoxy-1,3,5-triazin-2-yl)-4-methyl-morpholinium chloride (DMTMM, 0.14 g, 0.5 mmol) were diluted with 20 mL 2-(N-morpholino)ethanesulfonic acid (MES) buffer (pH=~4-5) and stirred at ambient temperature until fully dissolved. Then 2-aminoethane-1-thiol (38 mg, 0.5 mmol) was added, and the mixture was kept stirring for 2 days before being transferred to a dialysis tube (MWCO of 10,000) and dialyzed against 10 wt % NaCl for 1 day, followed by further dialysis in water for 2 days, and lyophilized. $^{1}H$ NMR (400 MHz, $D_2O$) δ 4.45-4.40 (m, 2H), 3.87-3.11 (m, 14H), 1.89 (s, 3H).

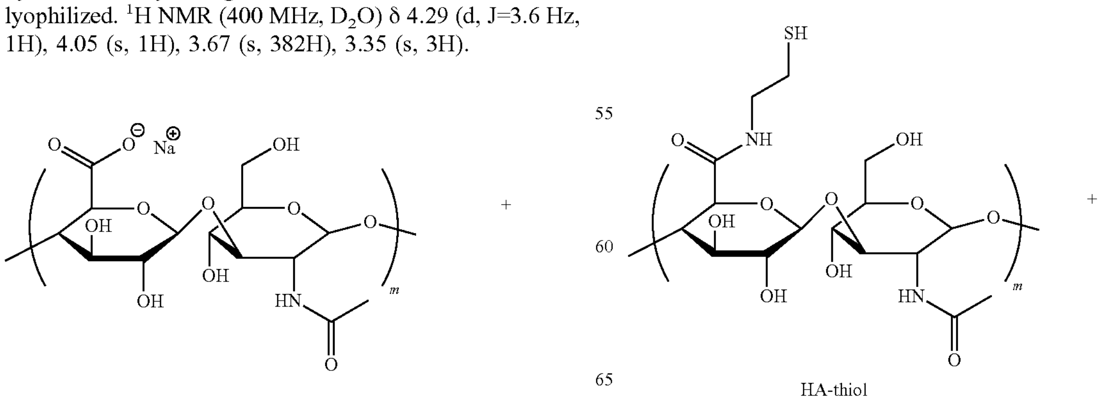

HA-thiol

-continued

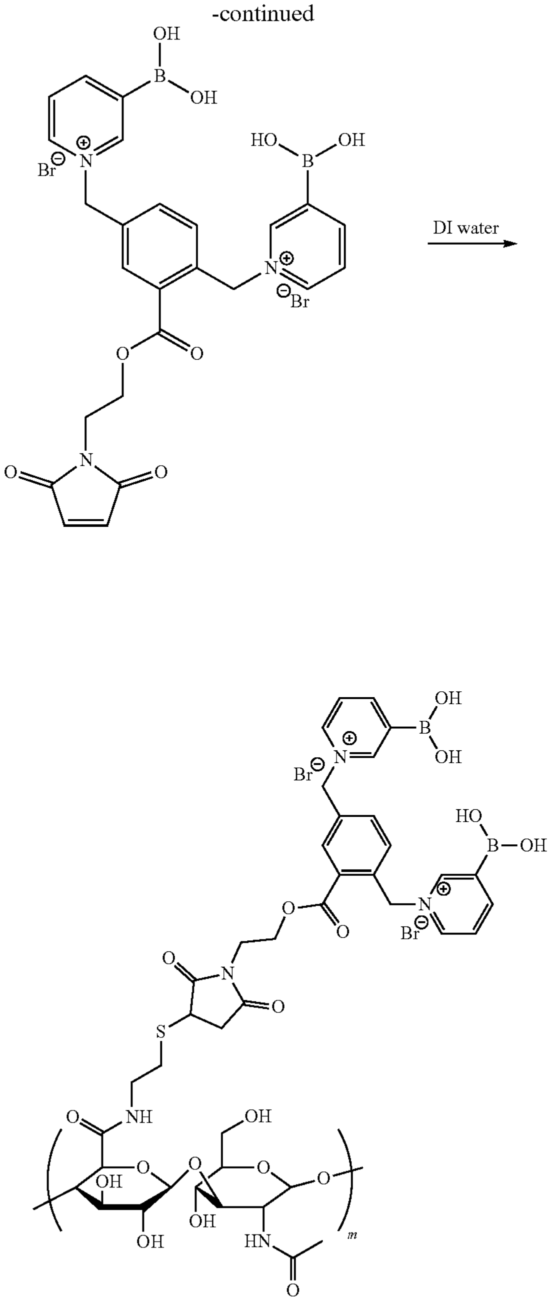

HA-DiPBA 1

Synthesis of HA-DiPBA 1

HA-thiol (60 kDa, 0.3 g) and compound 3 (0.34 g, 0.5 mmol) were diluted with 40 mL DI water and stirred at ambient temperature 1 day before being transferred to a dialysis tube (MWCO of 10,000), dialyzed against water for 24 hrs, and lyophilized. $^1H$ NMR (400 MHz, Deuterium Oxide) 0 8.74 (d, J=23.8 Hz, 2H), 8.56 (s, 3H), 7.90 (s, 1H), 7.81 (s, 1H), 7.64 (s, 2H), 7.40 (s, 2H), 5.94 (s, 2H), 5.75 (s, 2H), 4.38 (s, 2H), 3.93-3.09 (m, 20H), 1.79 (s, 3H). This protocol was suitable for HA MWs of 60 kDa, 500 kDa, and 700 kDa. The % of modification can be tuned ranging from 5%-25%. The subscript "m" may range from 130-1500.

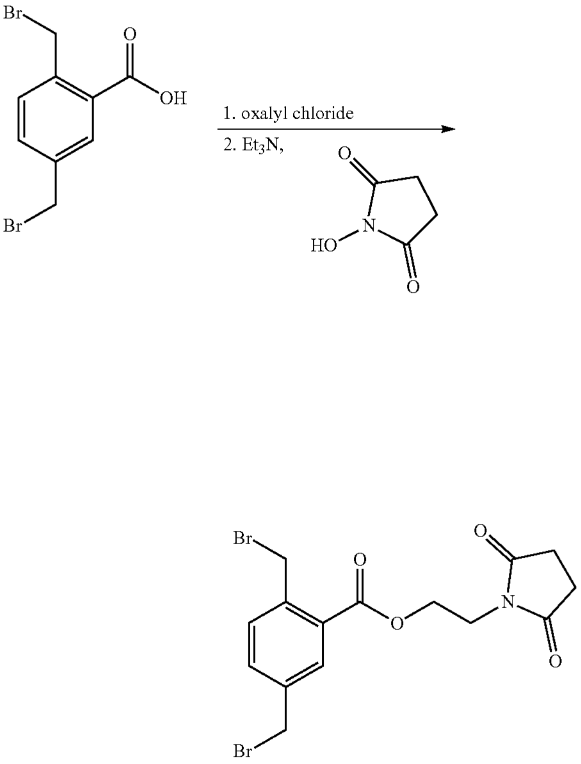

Synthesis of 2,5-dioxopyrrolidin-1-yl 2,5-bis(bromomethyl)benzoate

An oven-dried 100 mL round-bottom flask was charged with 2,5-bis(bromomethyl)benzoic acid (1 g, 3.25 mmol), DMF (20 μL), and dissolved with 15 mL mixed solvent of THF:DCM (1:4). The mixture was then stirred at 0° C. for 10 min before the dropwise addition of oxalyl chloride (1.3 mL, 16.2 mmol). After the addition, the mixture was allowed to stir for 90 min. The solvent was then removed under reduced pressure. The residue was diluted with 20 mL DCM, transferred to an addition funnel, and added to a mixture of 1-hydroxypyrrolidine-2,5-dione (0.46 g, 4 mmol), triethylamine (0.58 mL, 4 mmol) and DCM (20 mL) at 0° C. After addition, the mixture was stirred at 0° C. for another 5 min before warming to ambient temperature. After 2 h, the mixture was transferred to a separation funnel and washed with washed with water (25 mL) and sat. NaCl (25 mL) solution and dried over $Na_2SO_4$. The mixture was filtered, and the solvent was removed under reduced pressure and the residue was used directly for the next step.

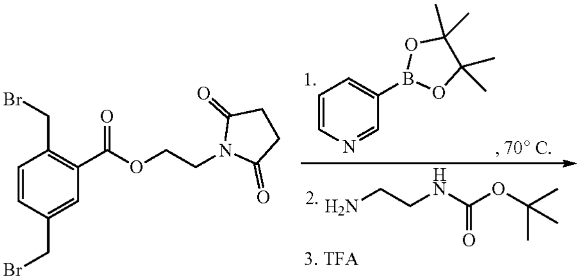

-continued

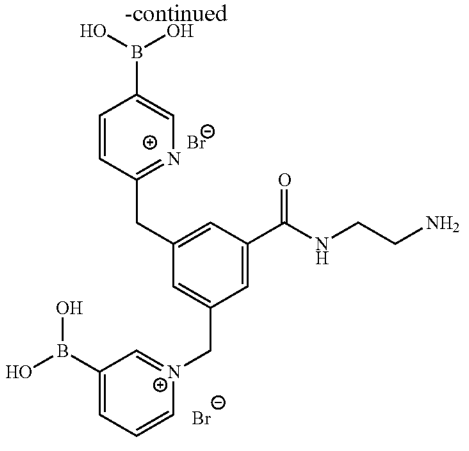

DiPBA-$NH_2$

Synthesis of DiPBA-$NH_2$

An oven-dried 100 mL round-bottom flask was charged with 2,5-dioxopyrrolidin-1-yl 2,5-bis(bromomethyl)benzoate (1.1 g, 2.8 mmol), 3-(4,4,5,5-tetramethyl-1,3,2-dioxaborolan-2-yl)pyridine (1.1 g, 5.5 mmol) and 40 mL DMF. The mixture was stirred at 70° C. for 16 hr before the mixture was cooled down to the ambient temperature. The mixture was then treated with tert-butyl (2-aminoethyl) carbamate (0.43 g, 2.8 mmol), and stirred for another 24 hr, and then the solvent was removed under vacuum. After that, 20 mL TFA was added to the residue and stirred for 2 hrs. TFA was then removed, and the residue was added to excess TFA. The precipitate was collected, washed with acetone and $Et_2O$ to provide the target product. $^1H$ NMR (400 MHz, $D_2O$) δ 8.83 (s, 1H), 8.76-8.68 (m, 2H), 8.65-8.57 (m, 3H), 7.88 (dt, J=16.9, 7.1 Hz, 2H), 7.65 (s, 1H), 7.57 (d, J=8.8 Hz, 1H), 7.50 (d, J=8.0 Hz, 1H), 5.84 (d, J=5.6 Hz, 2H), 5.77 (s, 2H), 3.44 (dt, J=12.3, 6.3 Hz, 2H), 3.05 (dt, J=12.5, 6.2 Hz, 2H).

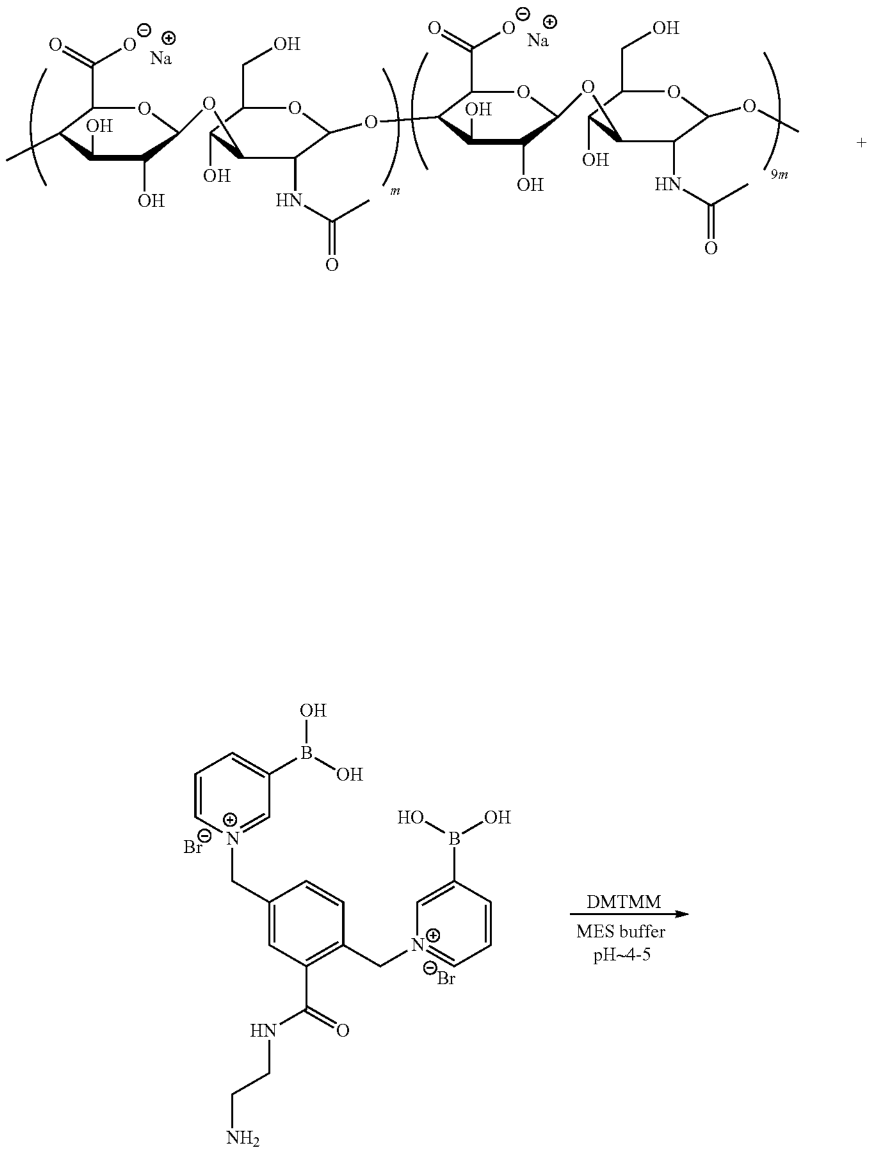

-continued

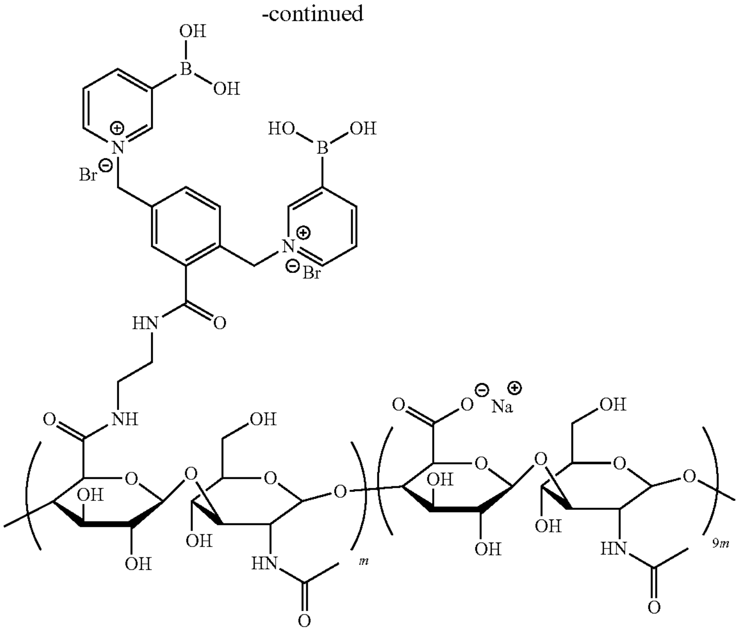

HA-DiPBA 2

Synthesis of HA-DiPBA 2

Hyaluronic acid (HA) (60 kDa, 0.23 g, 0.004 mmol) and 4-(4,6-dimethoxy-1,3,5-triazin-2-yl)-4-methyl-morpholinium chloride (DMTMM, 0.14 g, 0.5 mmol) were diluted with 20 mL 2-(N-morpholino)ethanesulfonic acid (MES) buffer (pH=~4-5) and stirred at ambient temperature until fully dissolved. Then DiPBA-$NH_2$ (35 mg, 0.05 mmol) was added, and the mixture was kept stirring for 5 days before being transferred to a dialysis tube (MWCO of 10,000) and dialyzed against 10 wt % NaCl for 1 day, followed by further dialysis in water for 2 days, and lyophilized. This protocol was also suitable for HA MWs of 500 kDa or 700 kDa. The % of modification can be tuned ranging from 5%-25%. The subscript “m” may range from 130-1500.

Example Polyetheyleneglycol (PEG)/Ornithine (Orni)-DiPBA

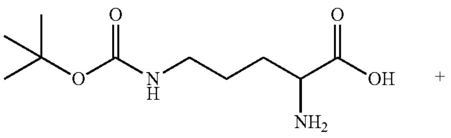

-continued

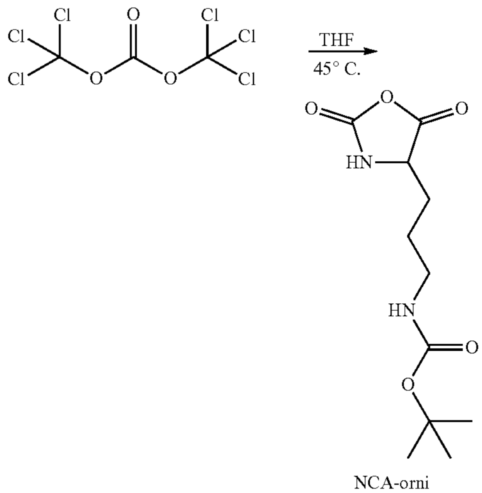

NCA-orni

Synthesis of NCA-Orni

2-Amino-5-((tert-butoxycarbonyl)amino)pentanoic acid (2.46 g, 10 mmol) was suspended in 38 mL of dry THF in a oven-dried round bottom flask and stirred at 45° C. before the treatment of triphosgene (1.48 g, 5 mmol) solution in THF (10 mL). The mixture was kept stirring at 45° C. for 45 min and centrifuged. The supernatant was collected and concentrated and the resulting solids were recrystallized from THF/hexanes at −20° C. to obtain the target product as a white solid. $^1$H NMR (400 MHz, DMSO-d6) δ 9.09 (s, 1H), 6.88 (t, J=5.8 Hz, 1H), 4.44 (td, J=5.5, 2.8 Hz, 1H), 2.92 (q, J=6.5 Hz, 2H), 1.77-1.68 (m, 1H), 1.65-1.56 (m, 1H), 1.43 (dt, J=17.6, 6.4 Hz, 2H), 1.37 (s, 9H).

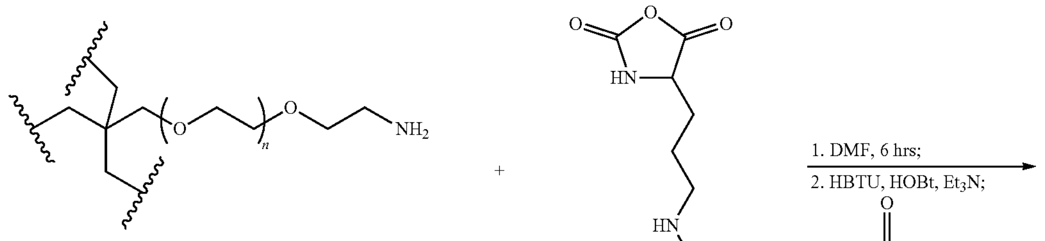

4aPEG-$NH_2$

NCA-orni

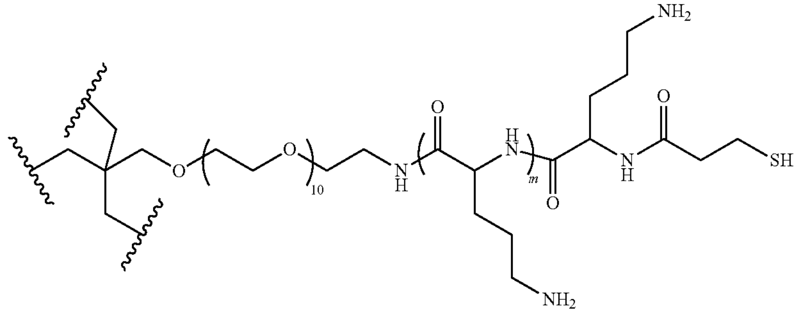

$4aPEG_{10}(Orni)_m$-SH

Synthesis of $4aPEG_{10}(Orni)_m$-SH

To an oven-dried 10 mL round bottom flask, NCA-Orni (1 g, 3.9 mmol) and DMF (8 mL) were added and stirred at ambient temperature. The solution was freeze-pump-thawed for 3 cycles, then 4aPEG-$NH_2$ (2 kDa, 48 mg, 0.024 mmol) was added. The mixture was kept at ambient temperature for 6 hr before exposed to the air. Then, HBTU (46 mg, 0.12 mmol), HOBt (16 mg, 0.12 mmol), 3-mercaptopropanoic acid (13 mg, 0.12 mmol), and $Et_3N$ (17 μL, 0.12 mmol) were added to the mixture and stirred for another 6 hr. The solution was then transferred to a dialysis tube (MWCO of 3,500) and dialyzed against MeOH (for 24 hr) and water (for 24 hr). The undissolved solids were collected by filtration. The collected solids were treated with TFA (50 mL) for 2 hr and concentrated to small volume. The residue was then diluted with 20 mL water and transferred to a dialysis tube (MWCO of 3,500) dialyzed in water for 24 hr, then lyophilized and used directly for the next step.

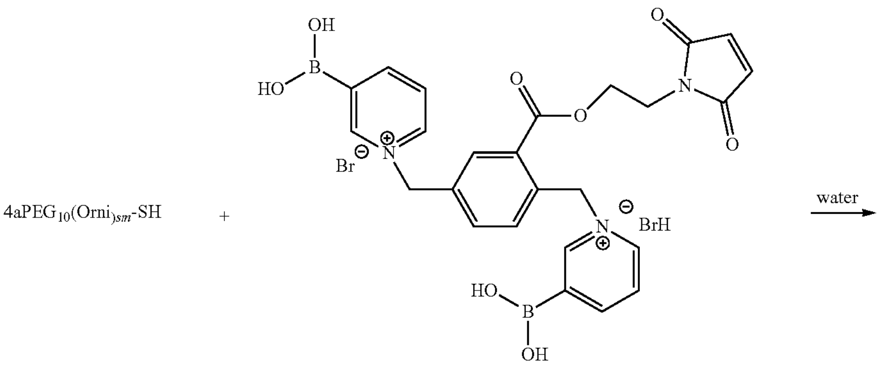

3

-continued

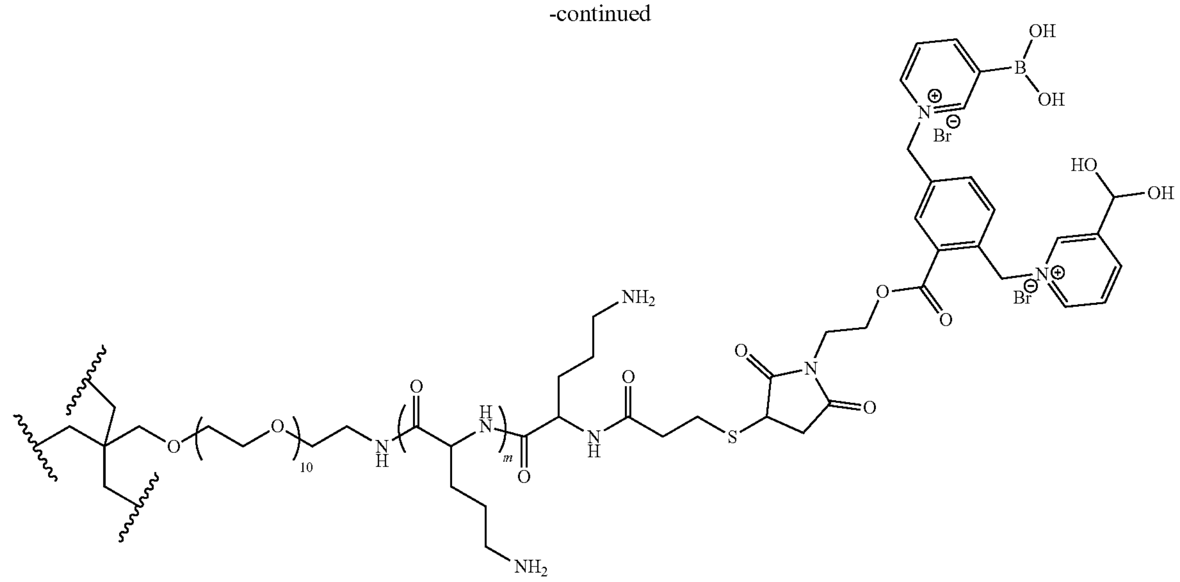

Synthesis of $4aPEG_{10}$(Orni)m-DiPBA $4aPEG_{10}$(Orni)m-SH (0.2 g, 0.017 mmol) and compound 3 (46 mg, 0.07 mmol) were diluted with 10 mL DI water and stirred at ambient temperature 1 day before being transferred to a dialysis tube (10,000 MWCO) and dialyzed against water for 24 hr, and lyophilized. $^1H$ NMR (400 MHz, $D_2O$) δ 8.67 (s, 6H), 8.60 (s, 4H), 8.54 (s, 9H), 8.51 (s, 8H), 8.41 (s, 5H), 7.82 (d, J=21.3 Hz, 13H), 7.67 (d, J=17.0 Hz, 5H), 7.33 (d, J=22.4 Hz, 4H), 6.04 (s, 8H), 5.81 (s, 8H), 4.31 (s, 108H), 3.68 (s, 181H), 3.00 (s, 210H), 1.74 (s, 413H).

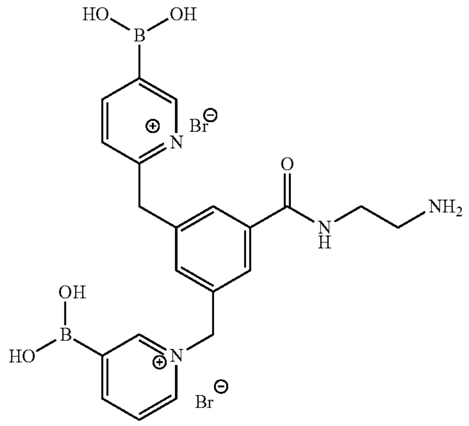

$DiPBA-NH_2$

+

-continued

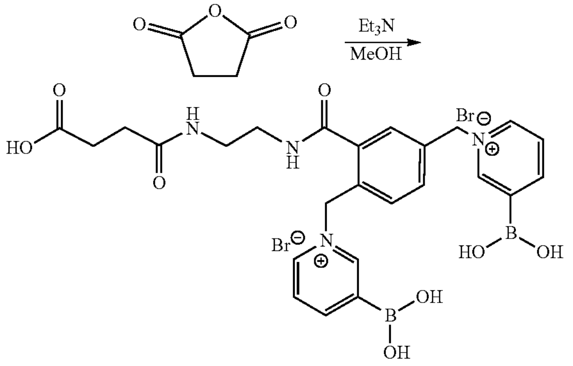

DiPBA-COOH

Synthesis of DiPBA-COOH $DiPBA-NH_2$ (0.5 g, 0.7 mmol), succinic anhydride (78 mg, 0.77 mmol), and $Et_3N$ (0.12 mL, 0.77 mmol) were charged to a 100 mL round bottom flask and diluted with 20 mL MeOH. The mixture was stirred at ambient temperature for 24 hr before concentrated to small column. The residue was added to large volume of $Et_2O$, and the precipitate was collected, washed with DCM and acetone and dried under vacuum as the target product. $^1H$ NMR (400 MHz, $D_2O$) δ 8.80 (s, 1H), 8.71 (d, J=6.2 Hz, 1H), 8.61 (d, J=7.0 Hz, 4H), 7.91 (q, J=7.6 Hz, 2H), 7.67 (d, J=8.0 Hz, 1H), 7.58 (d, J=7.8 Hz, 1H), 7.48 (s, 1H), 5.87 (s, 2H), 5.82 (s, 2H), 3.27 (dd, J=18.7, 6.1 Hz, 4H), 2.50 (t, J=6.5 Hz, 2H), 2.41 (t, J=6.4 Hz, 2H).

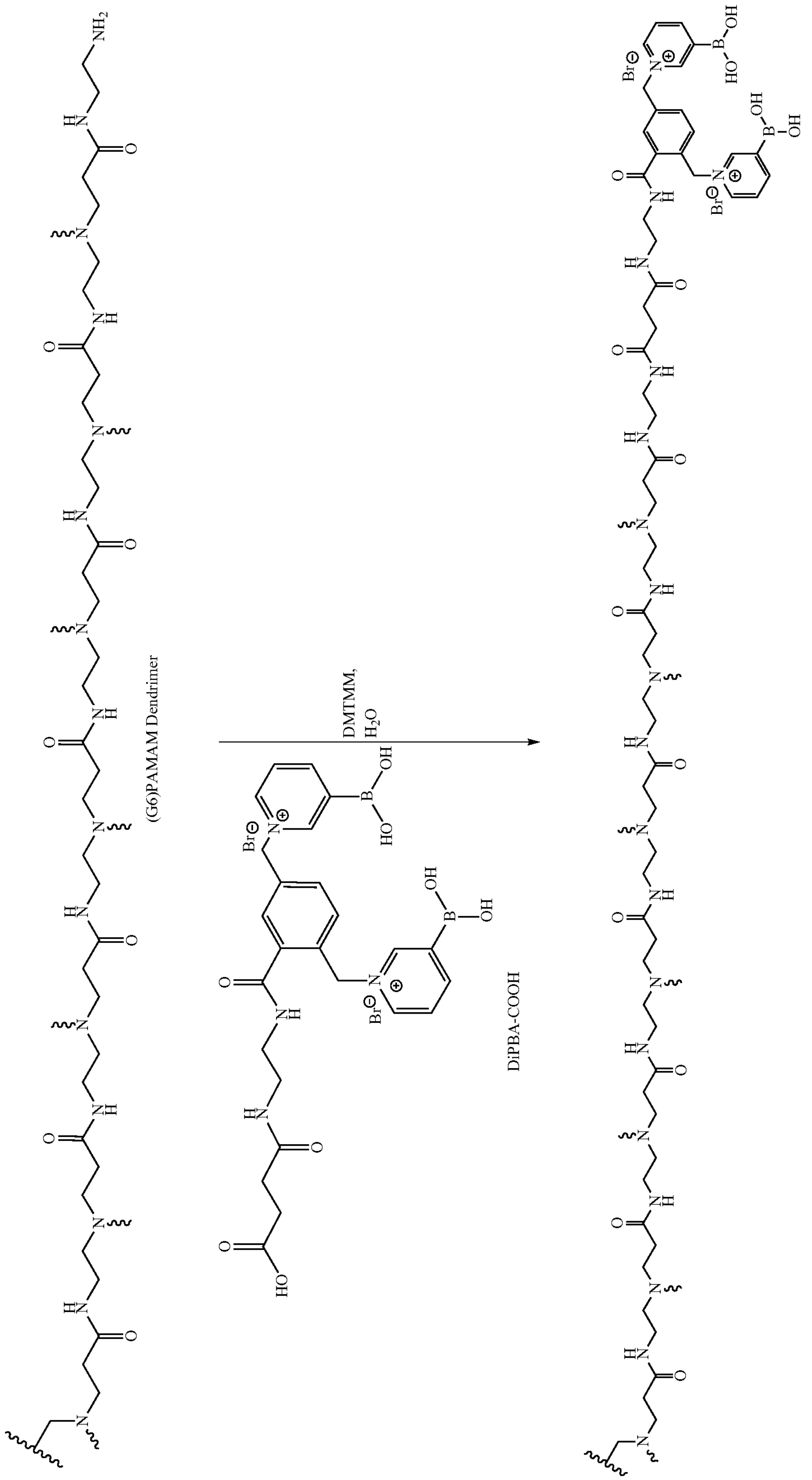
(G6)PAMAM Dendrimer
DiPBA-COOH
(G6)PAMAM Dendrimer-DIPBA

Synthesis of PAMAM Dendrimer-DiPBA

Sixth generation (G6) PAMAM dendrimer (160 mg, 0.003 mmol), DiPBA-COOH (180 mg, 0.26 mmol), and DMTMM (73 mg, 0.26 mmol) were charged to a 100 mL round bottom flask and diluted with 20 mL of DI water. The mixture was stirred at ambient temperature for 4 days before being transferred to a dialysis tube (MWCO of 10,000), dialyzed against water for 24 hours, and lyophilized. $^{1}H$ NMR (400 MHz, $D_2O$) δ 8.55 (s, 65H), 8.52-8.30 (m, 314H), 7.71 (dt, J=19.3, 6.7 Hz, 138H), 7.55-7.39 (m, 203H), 5.81-5.63 (m, 262H), 3.77 (d, J=21.0 Hz, 256H), 3.47-2.98 (m, 1355H), 2.88 (s, 293H), 2.81-2.05 (m, 2400H).

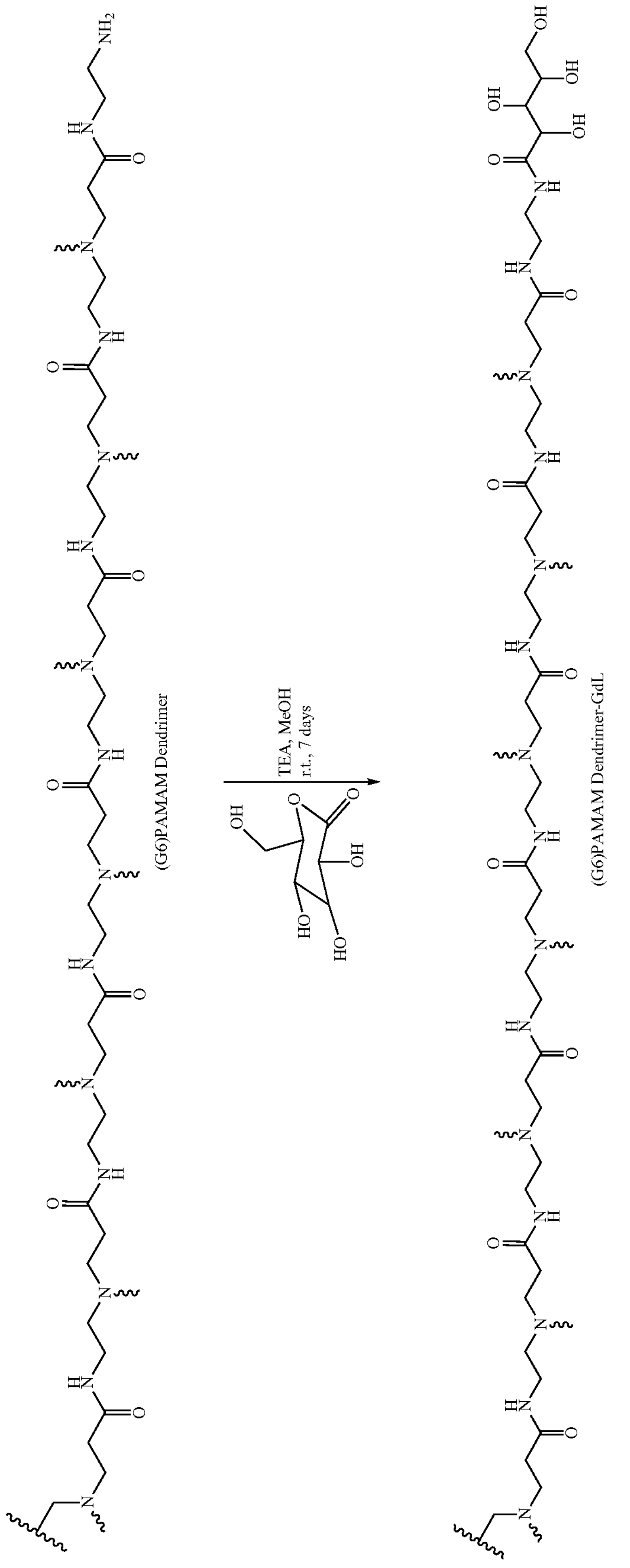
(G6)PAMAM Dendrimer
TEA, MeOH
r.t., 7 days
(G6)PAMAM Dendrimer-GdL

Synthesis of (G6)PAMAM Dendrimer-GdL

A mixture of generation 6.0 (G6) PAMAM dendrimer (58 kDa, 5 g, 0.086 mmol), D-gluconolactone (4.7 g, 26.5 mmol), and triethylamine (TEA, 3 mL, 21.5 mmol) was added to a 1000 mL oven-dried round-bottom flask and diluted with 700 mL MeOH. The mixture was allowed to stir at ambient temperature for 7 days. Methanol was evaporated off and the crude mixture was dissolved in water, transferred to a regenerated cellulose dialysis tube (MWCO of 3,500), dialyzed against water for 24 hours, and lyophilized. $^1H$ NMR (400 MHz, $D_2O$) δ 4.3 (d, 256H), 4.1-3.6 (bs), 3.5-3.1 (bs, 1528H), 3.0-2.6 (bs, 1524H), 2.5-2.3 (bs, 1016H).

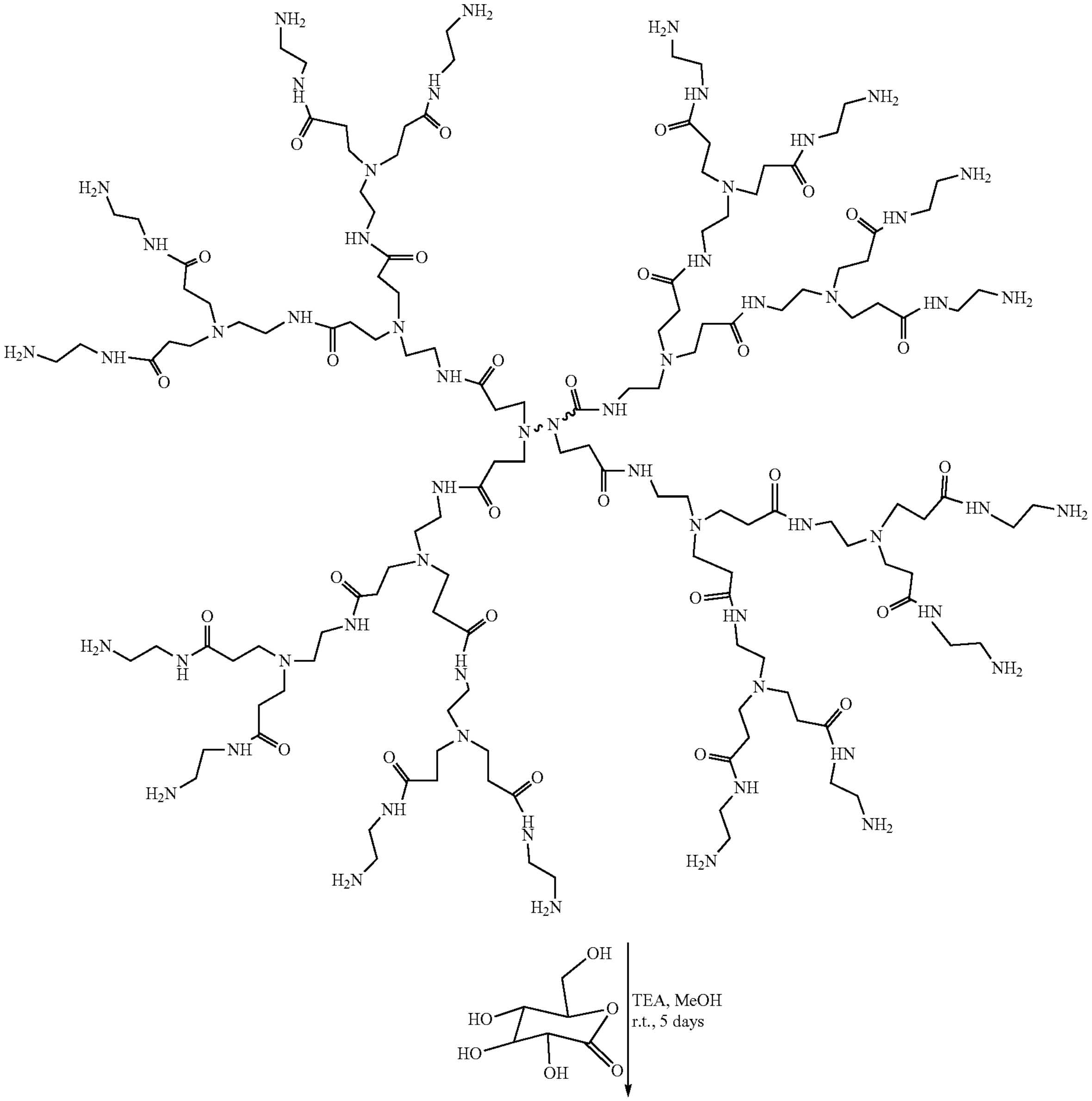

-continued

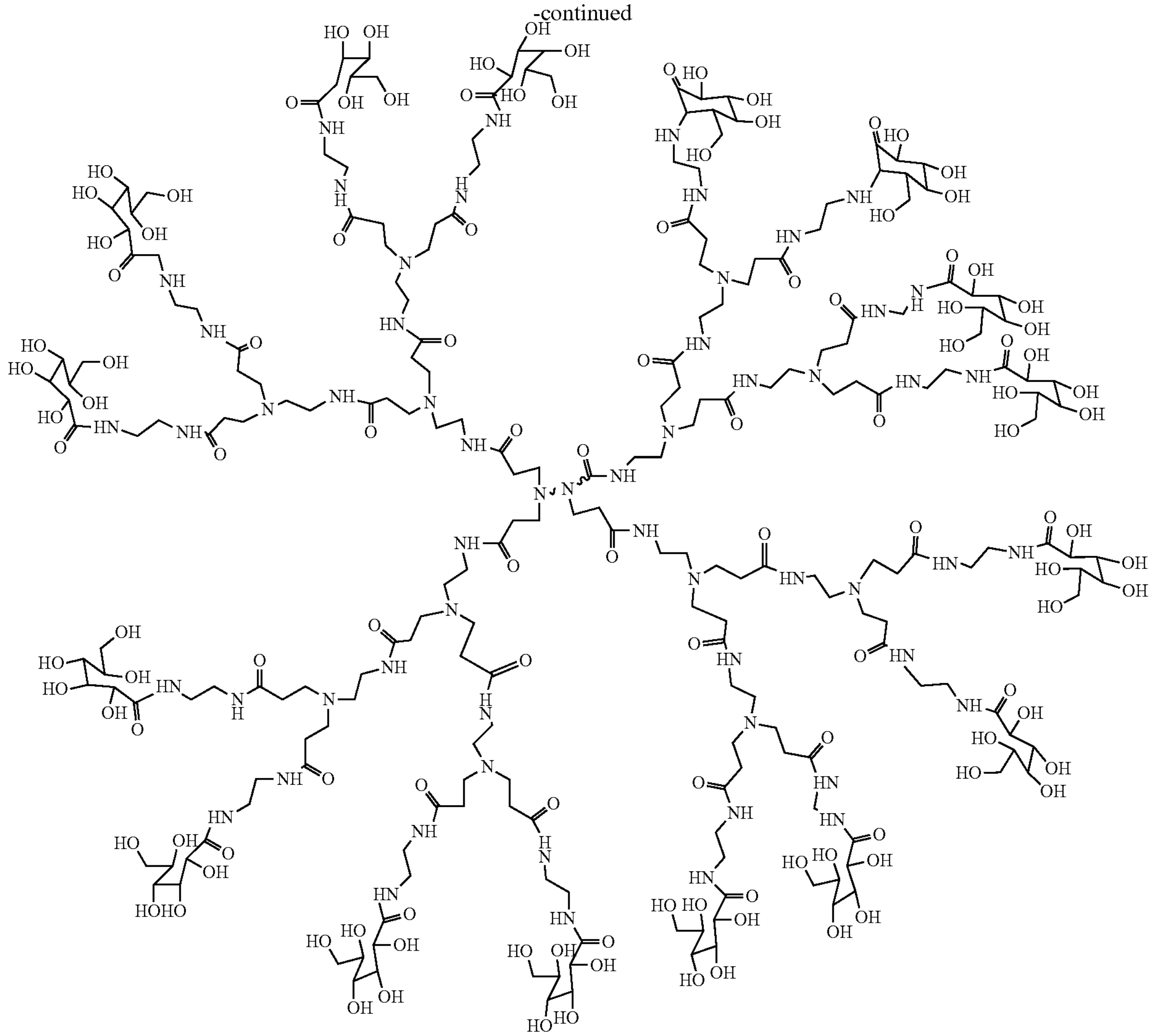

Synthesis of (G2)PAMAM-GdL

A mixture of generation 2.0 (G2) PAMAM dendrimer (3.2 kDa, 1 g, 0.31 mmol), D-gluconolactone (1.3 g, 7.37 mmol), and triethylamine (TEA, 0.7 mL, 5 mmol) was added to a 500 mL oven-dried round-bottom flask and diluted with 300 mL MeOH. The mixture was allowed to stir at ambient temperature for 5 days. Methanol was evaporated off and the crude was dissolved in water, transferred to a regenerated cellulose dialysis tube (MWCO of 3,500), dialyzed against water for 24 hours, and lyophilized. $^1H$ NMR (400 MHz, $D_2O$) δ 4.3 (d, 16H), 4.1-3.6 (bs), 3.5-3.1 (bs, 88H), 3.0-2.6 (bs, 84H), 2.5-2.3 (bs, 56H).

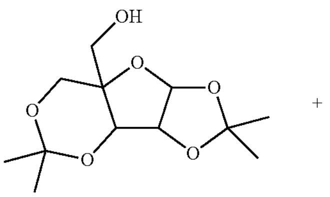

-continued

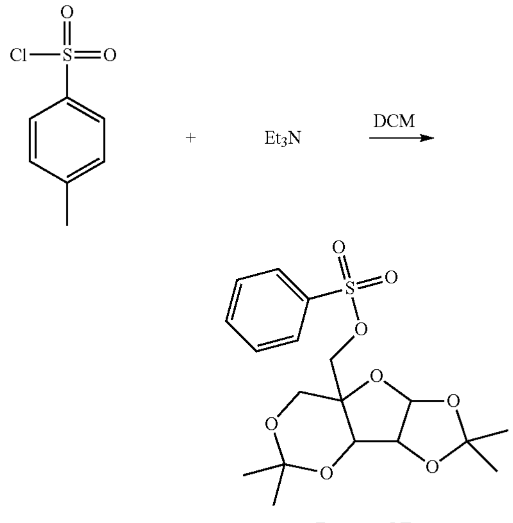

Fructose-OTs

Synthesis of Fructose-OTs (2,2,5,5-Tetramethyltetrahydro-8aH-[1,3]dioxolo[4',5':4,5]furo[3,2-d][1,3]dioxin-8a-yl)methanol (1 g, 4 mmol), 4-dimethylaminopyridine (4-DMAP, 24 mg, 0.2 mmol), and $Et_3N$ (1.15 mL, 8 mmol) were charged to a 100 mL round bottom flask and diluted with 20 mL DCM. The mixture was kept stirring at ambient temperature for 5 mins before the dropwise addition of 4-methylbenzenesulfonyl chloride (1.5 g, 8 mmol) solution in DCM (20 mL). After the addition, the mixture was kept stirring for 24 hrs. After that, the solution was transferred to a separation funnel and washed with water and sat. NaCl, and dried over $Na_2SO_4$. Then the mixture was filtered and concentrated, and the residue was loaded on a column eluting with hexanes/ethyl acetate (EA) for purification. The target product was recovered as a transparent oil. $^1H$ NMR (400 MHz, Chloroform-d) δ 7.84-7.77 (m, 2H), 7.34 (d, J=8.0 Hz, 2H), 4.43 (s, 1H), 4.30 (d, J=2.3 Hz, 1H), 4.22 (d, J=10.5 Hz, 1H), 4.14 (d, J=10.4 Hz, 1H), 4.08 (d, J=1.7 Hz, 1H), 4.02 (dd, J=13.6, 2.2 Hz, 1H), 3.93 (d, J=13.6 Hz, 1H), 2.44 (s, 3H), 1.39 (s, 3H), 1.37 (s, 3H), 1.27 (s, 3H).

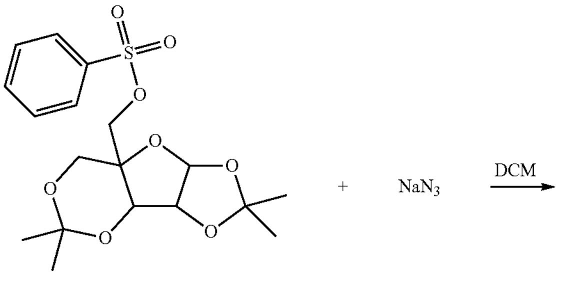

-continued

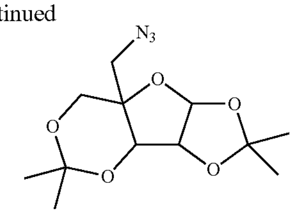

Fructose-$N_3$

Synthesis of Fructose-$N_3$

Fructose-OTs (1 g, 2.4 mmol) and $NaN_3$ (0.9 g, 7.2 mmol) were diluted with 20 mL DMF and stirred at 100° C. for 3 days. The solvent was then removed under vacuum and the residue was loaded on the column, eluting with hexanes/ethyl acetate (EA) for purification. The final target was recovered as light-yellow oil. $^1H$ NMR (400 MHz, Chloroform-d) δ 4.41 (s, 1H), 4.33 (d, J=2.3 Hz, 1H), 4.12 (q, J=2.1 Hz, 1H), 4.08-3.98 (m, 2H), 3.72 (d, J=13.2 Hz, 1H), 3.40 (d, J=13.2 Hz, 1H), 1.47 (s, 3H), 1.42 (s, 3H), 1.36 (s, 3H).

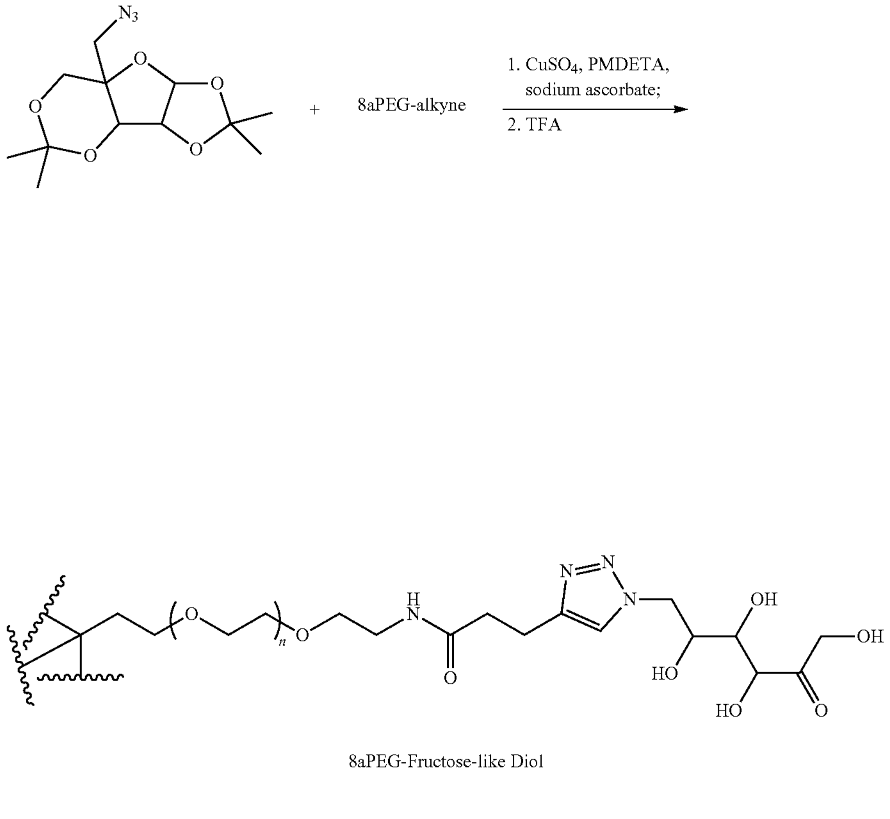

8aPEG-Fructose-like Diol

Synthesis of 8aPEG-Fructose-like Diol

In a 25 mL oven-dried Schlenk flask, 8aPEG-alkyne (0.57 g), copper (II) sulfate pentahydrate ($CuSO_4 \cdot 5H_2O$, 2 mg, BDH, ACS grade), and N,N,N',N",N"-pentamethyldiethylenetriamine (PMDETA, 98%, 3.2 μL, Acros) were added and diluted with DMF (10 mL). The flask was degassed by three freeze-pump-thaw cycles. On the last cycle, the flask was opened to quickly add sodium ascorbate (20 mg) into the flask before re-capping the flask. The flask was vacuumed and backfilled with $N_2$ for 5 cycles, then transferred to a 50° coil for reaction. After 5 days, the reaction was quenched by exposure to air, concentrated to small volume, diluted with 10 mL DCM, and passed through a short $Al_2O_3$ column. The DCM was removed, and residue was diluted with 5 mL MeOH, transferred to a dialysis tube (molecular weight cutoff (MWCO) of 10,000) and dialysis against MeOH. Then the MeOH was removed under vacuum and the residue was treated with 90% TFA in water for 24 hr. After that, the mixture was concentrated and diluted with 10 mL water and transferred to a dialysis tube (MWCO of 10,000), dialyzed against water for 24 hr, and lyophilized. This protocol was suitable for any armed-PEG macromer (4arm, 8arm etc.) of any length (e.g., n=1-100).

Synthesis of Fluorescein Isothiocyanate (FITC)-Insulin

Recombinant Human Insulin (5.8 kDa, 50 mg) was dissolved in sodium carbonate solution (0.1 M, 5 mL), while FITC (3.2 mg) was dissolved in dimethyl sulfoxide (DMSO, 1 mL). Both insulin and FITC solutions were adjusted to pH 11, and the FITC solution was added to the insulin solution dropwise. The reaction mixture was kept in the dark for 12 h. Following this time, the reaction mixture was pH adjusted to 5.3 and the resulting cloudy solution was centrifuged (4000 rpm, 30 min, 4° C.). The pellet was resuspended and dialyzed in DI water in the dark. Finally, the product was collected and lyophilized, yielding a yellow powder. The FITC-insulin product was verified by electrospray ionization mass spectrometry (ESI-MS, Advion) to ensure successful conjugation.

Acid-Base Titration

A 0.01 M stock solution of the PBA of interest was prepared by dissolving 0.2 mmol of each PBA in 20 mL DI water. The solution was then titrated with 0.005 M NaOH solution under constant stirring with pH monitoring.

Oscillatory Rheology

Hydrogel mechanical properties were evaluated with a TA Instruments HR-2 rheometer fitted with a Peltier stage set to 25° C. All measurements were performed using a 25 mm parallel plate geometry. Oscillatory strain amplitude sweep measurements were first conducted at a frequency of 20 rad/s. Oscillatory frequency sweep measurements were then conducted at 3% strain after verification that this was in the linear viscoelastic region for all materials. Several rheology studies were performed, and hydrogels were prepared according to the various parameters being assessed: (i) For studies of concentration-dependent hydrogelation, stock solutions of PBA-bearing macromers (4aPEG-DiPBA, 4aPEG-PyPBA, or 4aPEG-FPBA) and 4aPEG-diol were prepared in 1×PBS. To formulate hydrogels, appropriate volumes of each macromer stock solution (at 1:1 motif to diol by mole) and PBS were combined to yield the final desired polymer concentration. (ii) For studies of glucose-dependent hydrogelation, glucose-containing buffers were prepared by dissolving glucose with PBS to yield a desired glucose concentration (0 mg/dL, 100 mg/dL, 200 mg/dL, and 400 mg/dL). Then stock solutions of PBA-bearing macromers (4aPEG-DiPBA, 4aPEG-PyPBA, or 4aPEG-FPBA) and 4aPEG-diol were prepared in these various glucose-containing PBS solutions. To formulate hydrogels, appropriate volumes of each macromer stock solution (at 1:1 motif to diol by mole) were combined to yield a final desired polymer concentration of 2 mM. (iii) For analyte-dependent hydrogelation, lactate, fructose, and glucose were dissolved in PBS to yield their final desired concentrations (Lactate: 5 mM, Fructose: 1 mM, Glucose: 22 mM). Then stock solutions of PBA-bearing macromers (4aPEG-DiPBA, 4aPEG-PyPBA, or 4aPEG-FPBA) and 4aPEG-diol were prepared in these various PBS solutions. To formulate the hydrogels, appropriate volumes of each macromer stock solution (at 1:1 motif to diol by mole) were combined to yield a final desired polymer concentration of 2 mM in the buffer containing the desired analyte.

Isothermal Titration Calorimetry

The binding affinities ($K_{eq}$) between different small molecule PBAs and model analytes (FIG. 2) were measured through isothermal titration calorimetry (ITC). All titration experiments were performed at 298 K on a PEAQ-ITC calorimeter (MicroCal, Inc.) in degassed pH 7.4 PBS buffer, using a 38 μL syringe and 200 μL cells and consisting of 19 injections. The measurements were performed by titrating glucose, fructose, sodium lactate, or $Diol_{sm}$ from the syringe into a solution of small molecule variants of $DiPBA_{sm}$, $PyPBA_{sm}$, or $FPBA_{sm}$ loaded in the cell. In all titration experiments, the cell concentration was 1 mM, while the analyte concentrations in the syringe were varied according to experimental optimization. All raw data were corrected by subtraction of a dilution measurement of the titrated analytes into buffer and were then analyzed and graphed using the integrated public-domain software packages of NIPIC, SEDPHAT, and GUSSI according to a published protocol. See Brautigam et al., *Nat. Protoc.* 11(5): 882-894 (2016).

FITC-Insulin Release Studies

A variety of studies were performed to assess the glucose-responsive and glucose-specific release of insulin from hydrogels. (i) To evaluate glucose-dependent FITC-insulin release from hydrogels, 0.1 mL hydrogels were prepared in a pH 7.4 PBS buffer at 2 mM polymer concentration (at 1:1 PBA to diol by mole) along with 20 μg FITC-insulin per hydrogel. Gels were then incubated in circular molds placed within 12-well plates and immersed in 3.5 mL of pH 7.4 release buffer containing 2.3, 5.5, 11 or 22 mM of glucose. At each time point, a 20 μL aliquot was taken and further diluted to 200 μL for fluorescence analysis (Ex: 485 nm, Em: 520 nm) on a Tecan M200 plate reader. The bulk was adjusted by addition of 20 μL of the same release buffer to maintain constant volume with each sampling. Released FITC-insulin concentrations were determined using a standard curve. After 8 h, gels were manually destroyed by treating with HCl solution to disrupt any remaining gel network and free residual FITC-insulin. The pH of this mixture was adjusted to pH 7.4 and insulin was quantified for mass balance closure. (ii) To evaluate FITC-insulin release upon a sudden increase in glucose level to mimic a hyperglycemic spike, hydrogels were prepared as before and immersed in 3.5 mL of pH 7.4 release buffer containing 2.3 mM glucose for 2 h. Subsequently, the release buffer was completely removed and replaced with 3.5 mL of pH 7.4 buffer containing 22 mM glucose and release was monitored for an additional 2 h. At each time point, a 20 μL aliquot was taken and further diluted to 200 μL for fluorescence analysis, and endpoint analysis and mass balance closure were performed, as before. (iii) To evaluate glucose-specific FITC-insulin release from hydrogels, 0.1 mL of hydrogel were prepared as before in pH 7.4 PBS at 2 mM polymer concentration and containing 20 μg FITC-insulin. Gels were then immersed in 3.5 mL of pH 7.4 PBS containing either (a) 5 mM glucose and 0.5 mM sodium lactate, (b) 5 mM glucose and 5 mM sodium lactate, (c) 10 mM glucose and 0.5 mM sodium lactate, or (d) 10 mM glucose and 5 mM sodium lactate. At each time point, 20 μL samples were collected, diluted to 200 μL, and analyzed as normal, along with replacement of 20 μL fresh buffer to the bulk. After 8 hours, gels were manually destroyed by HCl and analyzed for insulin content to ensure mass balance closure. (iv) To evaluate FITC-insulin release with a sudden increase in sodium lactate to mimic post-exercise elevation, 0.1 ml of hydrogel were prepared as before in pH 7.4 PBS at 2 mM polymer concentration and containing 20 μg FITC-insulin. Gels were then immersed in 3.5 mL of pH 7.4 buffer containing 10 mM glucose and 0.5 mM sodium lactate for 2 h. Subsequently, the release buffer was completely removed and replaced with 3.5 mL of pH 7.4 buffer containing 10 mM glucose and 5 mM sodium lactate for 2 h. At each time point, a 20 μL aliquot was taken and further diluted to 200 μL for fluorescence analysis, and endpoint analysis and mass balance closure were performed, as before.

Blood Glucose Control In Vivo

To evaluate the performance hydrogels for blood glucose control, male C57BL6/J mice (8 weeks old, ~25 g/mouse; Jackson Laboratory) were induced to be insulin deficient using streptozotocin (STZ). Mice were fasted for 4 h, following which a single intraperitoneal (i.p.) injection of STZ at a dose of 150 mg/kg was administered. Following an additional 30 min fast, food was returned. Seven days following STZ treatment, insulin-deficient diabetes was verified using hand-held blood glucose meters (CVS brand) with unfasted blood glucose (BG) levels ensured to be above 600 mg/dL for study inclusion. Mice were then fasted for 12 h, and those with BG >550 mg/dL were randomly divided into 4 groups (n=5-6/group). Groups were treated with one of the following: (a) 0.1 mL pH 7.4 PBS buffer, (b) 0.1 mL human recombinant insulin (4 IU/kg), (c) 0.1 mL insulin-loaded DiPBA hydrogel (1:1 molar ratio of 4aPEG-DiPBA to 4aPEG-diol, insulin dose of 7 IU/kg), or (d) 0.1 mL insulin-loaded FPBA hydrogel (1:1 molar ratio of 4aPEG-FPBA to 4aPEG-diol, insulin dose of 7 IU/kg) via subcutaneous (s.c.) injection. BG level were continuously monitored for 3 h after treatment. To examine gel response to a sudden increase in BG, a glucose tolerance test was performed by i.p. injection of glucose (1.25 g/kg glucose, 0.1 mL). BG were subsequently monitored for 3 h. A total of two IPGTT cycles were performed. Mice were fasted for the duration of the experiment with continuous access to water. All experiments followed a protocol approved by the University of Notre Dame Animal Care and Use Committee (IACUC) and adhered to all relevant Institutional, State, and Federal guidelines. Areas under the curve (AUC) were calculated using the trapezoidal rule and statistical analyses were performed to compare DiPBA and FPBA treatment groups using GraphPad Prism v9.0, with significance obtained using a Student's t-test.

Calculation of Overlap Concentration (c*)

To calculate overlap concentration (c*) for these networks, the following relation was used:

$$c^* = \frac{M}{\frac{4}{3}\pi(R_g)^3 N_A}$$

where M is the macromer molecular weight (10,000 g/mol), $R_g$ is its radius of gyration (nm), and $N_A$ is Avagadro's number. See Wehrman et al., *AIChE J.* 64 3168-3176 (2018). The $R_g$ for a star PEG polymer can be estimated as follows:

$$R_g^{star} = R_g^{arm}\left[\frac{3f-2}{f}\right]^{1/2}$$

where $R_g^{arm}$ is the radius of gyration of a single arm of the star and f is the number of arms on the macromer. See Wehrman, id. To estimate $R_g^{arm}$ (in nm) of PEG in a good solvent, the following relation was used:

$$R_g^{arm} = 0.0215 * M_{arm}^{0.583}$$

with M for a single arm of 2500 g/mol. See Devanand and Selser, Macromolecules 24: 5943-5947 (1991). From this relationship, $R_g^{arm}$ was determined to be 2.06 nm, resulting in a value for $R_g^{star}$ of 3.25 nm. Accordingly, c* was estimated to be 0.115 g/mL or 11.5 wt %.

Example 2

Figure 2A:
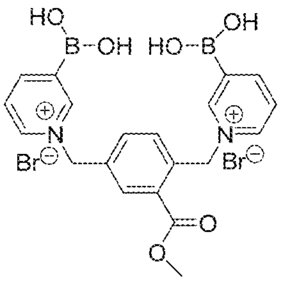
FIG. 2A shows the model small molecules (denoted by "sm") that were used for isothermal titration calorimetry (ITC) studies. The model small molecules shown are $DiPBA_{sm}$, $PyPBA_{sm}$, $FPBA_{sm}$, $DiPBA1_{sm}$, $DiAPBA_{sm}$, $DiPBA3_{sm}$, $Diol_{sm}$, glucose, fructose, and sodium lactate.
Figure 2A:
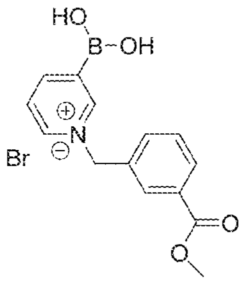
Figure 2A:
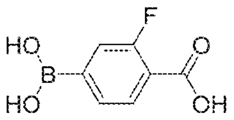
Figure 2A:
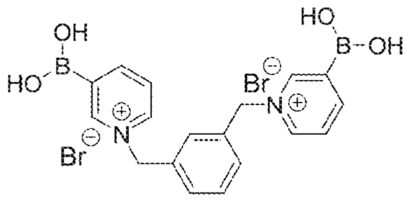
Figure 2A:
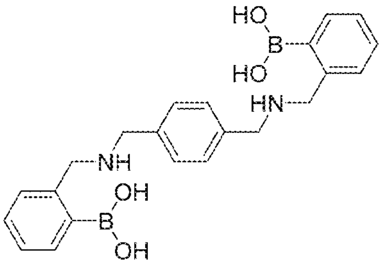
Figure 2A:
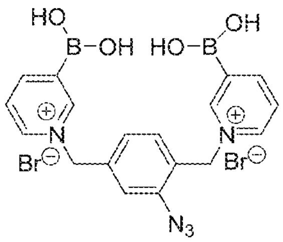
Figure 2A:
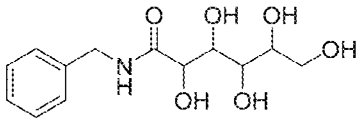
Figure 2A:
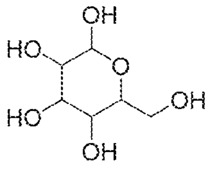
Figure 2A:
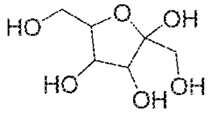
Figure 2A:
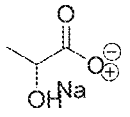
Figure 2B:
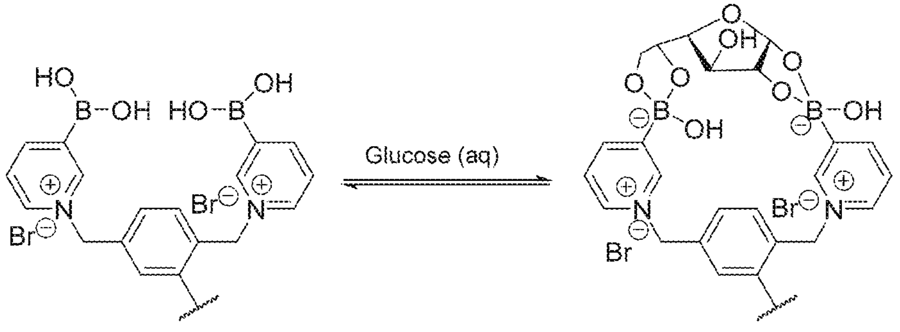
FIG. 2B shows the DiPBA-Diol interaction for simultaneous glucose binding by both boronates of the DiPBA.
Figure 3A:
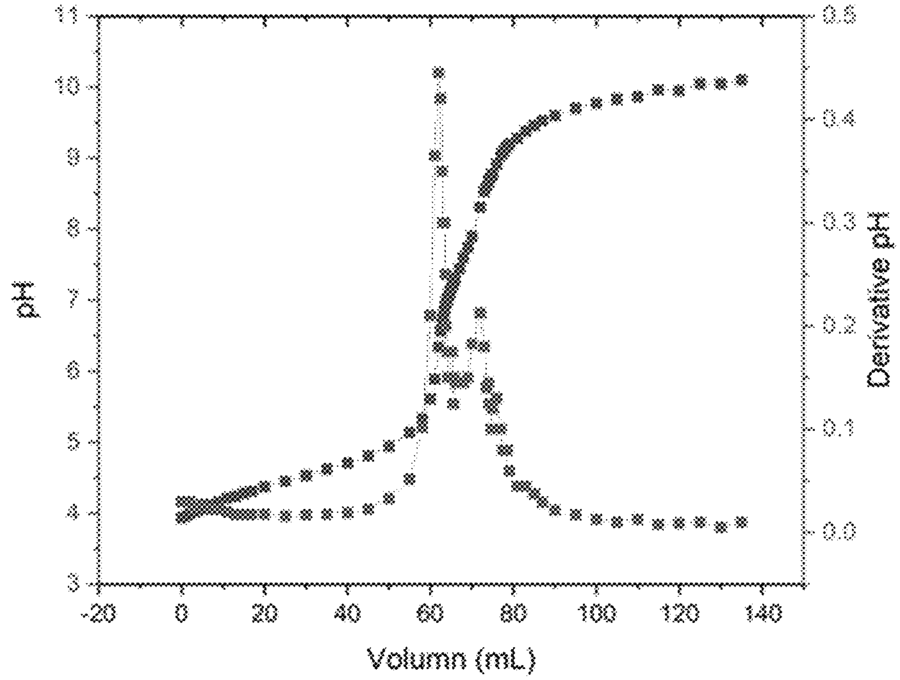
FIG. 3A-C show acid-base titration for $pK_a$ determination using small molecules of DiPBA ($DiPBA_{sm}$, FIG. 3A), PyPBA ($PyPBA_{sm}$, FIG. 3B), and FPBA ($FPBA_{sm}$, FIG. 3C).
Figure 3B:
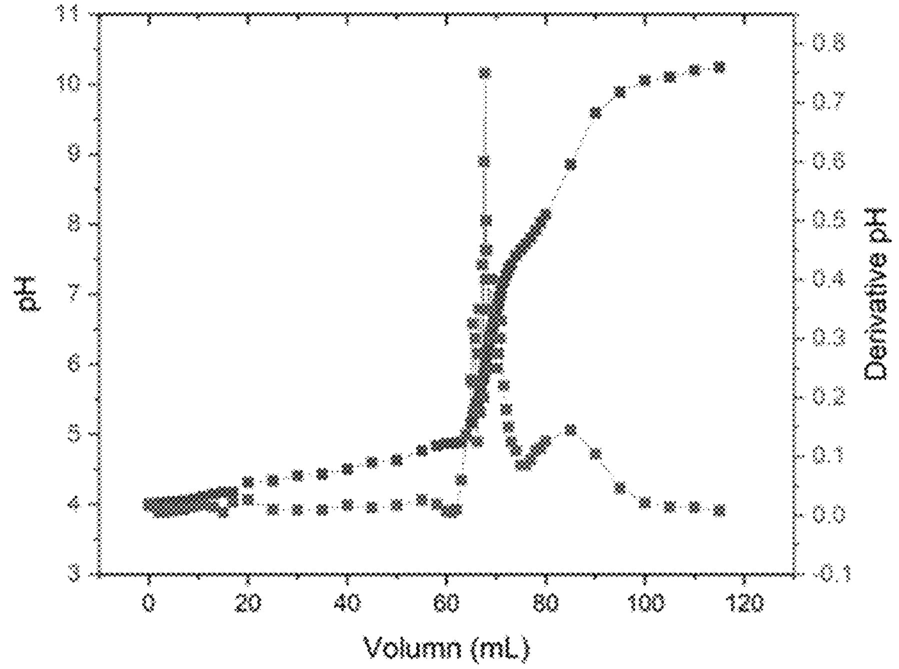
Figure 3C:
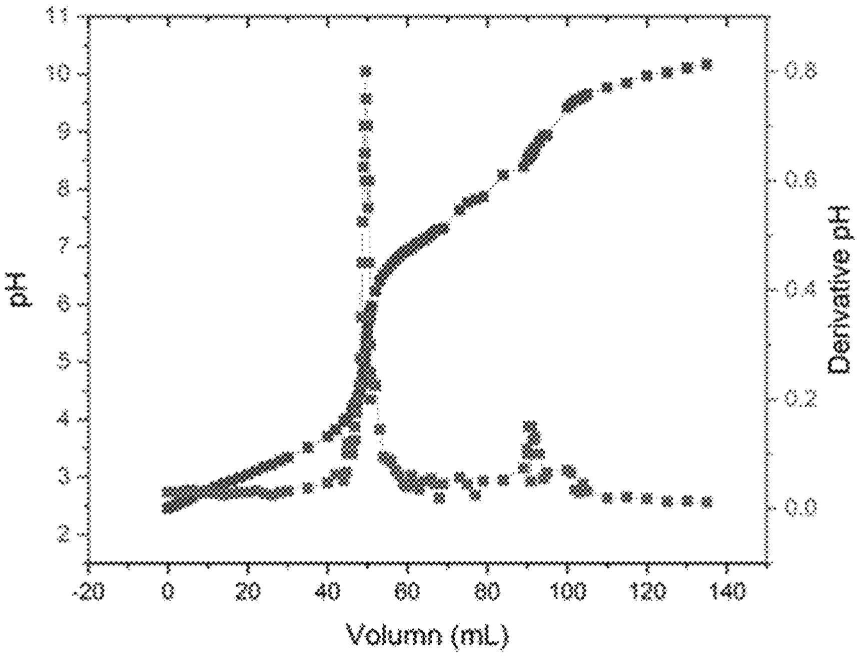
Figure 3D:
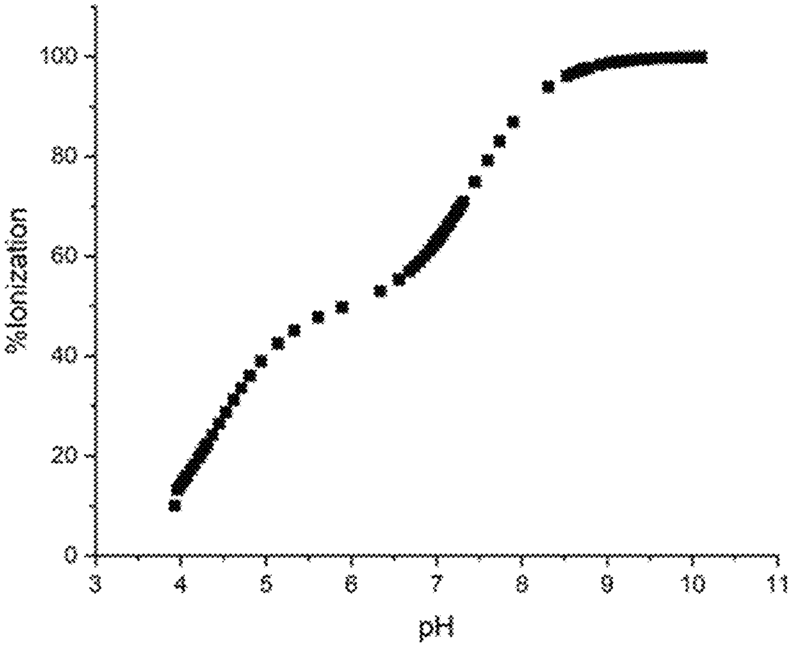
FIG. 3D-F shows the percent ionization of boronic acid as a function of pH for $DiPBA_{sm}$ (FIG. 3D; the value was calculated with each $pK_a$ and then averaged. For $PyPBA_{sm}$ (FIG. 3E) and $FPBA_{sm}$ (FIG. 3F), the value was calculated for the $pK_a$ of boronic acid only.
Figure 3E:
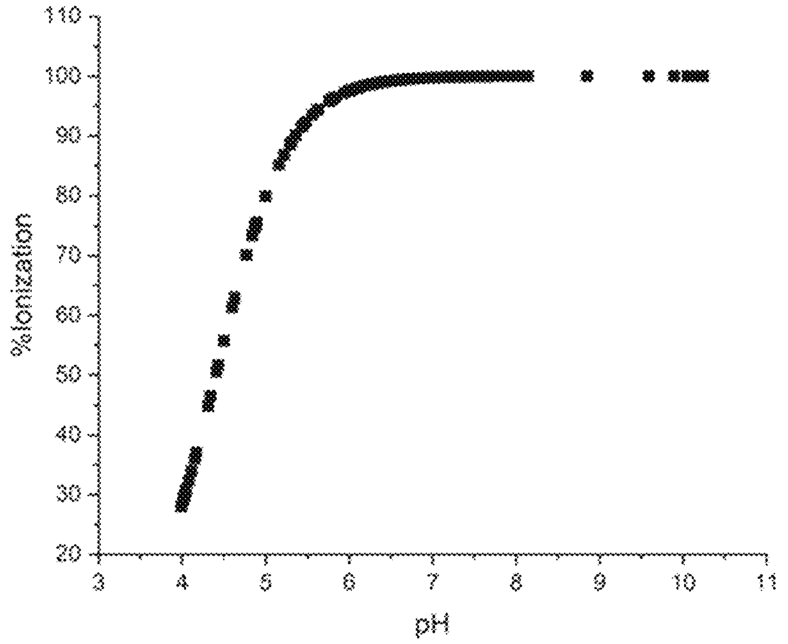
Figure 3F:
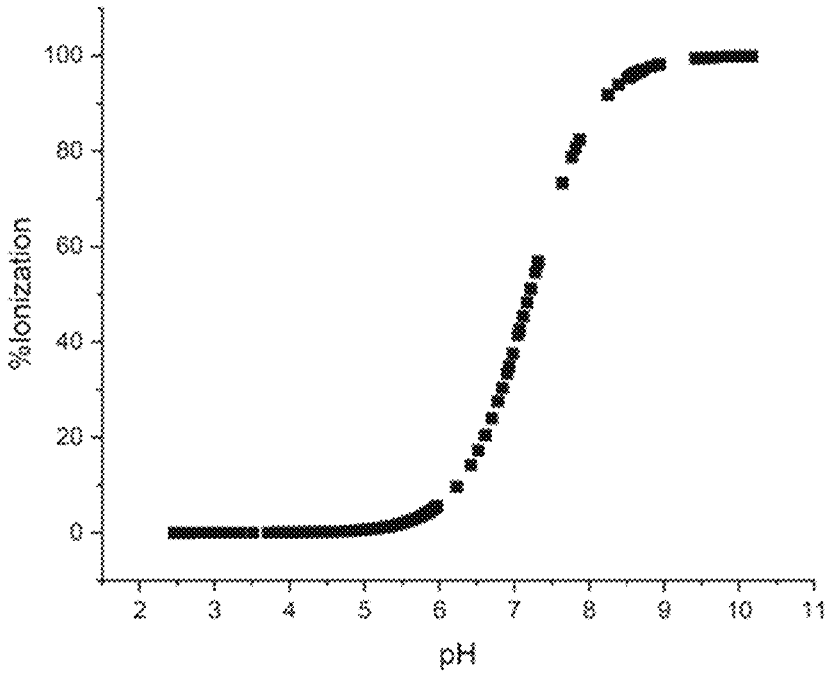

Previously reported diboronate glucose sensors include architectures of two phenylboronic acids attached to an aryl core via charged ammonium linkers. In a variation on this approach, the DiPBA motif explored here has introduced adjacent charge via pyridine-based phenylboronic acid structures (FIG. 1B). Besides conserving adjacent positive charge, the topology of this novel design was also intended to afford a more rigid pocket for simultaneous glucose binding by both boronates (FIG. 2B). Details for the synthesis and molecular characterization of this novel DiPBA group, along with all other synthetic small molecules and macromers, are reported in the Online Supporting Information. As a control for this glucose-binding motif, a single pyridine-PBA (PyPBA) was also synthesized. DiPBA and PyPBA motifs were compared in this work to a fluorine-substituted PBA motif (FPBA) that has been routinely reported in glucose-responsive materials and therapeutic constructs. PBA binding to glucose and related diols exhibits a known dependence on the $pK_a$ of the boronate, with glucose binding occurring preferentially at pH values near or above the $pK_a$ of the particular PBA used. Accordingly, the $pK_a$ values of these three motifs were estimated by acid-base titration (FIG. 3) and found to be $pK_{a1}$=4.53 and $pK_{a2}$=7.45 (DiPBA), 4.41 (PyPBA), and 7.32 (FPBA). These results are comparable to previously reported pKa values for an FPBA variant (~7.2) and a PyPBA variant (~4.4).

To first quantify the affinities of binding for these different PBA motifs to glucose, related analytes, and model diols, a set of small molecules (FIG. 2) were synthesized for isothermal titration calorimetry (ITC) studies. A number of important trends emerge from these data (FIG. 4A; FIG.

5-8). For the DiPBA motif, its $K_{eq}$ for binding to glucose was 1295 $M^{-1}$, which was 1.7 times higher than that for fructose and 29 times higher than that for lactate. By comparison, the commonly used FPBA motif had $K_{eq}$ for glucose binding of only 8.6 $M^{-1}$. This FPBA chemistry, meanwhile, demonstrated affinity for fructose that was 78 times higher and affinity for lactate that was 8 times higher than was found for glucose binding. The magnitude of FPBA binding to glucose from these measurements was comparable to values previously reported for related PBA chemistries (4.6 $M^{-1}$), with this same prior report also noting affinity for fructose that was ~35 times higher than that for glucose. Comparing the present results to these data obtained using common spectroscopic methods furthermore support the use of ITC in these studies here. Accordingly, concerns over low-affinity glucose-binding and poor glucose selectivity of traditional PBAs are supported by these ITC data, with both issues seemingly overcome using DiPBA chemistry. Interestingly, the PyPBA chemistry showed increased affinity for glucose (164.7 $M^{-1}$) compared to FPBA, while also having reduced fructose and lactate binding. Finally, to explore the likely outcomes of using each of these PBA motifs in the context of dynamic-covalent networks a model diol (GdL-Diol) was prepared from reaction of glucono-δ-lactone (GdL) with benzylamine. The $K_{eq}$ of binding for each PBA motif to this model diol were nearly identical (~$5\times10^3$ $M^{-1}$); this finding confirms similar 1:1 binding stoichiometry between all three PBA chemistries studied here and the GdL-derived diol chemistry commonly used in preparing dynamic-covalent PBA-diol networks.

Once small molecules were synthesized and validated for their binding, PBA-modified macromers were prepared by end-group functionalization of 10 kDa 4-arm polyethylene glycol (4aPEG, FIG. 1B), with the goal of realizing ideal network hydrogel materials through dynamic-covalent PBA-diol crosslinking. Briefly, DiPBA-4aPEG and PyPBA-4aPEG were synthesized via thiol-maleimide Michael addition between 4aPEG-SH and maleimide-modified DiPBA or PyPBA small molecules. This route used high-yielding conjugation chemistry to achieve quantitative modification of macromers, simultaneously avoiding harsh alternative reaction conditions that were found to compromise stability of pyridine-based PBA motifs in preliminary efforts. The FPBA-4aPEG was synthesized via amide formation between 4aPEG-$NH_2$ and 4-carboxy-3-fluorophenylboronic acid following previously reported methods, achieving quantitative functionalization. See Yesilyurt et al., *Adv. Mater.* 28(1): 86-91 (2016). To prepare a diol-modified macromer (Diol-4aPEG) for construction of the hydrogel network, 4aPEG-$NH_2$ was reacted with GdL in the presence of triethylamine as previously reported, yielding a fully modified macromer.

Figures 4A, 4B:
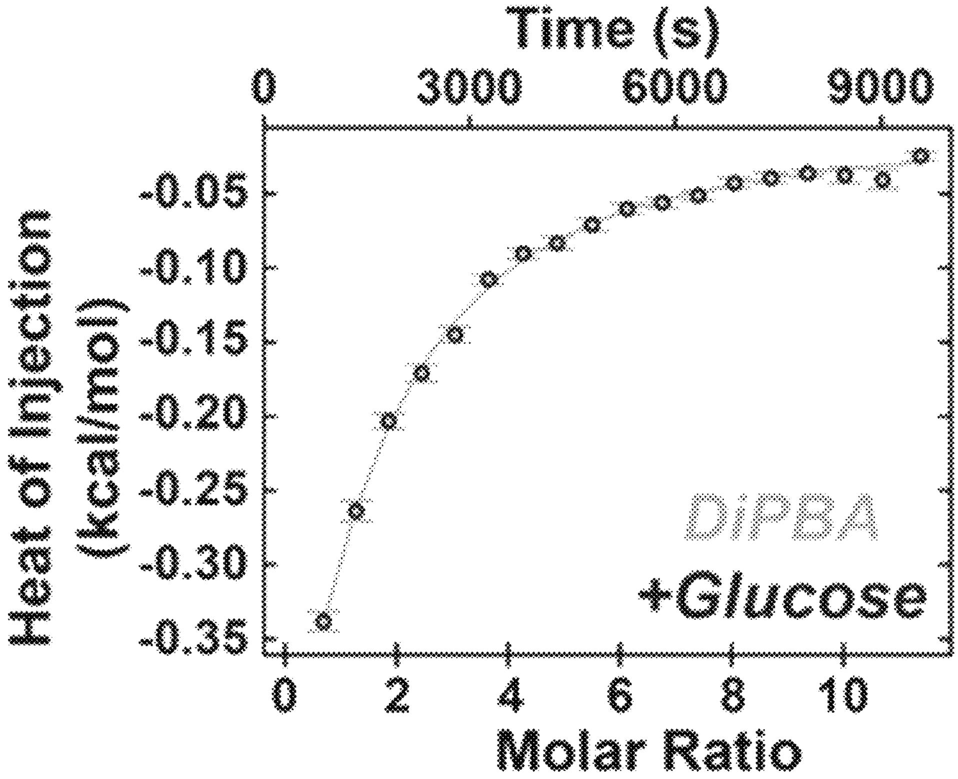
FIG. 4A-D show binding affinities ($K_{eq}$) determined from isothermal titration calorimetry (ITC) data performed on small molecule ("sm") variants of the DiPBA ($DiPBA_{sm}$), FPBA ($FPBA_{sm}$), and PyPBA ($PyPBA_{sm}$) binders with glucose, fructose, lactate, and a model diol crosslinker motif (glucono-δ-lactone-diol ("GdL-diol")) (FIG. 4A) along with representative presentation of model-fitted data for DiPBA with glucose (FIG. 4B); a model diol crosslinker motif (GdL-diol, FIG. 4C); fructose (FIG. 4D), and lactate (FIG. 4E).
Figure 4C:
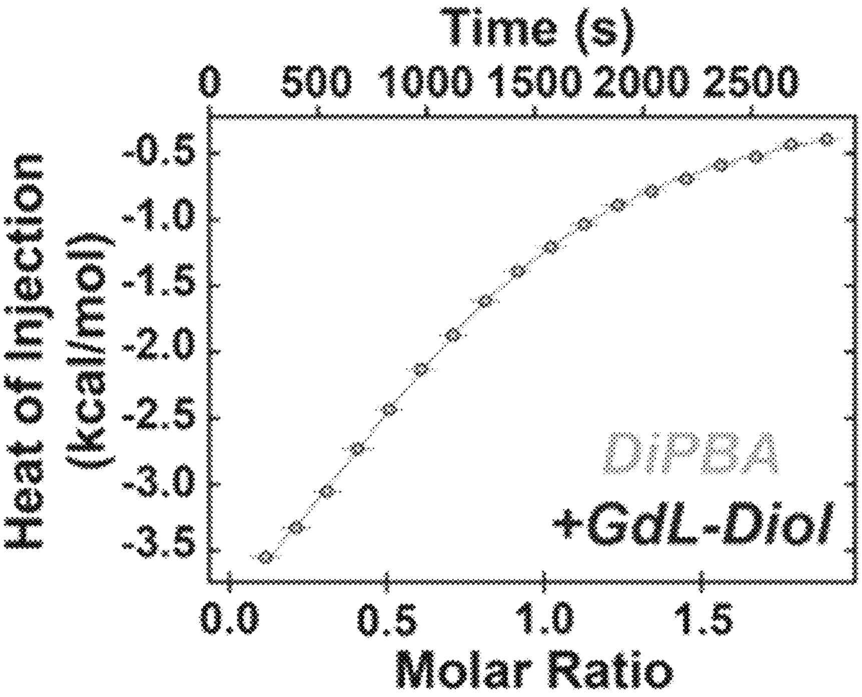
Figure 4D:
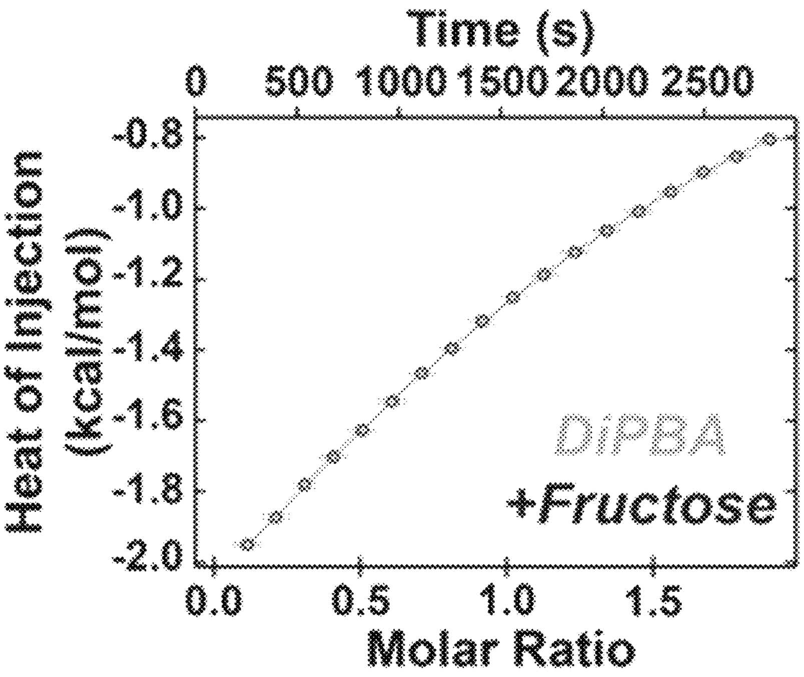
Figure 4E:
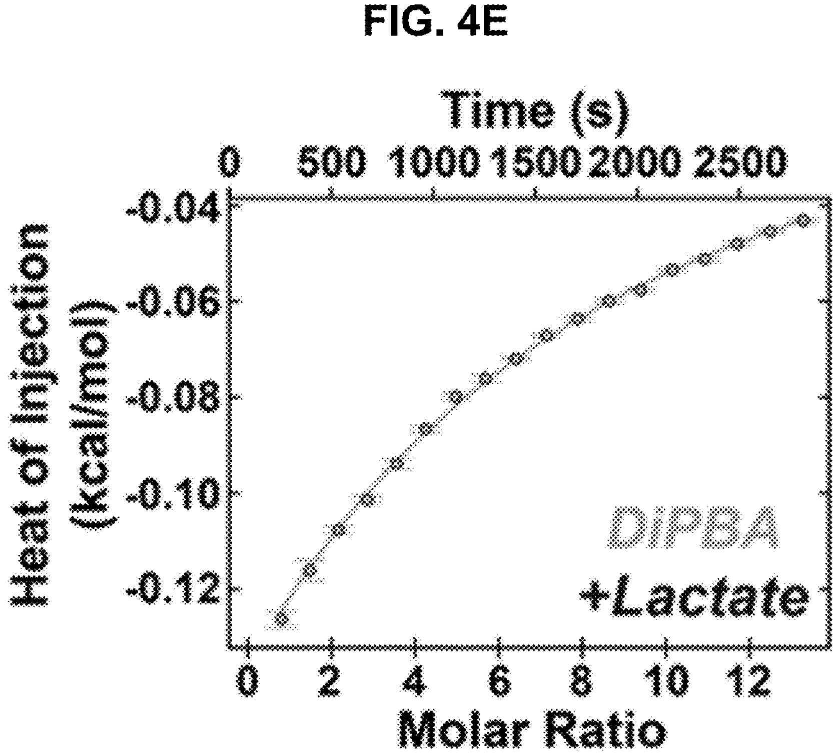
FIG. 4F shows representative concentration-dependent oscillatory rheology frequency sweep data for hydrogels prepared from DiPBA-diol crosslinking. The G'/G" crossover is used to approximate the network relaxation rate (TR).
FIG. 4G shows the plateau moduli ($G_p$, G' at twice G'/G" crossover) from frequency sweeps of each network were fit to a dynamic phantom network model to estimate the binding affinity ($K_{eq}$) of the dynamic-covalent crosslinking interactions in the gel.
Figure 4F:
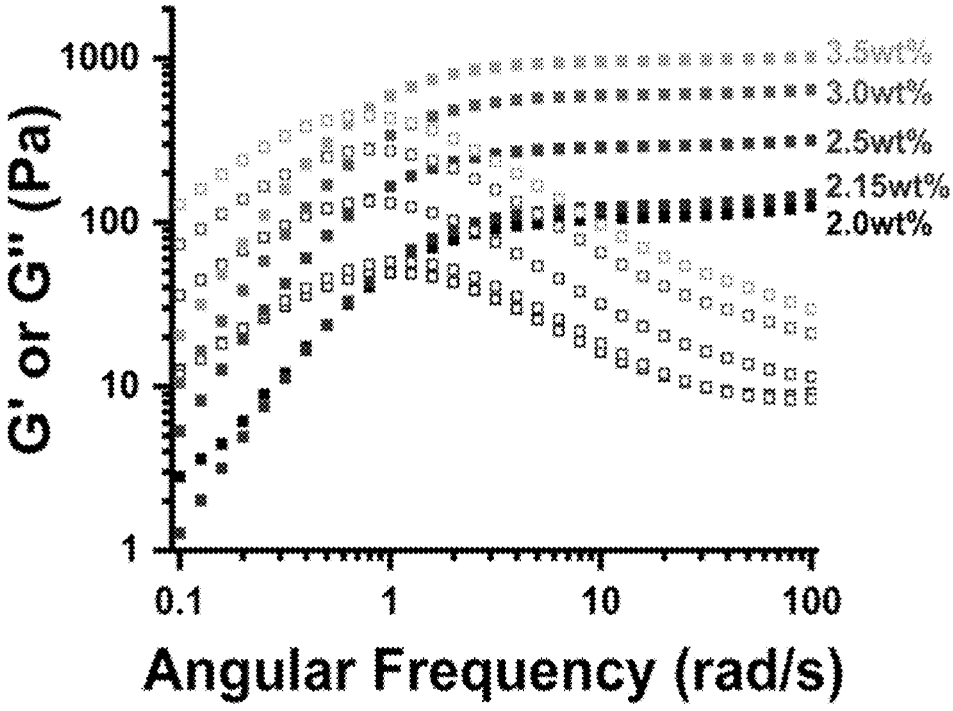
Figure 4G:
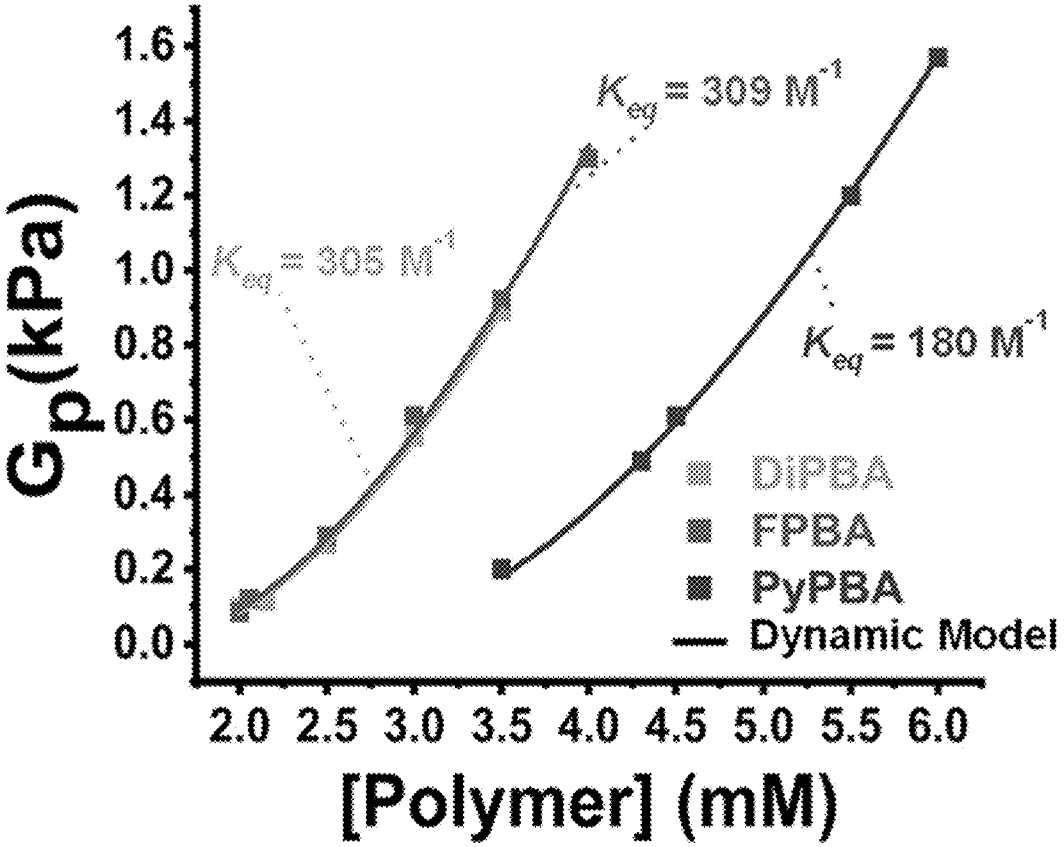
Figure 5A:
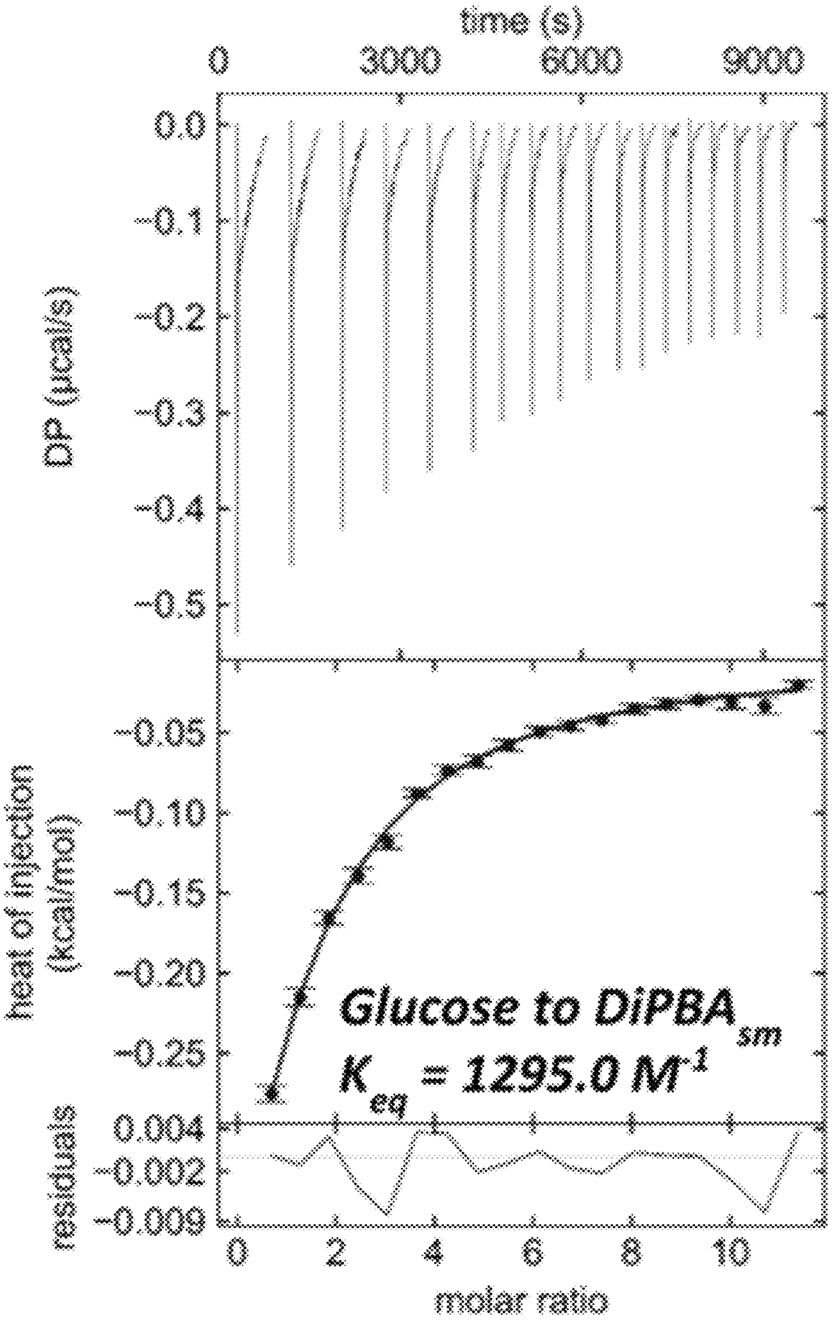
FIG. 5A-C show isothermal titration calorimetry (ITC) data from titrating glucose into small molecules of DiPBA ($DiPBA_{sm}$, FIG. 5A), PyPBA ($PyPBA_{sm}$, FIG. 5B), and FPBA ($FPBA_{sm}$, FIG. 5C).
Figure 5B:
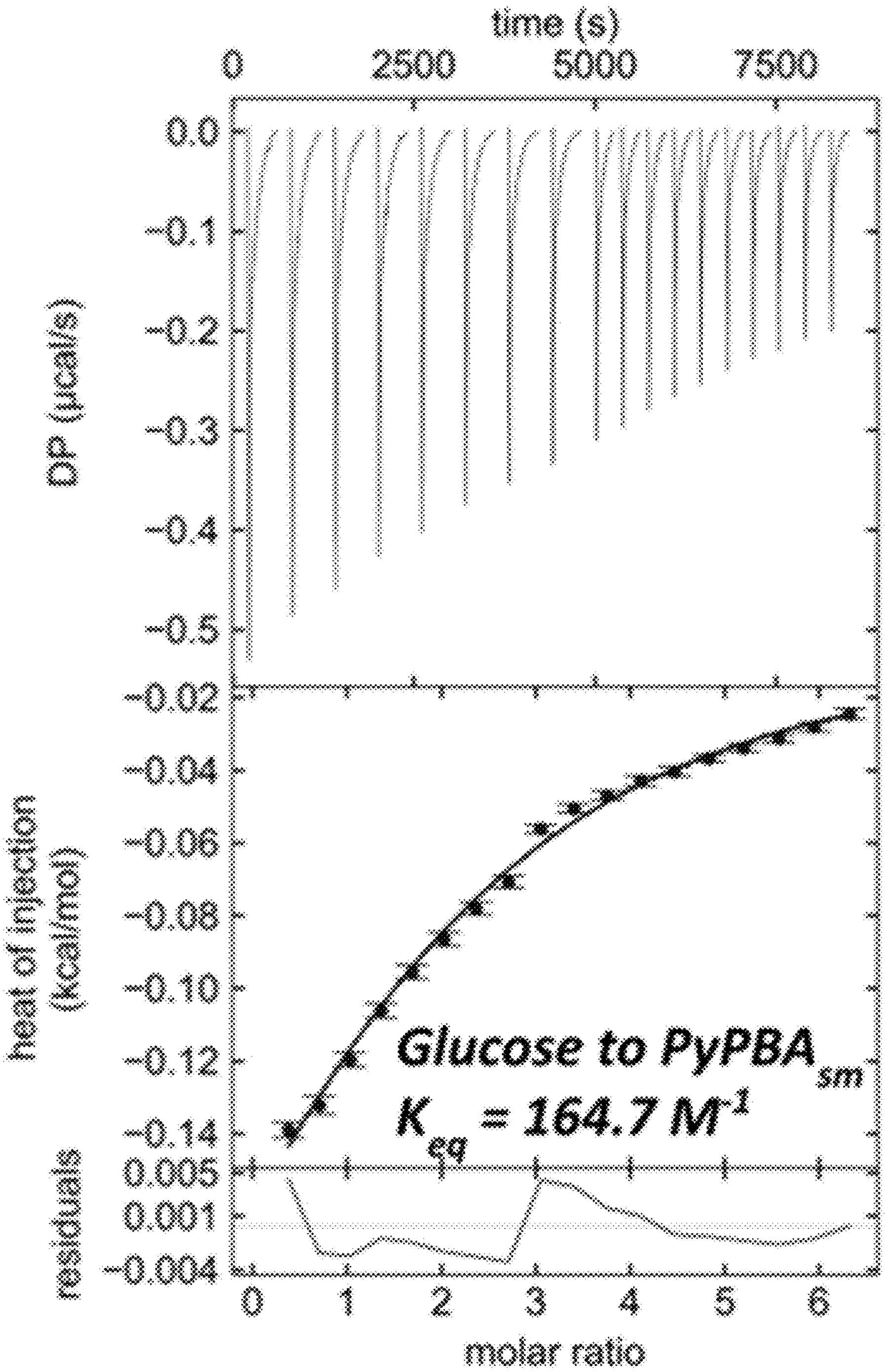
Figure 5C:
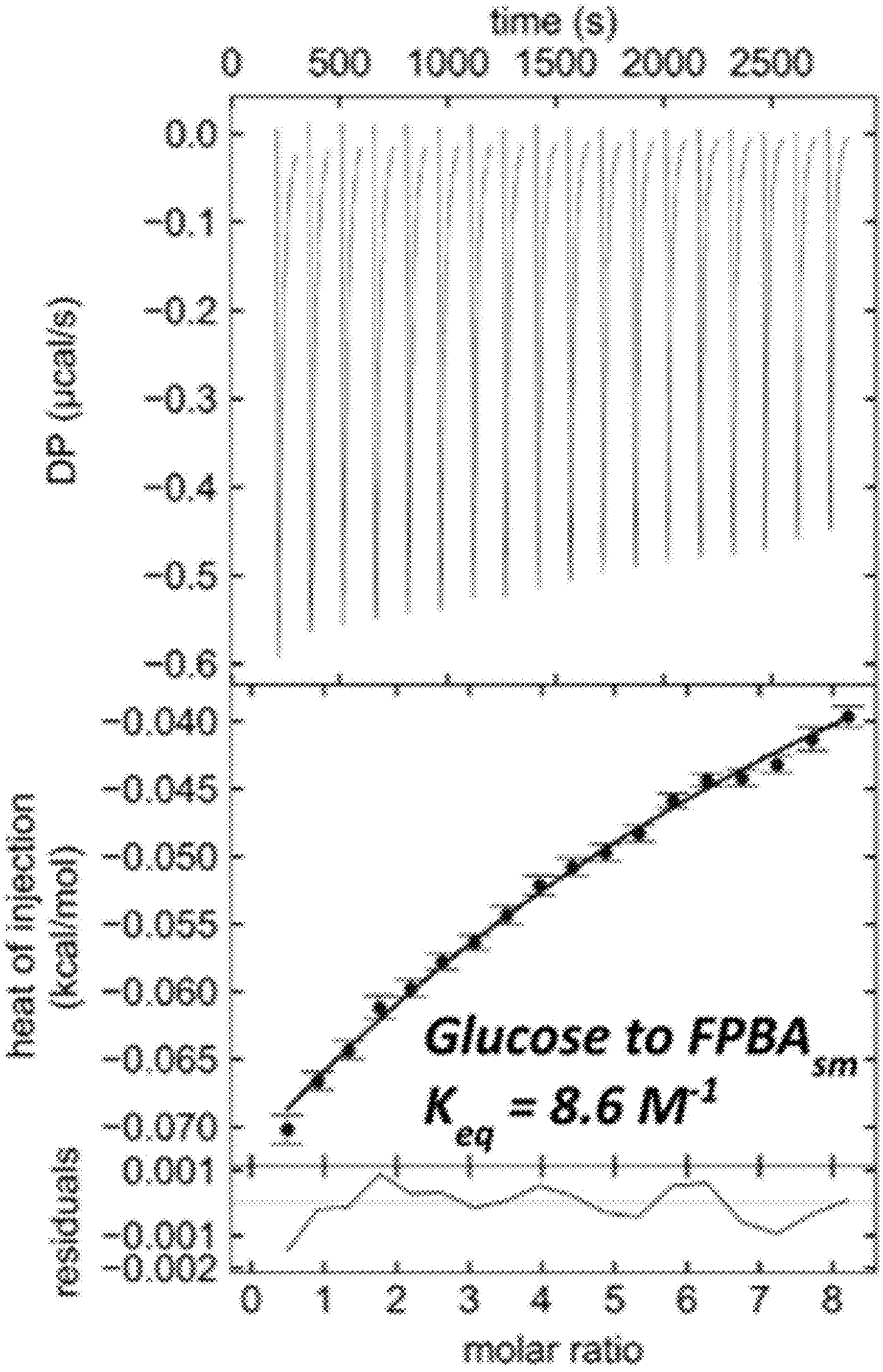
Figure 6A:
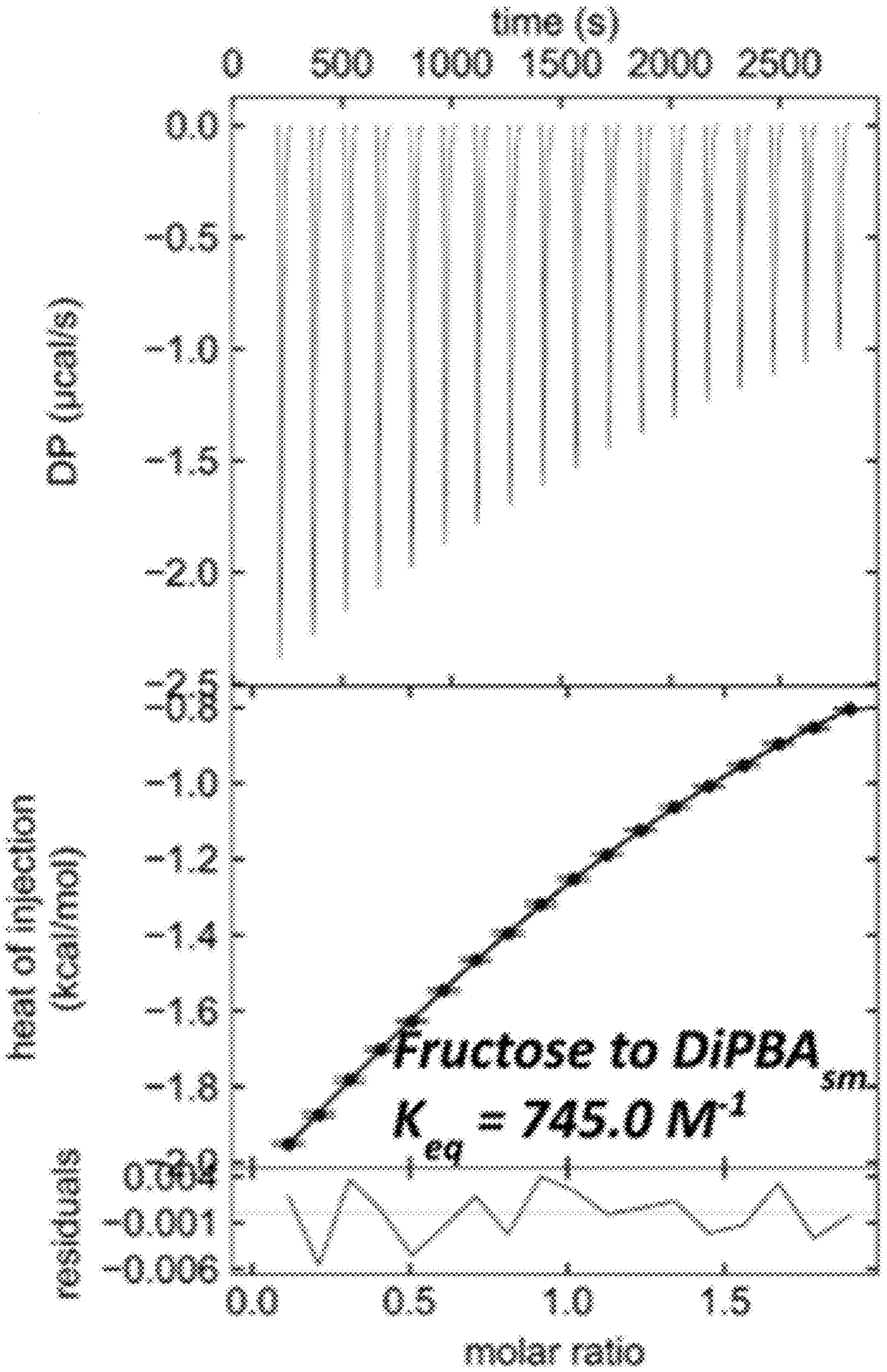
FIG. 6A-C show isothermal titration calorimetry (ITC) data from titrating fructose into small molecules of DiPBA ($DiPBA_{sm}$, FIG. 6A), PyPBA ($PyPBA_{sm}$, FIG. 6B), and FPBA ($FPBA_{sm}$, FIG. 6C).
Figure 6B:
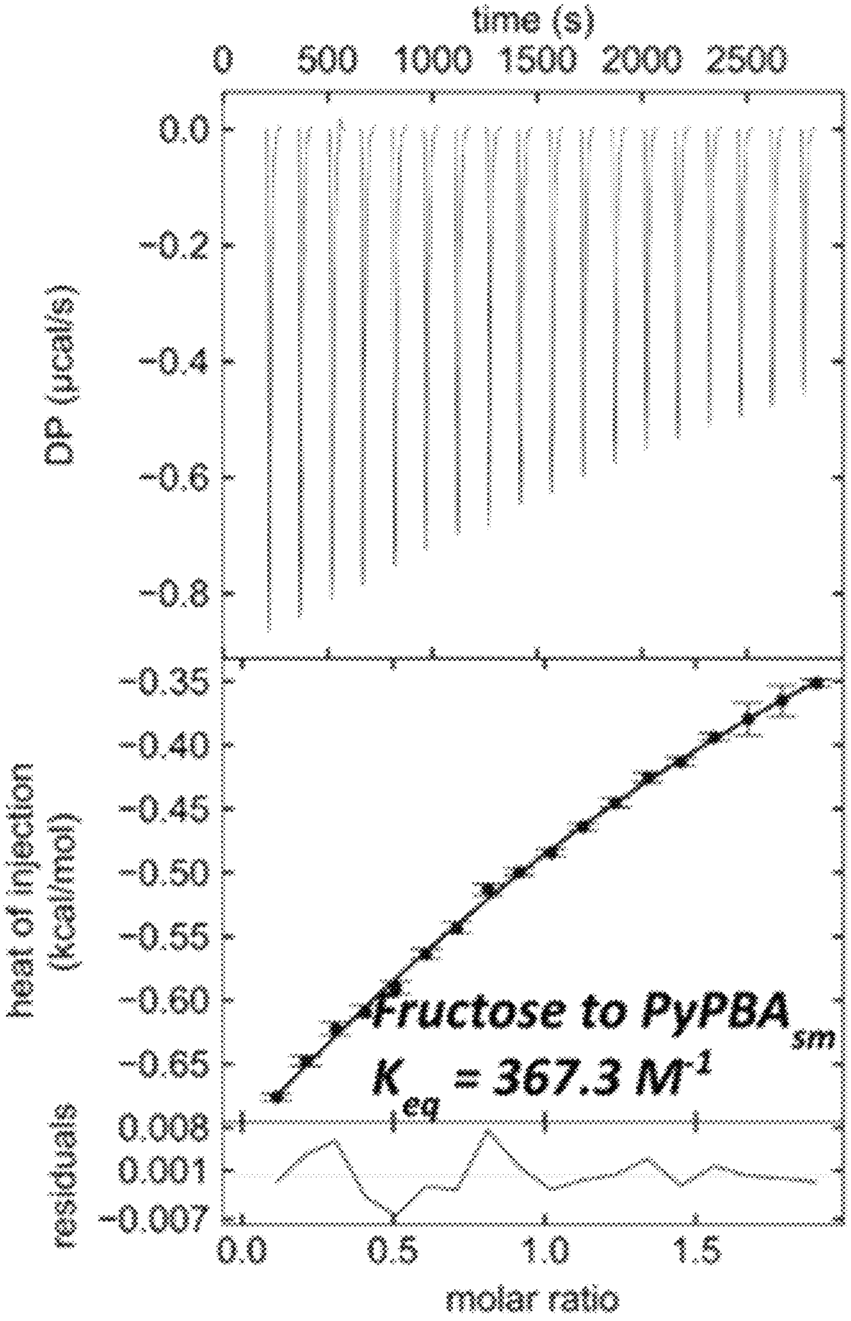
Figure 6C:
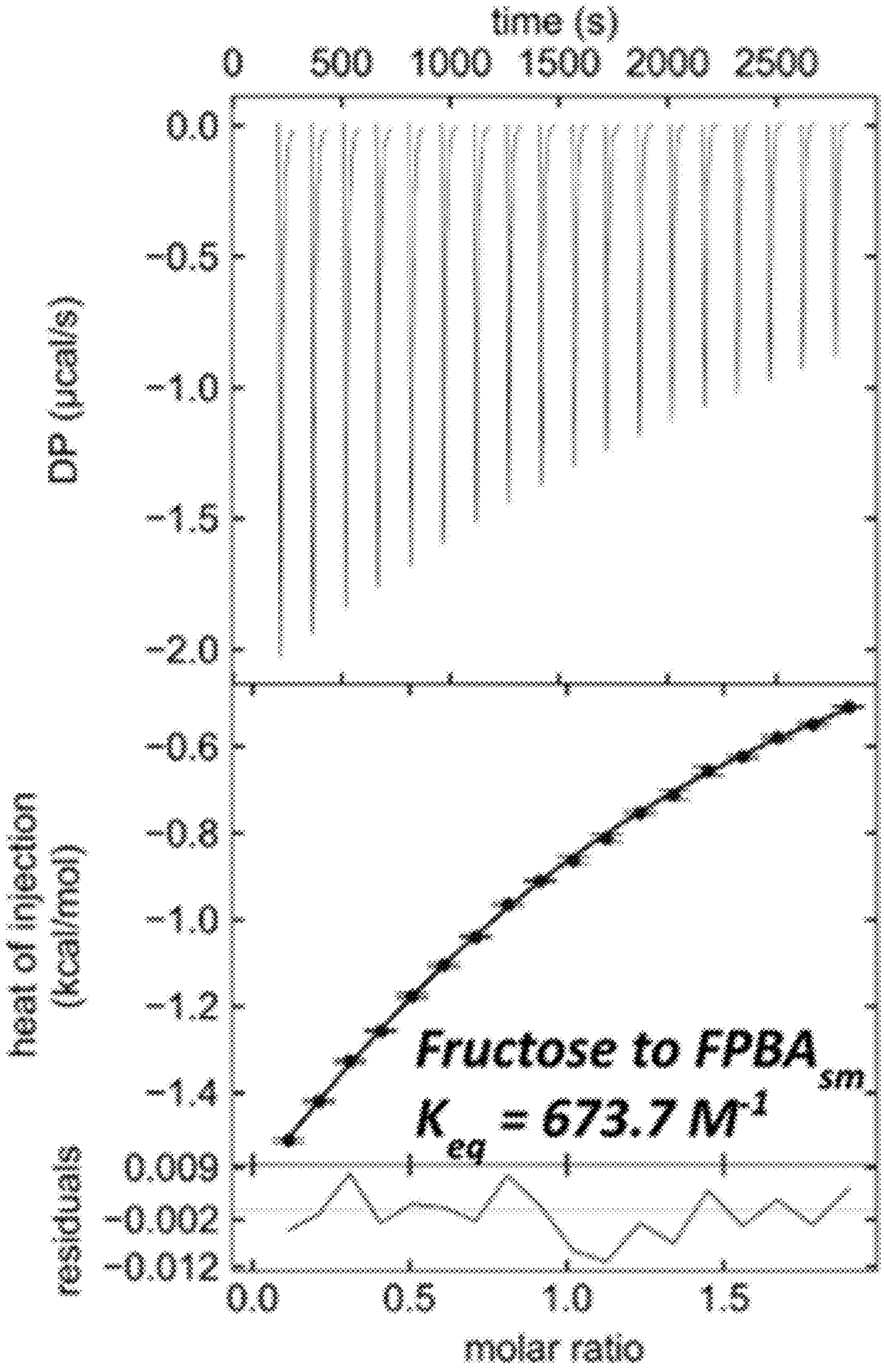
Figure 7A:
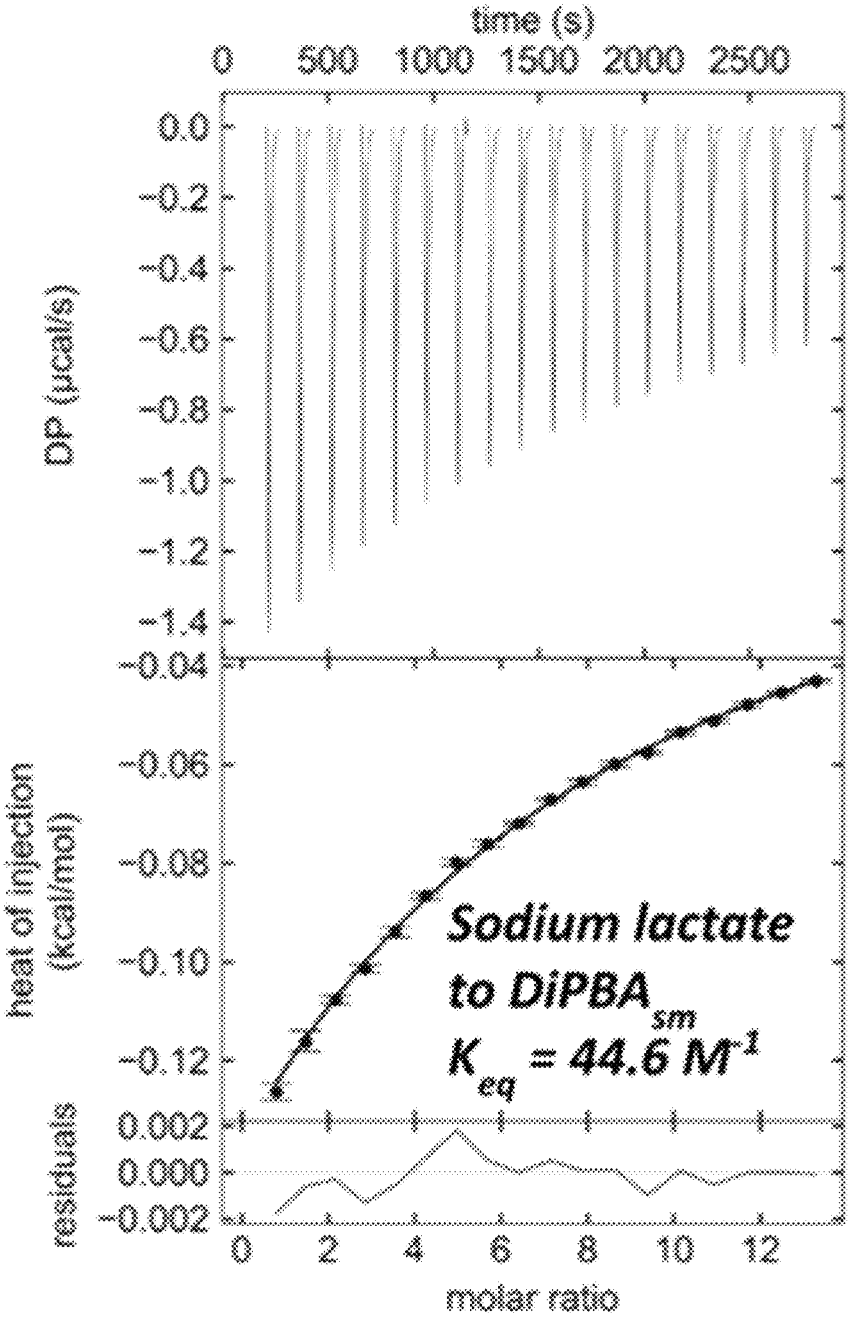
FIG. 7A-C show isothermal titration calorimetry (ITC) data from titrating sodium lactate into small molecules of DiPBA ($DiPBA_{sm}$, FIG. 7A), PyPBA ($PyPBA_{sm}$, FIG. 7B), and FPBA ($FPBA_{sm}$, FIG. 7C).
Figure 7B:
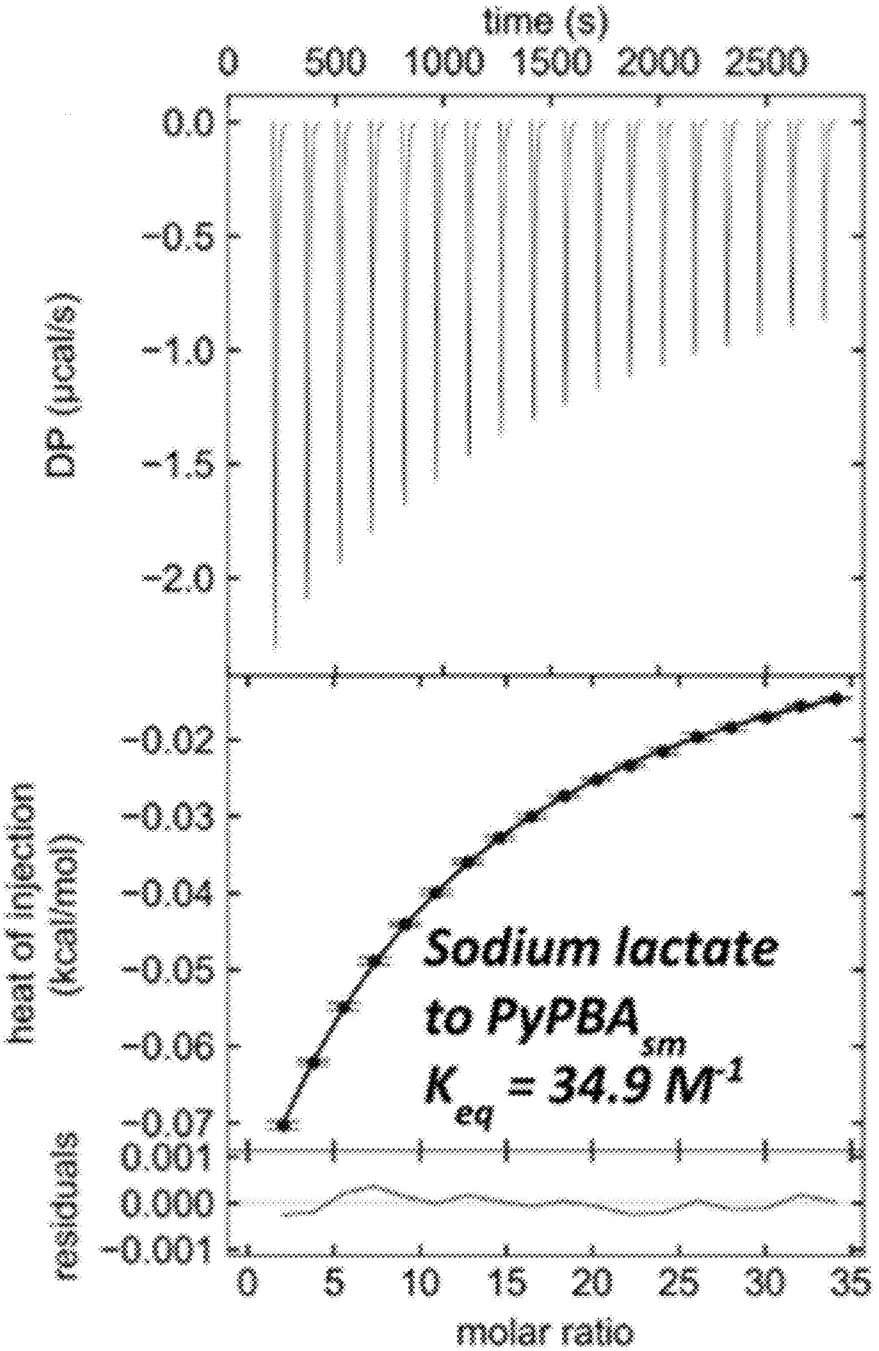
Figure 7C:
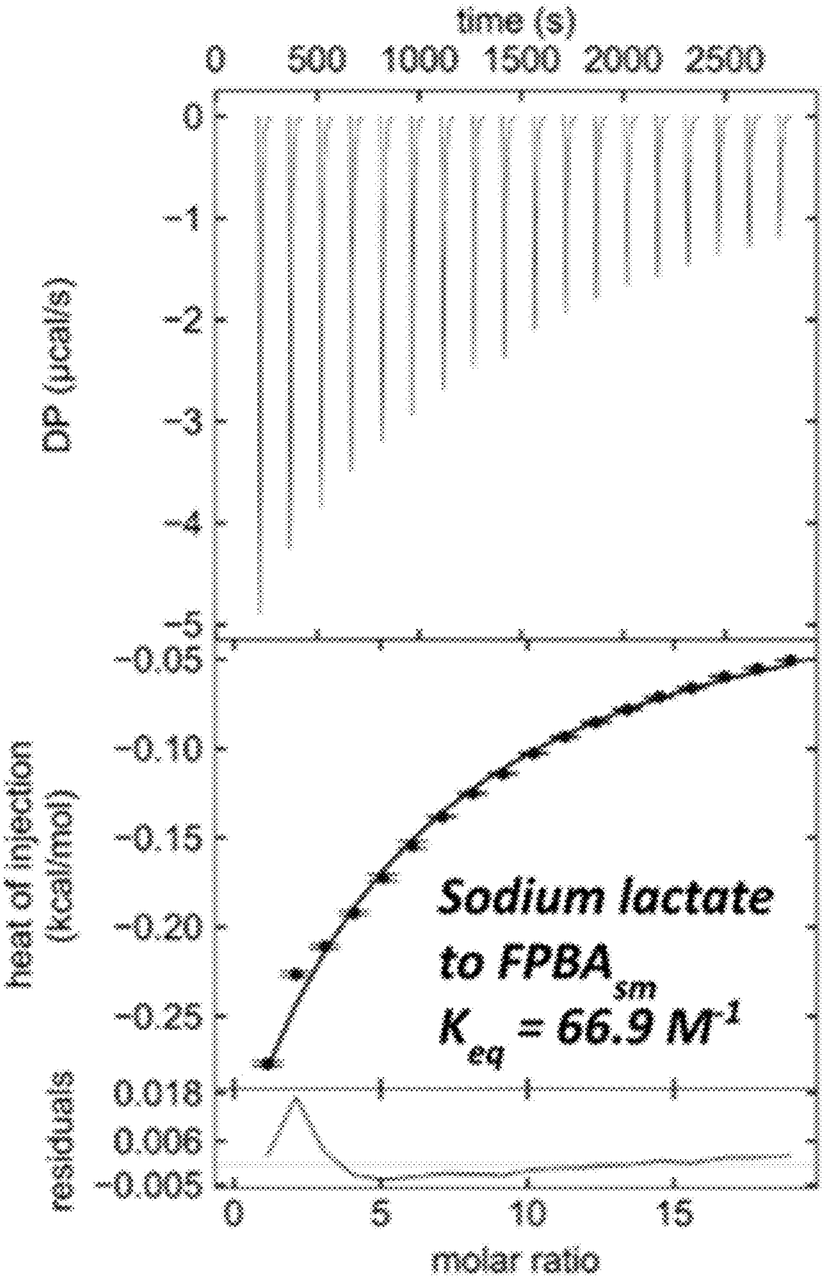
Figure 8A:
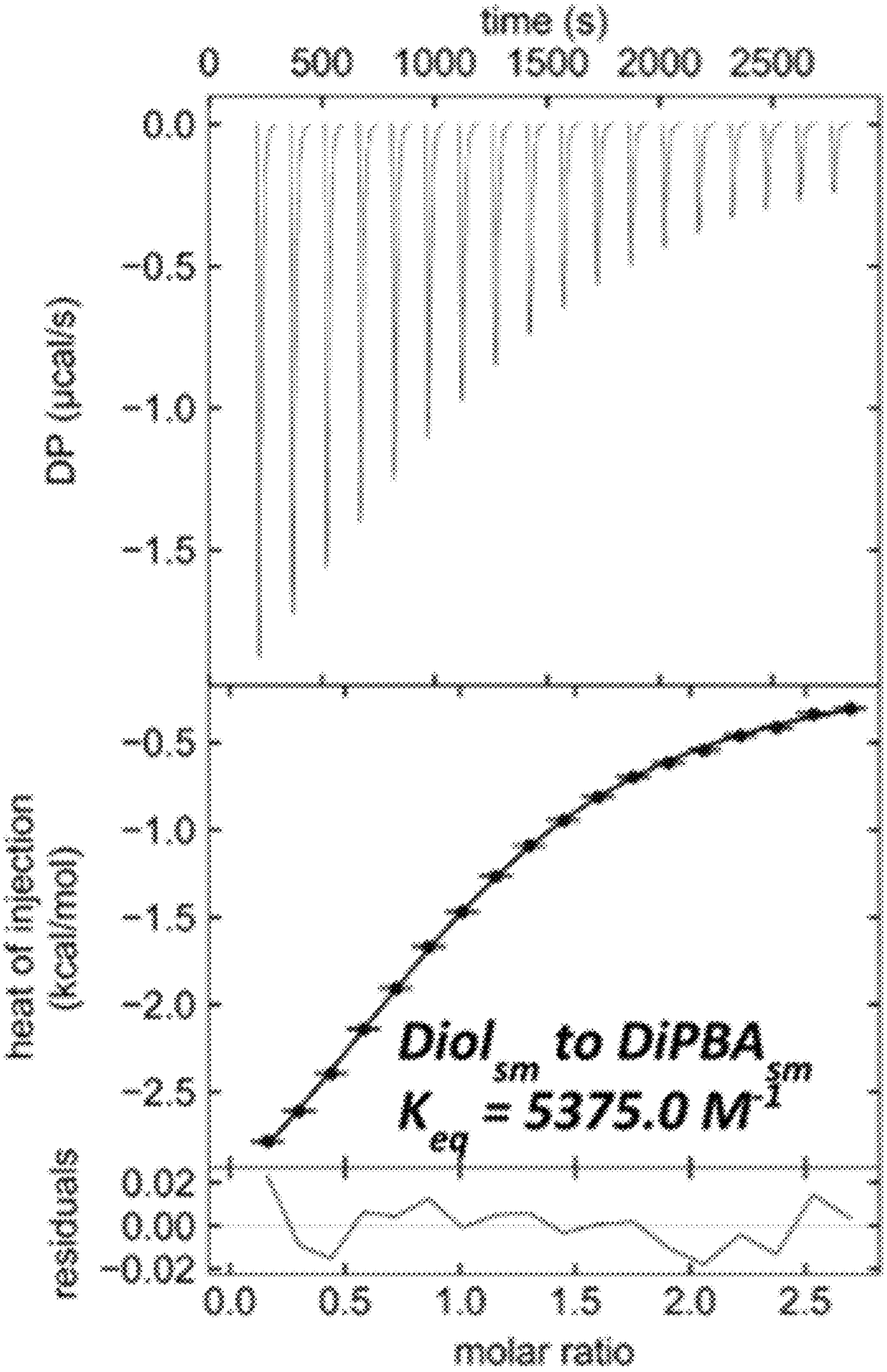
FIG. 8A-C show isothermal titration calorimetry (ITC) data from titrating GdL-diol into small molecules of DiPBA ($DiPBA_{sm}$, FIG. 8A), PyPBA ($PyPBA_{sm}$, FIG. 8B), and FPBA ($FPBA_{sm}$, FIG. 8C).
Figure 8B:
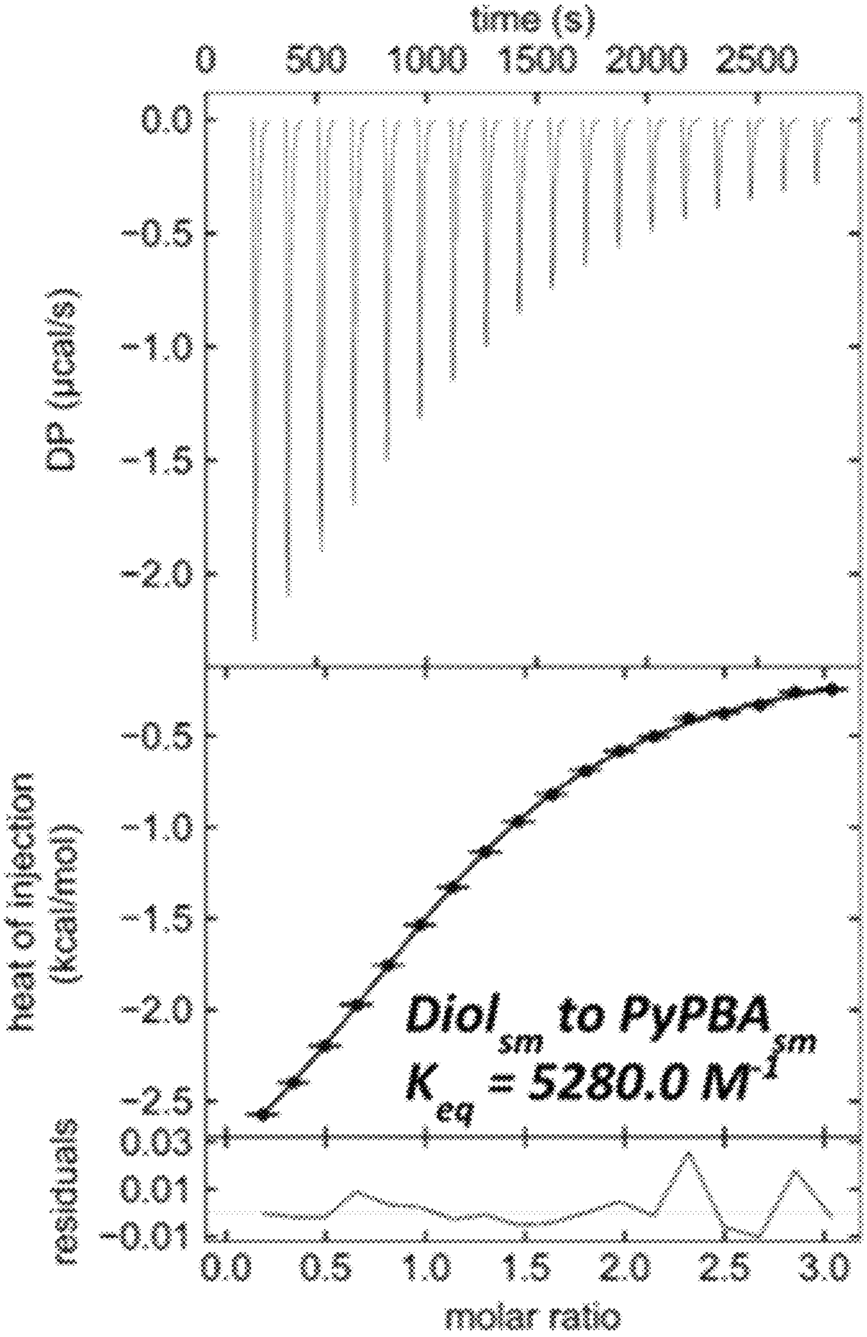
Figure 8C:
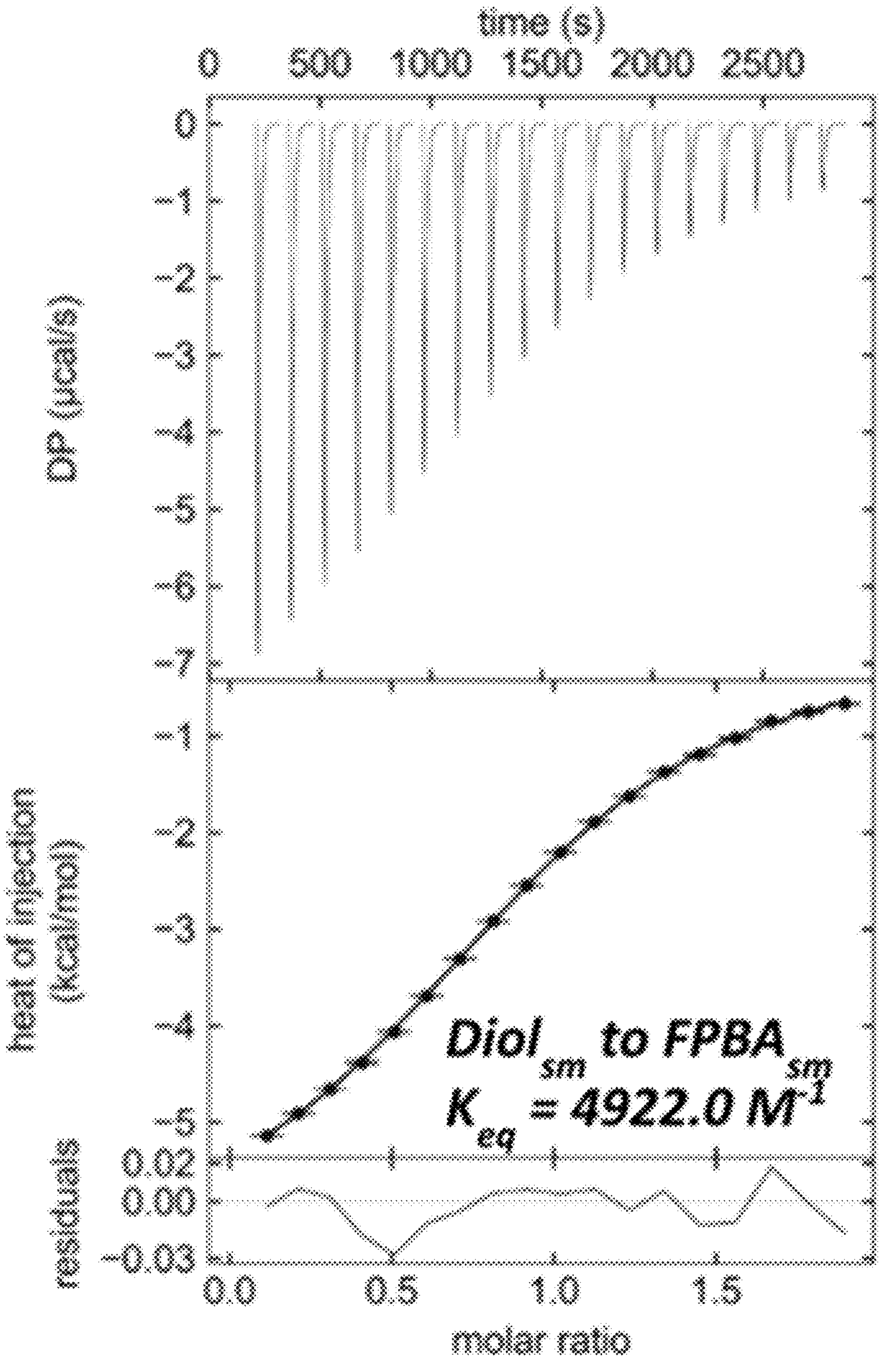

With modified 4aPEG macromers prepared, ideal network hydrogels prepared from these macromers were next evaluated. Dynamic-covalent hydrogels were prepared over a range of macromer concentrations by combining equimolar Diol-4aPEG with each of the PBA-modified 4aPEGs for oscillatory rheology, first performing a strain sweep to verify the linear viscoelastic region and then performing a frequency sweep at constant strain of 3% (FIG. 4B). These data reveal highly dynamic networks, with a time constant of network relaxation (TR) estimated to be ~7 s for the DiPBA-diol network on the basis of the G'/G" crossover frequency. Using a dynamic-modified phantom network model developed for related PBA-diol ideal networks to establish the effective affinity of PBA-diol network crosslinking, the $K_{eq}$ of binding for different PBA-modified 4aPEGs to Diol-4aPEG was determined to be 305 $M^{-1}$ (DiPBA), 309 $M^{-1}$ (FPBA), and 180 $M^{-1}$ (PyPBA) through model fitting (FIG. 4C). The magnitude of these values for $K_{eq}$ are consistent with results from work that developed this dynamic-modified phantom network model, also using 4aPEG materials crosslinked by PBA-diol interactions (~275 $M^{-1}$). Notably, the values derived when applying this model to the present networks were ~1 order of magnitude lower than those determined from ITC binding studies between small molecule PBAs and GdL-diol. This difference is reasonable given that presentation of binding motifs on macromers is expected to reduce the rate of association ($k_{on}$) and increase the relative entropic penalty associated with bond formation when compared to interactions between small molecules. These studies further support comparable dynamic-covalent binding interactions for both DiPBA-4aPEG and FPBA-4aPEG to Diol-4aPEG, supporting a focused comparison between this new DiPBA motif with the traditional FPBA motif for the remainder of the studies presented in this work.

Figure 9A:
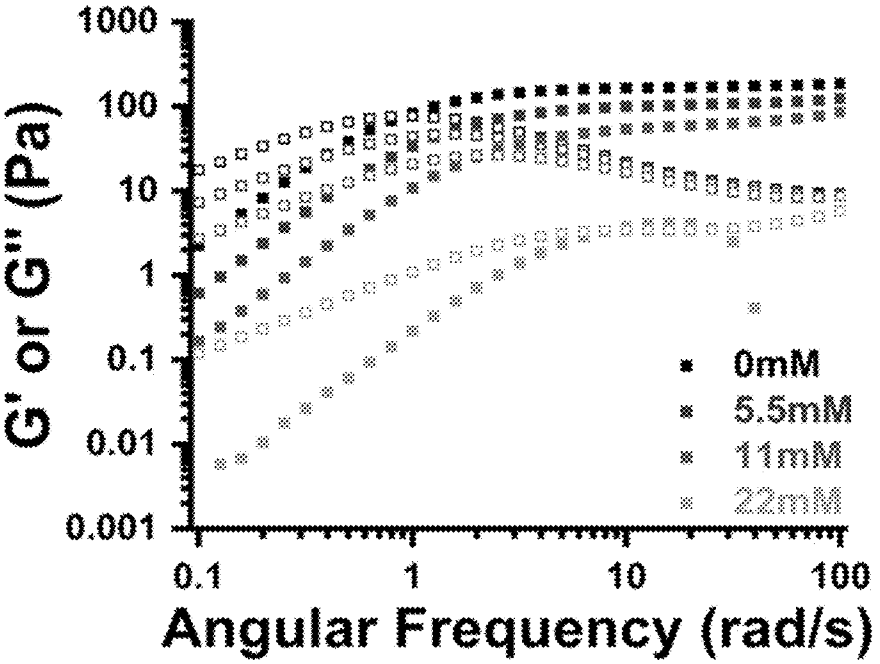
FIG. 9A-B show glucose-dependent oscillatory rheology frequency sweeps performed for networks crosslinked by DiPBA-Diol (FIG. 9A) or FPBA-Diol (FIG. 9B) dynamic-covalent interactions. Hydrogels were prepared at 2 mM macromer concentration in pH 7.4 buffer in all cases, with the addition of glucose at a concentration of 0, 5.5, 11, or 22 mM.
Figure 9B:
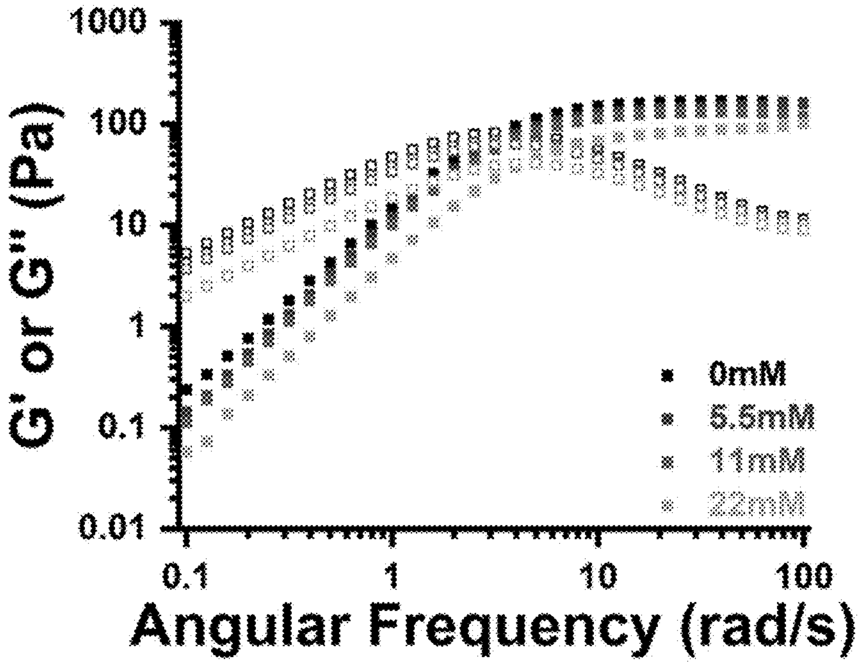

Glucose-dependent dynamic properties were next evaluated for these hydrogels using oscillatory rheology, comparing dynamic-covalent networks prepared from DiPBA-diol and FPBA-diol crosslinking. Hydrogels were formulated by mixing PBA-bearing 4aPEG macromers with equimolar Diol-4aPEG at a total polymer concentration of 2 mM (~2% w/v) in a pH 7.4 buffer containing various glucose concentrations (FIG. 9A). As glucose concentration increased, it was hypothesized that hydrogels would become weaker due to increased competition from glucose with the underlying dynamic-covalent crosslinks. Since DiPBA binds with a higher affinity to glucose than does FPBA, it was also expected that DiPBA hydrogels would be more sensitive to glucose since the analyte would better compete for DiPBA crosslinks at comparable concentrations. Glucose concentrations were selected to span a physiologically relevant range from normoglycemic levels of 5.5 mM (100 mg/dL) to hyperglycemic levels of 22 mM (400 mg/dL). When comparing G' values in the plateau region (20 rad/s) of these frequency sweeps (FIG. 9B), the DiPBA hydrogels demonstrated substantial reduction in their storage modulus. This result arises from an increased fraction of network crosslinks being disrupted, and thus less energy stored in the bonds of these networks under oscillatory deformation. At 22 mM glucose, this network effectively behaved as a sol. The FPBA hydrogels, by comparison, exhibited some glucose-responsive change in storage modulus though this effect was less dramatic than that observed for DiPBA; a stable hydrogel remained for FPBA in 22 mM glucose with only ~50% reduction in G' compared to the glucose-free case. Accordingly, the DiPBA hydrogel platform affords more dramatic glucose-responsive mechanical properties at physiological glucose concentrations. The underlying bond dynamics for the DiPBA hydrogels were likewise increased upon addition of glucose, with a shift in TR from 7 s (0 mM glucose) to 3 s (11 mM glucose). The increase in dynamics of network bonding is likewise expected due to increased competition from soluble glucose. In spite of glucose-responsive function being claimed in other reports of FPBA-diol ideal network hydrogels, these studies did not conduct any glucose-dependent rheological measurements and thus comparison of the effect observed here to prior work is not possible.

Figure 9C:
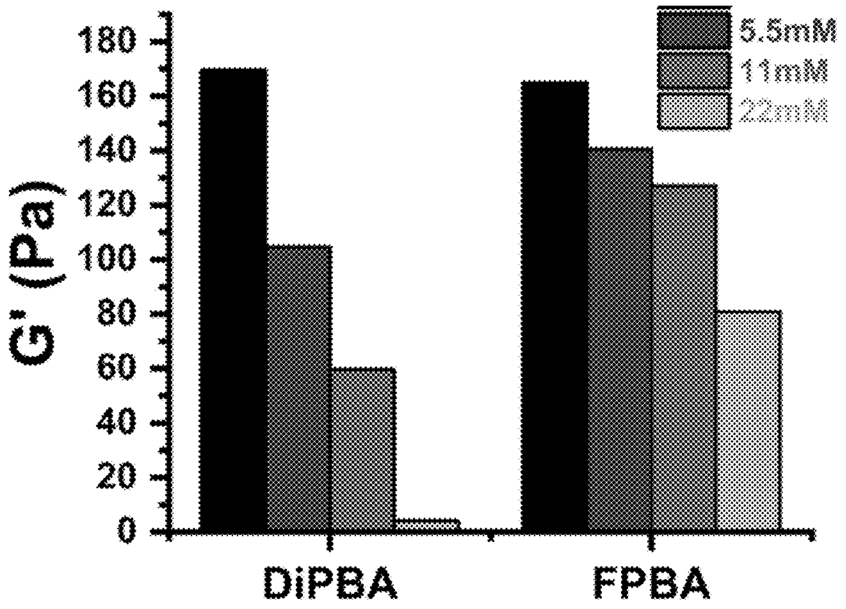
FIG. 9C shows G' (at 20 rad/s) for each hydrogel formulation at the various glucose concentrations.

After confirming glucose-responsive hydrogelation, controlled release of an encapsulated insulin payload was next assessed (FIG. 9C). Hydrogels were prepared in all cases from a 1:1 molar ratio of the PBA or DiPBA motif to diol at 2 mM total macromer concentration in pH 7.4 buffer. As hydrogels were being formed, fluorescently labeled insulin was included for entrapment in the network to study its glucose-responsive release. Each hydrogel was immersed in a bulk buffer containing different physiologically relevant glucose concentrations ranging from 2.3 mM (42 mg/dL) to 22 mM (400 mg/dL). Significant glucose-dependent function was demonstrated for the DiPBA hydrogel, evident in both its rate and amount of insulin release. Comparing the two glucose concentration extrema, the initial rate of release over the first 3 h increased from 0.08 $h^{-1}$ (2.3 mM) to 0.20 $h^{-1}$ (22 mM), while the total amount of insulin released at 8 h increased from 35% (2.3 mM) to 80% (22 mM). Though glucose-dependent differences were also evident in FPBA hydrogels, both the initial rate (0.10 $h^{-1}$ vs. 0.16 $h^{-1}$) and final amount (50% vs. 75%) of insulin release were less dependent on glucose concentration (again, 2.3 mM vs. 22 mM). It is noted that prior work using 10 wt % FPBA-diol hydrogels showed very limited glucose-responsive release of insulin (5.8 kDa), though differences were observed for the release of a much larger IgG (150 kDa) payload. Glucose-responsive release of p-galactosidase (465 kDa) was also shown for a related PBA-diol network at 10 wt %. Unlike these prior works, some glucose-responsive release of insulin was observed here using the FPBA-diol network, and this effect was improved using the DiPBA-diol network. It is hypothesized that this finding results from the lower polymer concentration (~2 wt %) used in these studies compared to prior work, improving the ability of glucose to compete with PEG-appended diols to shift the dynamic-covalent equilibrium and disrupt FPBA-diol crosslinking. To verify this point, limited glucose-responsive function—as previously reported for FPBA-diol hydrogels—was confirmed here for 10 wt % FPBA-diol hydrogels, whereas DiPBA-diol hydrogels maintained glucose-responsive function at this elevated polymer concentration.

Figure 9D:
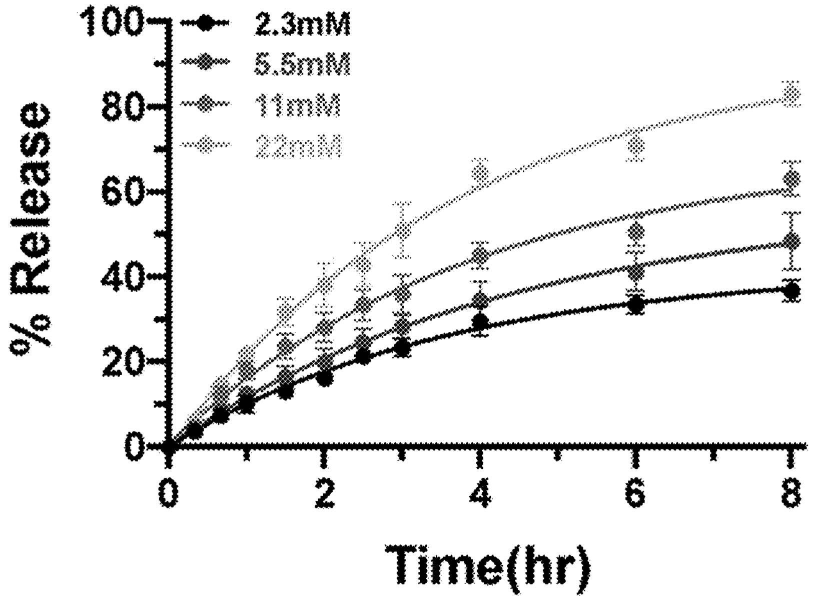
FIG. 9D-E show glucose-dependent release of FITC-insulin from hydrogels crosslinked by DiPBA-Diol (FIG. 3D) or FPBA-Diol (FIG. 3E) dynamic-covalent interactions. Hydrogels were prepared in a volume of 100 μL and 2 mM macromer concentration in 3.5 mL pH 7.4 buffer in all cases, with the addition of glucose in a bulk phase at concentrations of 2.3, 5.5, 11, or 22 mM. The data were fit to a standard first-order release model.
Figure 9E:
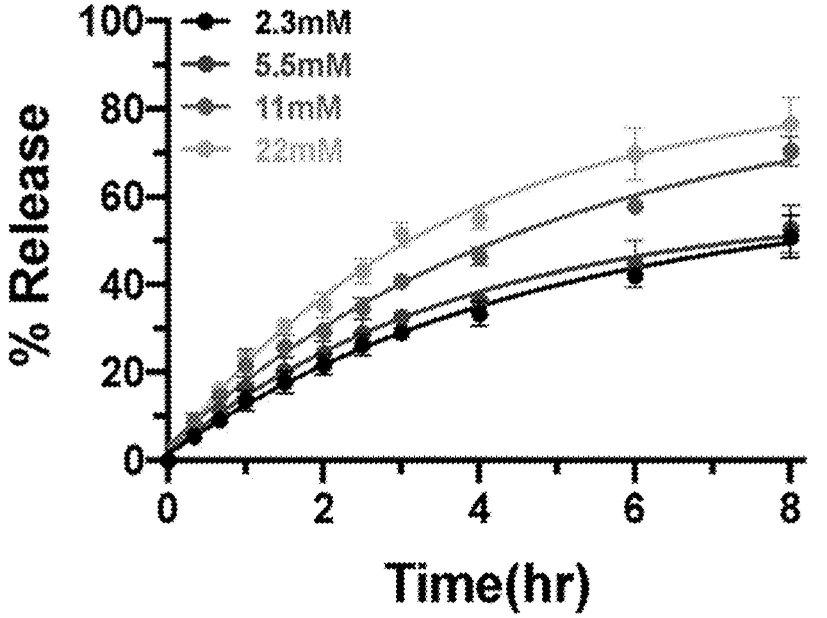
Figure 9F:
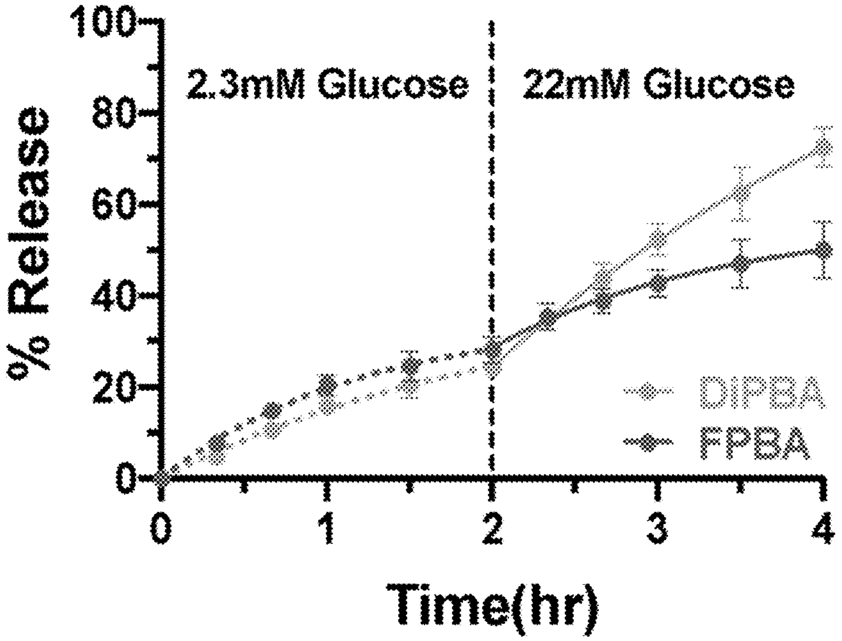
FIG. 9F shows step-change release, beginning with both DiPBA and FPBA hydrogels in a bulk glucose solution of 2.3 mM, with a complete exchange of the bulk buffer after 2 h to one containing 22 mM glucose. The data for each phase were fit to a standard first-order release model.

To improve function in blood glucose control, accelerated insulin release upon an increase in glucose level—as occurs following a meal—is a desirable property for a hydrogel depot. Accordingly, this function was assessed for hydrogels with encapsulated insulin by a sudden change in glucose concentration of the bulk release media (FIG. 9D). Over an initial time of 2 h, gels were immersed in a release buffer containing 2.3 mM glucose. In this time, FPBA hydrogels released 30% of encapsulated insulin compared to 25% released from DiPBA hydrogels. After 2 h, the buffer was exchanged for a buffer containing 22 mM glucose to mimic a sudden increase in blood glucose. Over the ensuing 2 h, the total release for the FPBA hydrogels increased from 30% to 55%, while the DiPBA hydrogels showed a marked increase in release from 25% to 70%. These findings demonstrate increased responsiveness for the DiPBA platform, rapidly accelerating insulin release upon a sudden increase in glucose concentration.

Figure 10A:
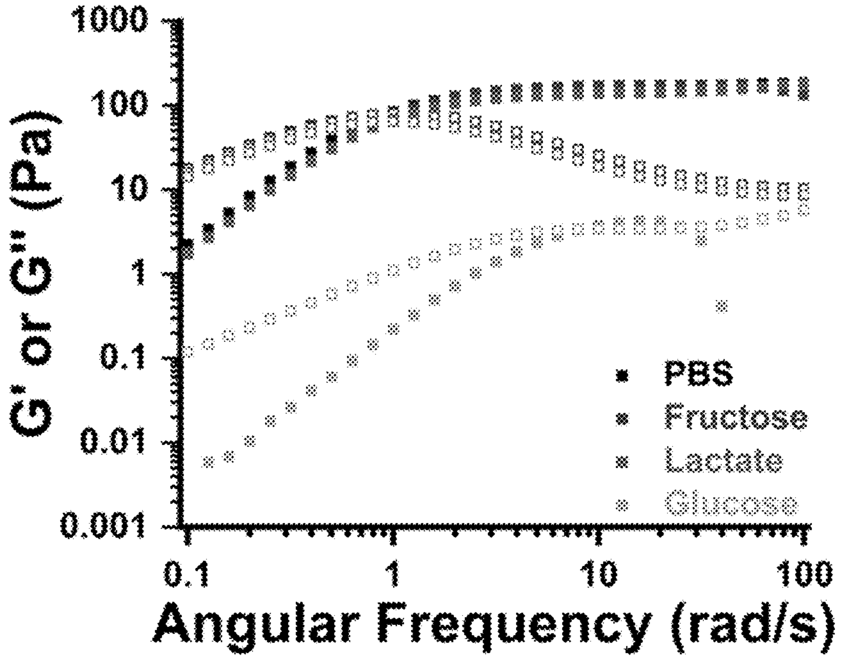
FIG. 10A-B show analyte-dependent oscillatory rheology frequency sweeps performed for networks crosslinked by DiPBA-Diol (FIG. 10A) or FPBA-Diol (FIG. 10B) dynamic-covalent interactions. Hydrogels were prepared at 2 mM macromer concentration in pH 7.4 buffer in all cases, with the addition of no analyte (PBS), fructose (1 mM), sodium lactate (5 mM), or glucose (22 mM).
Figure 10B:
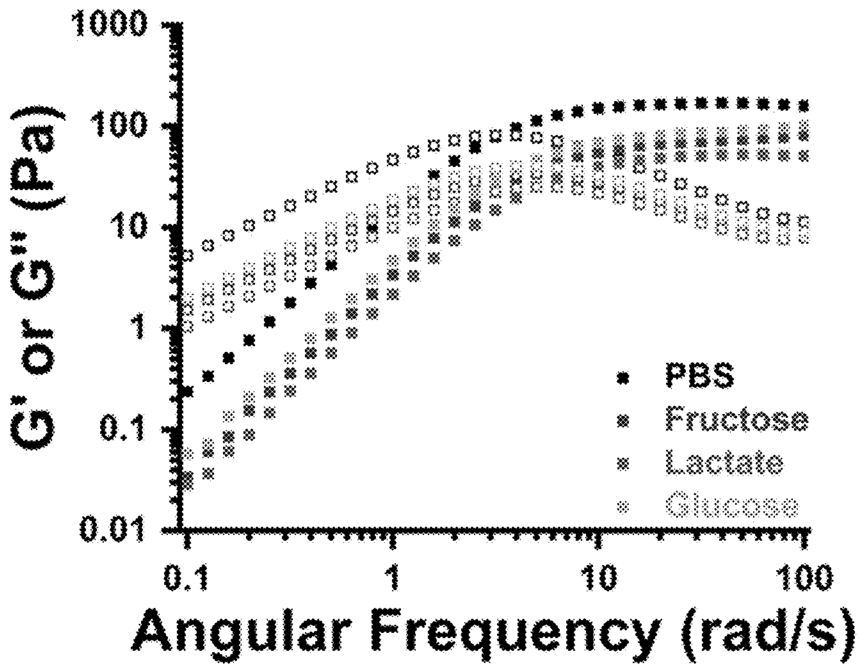

After establishing and comparing the relative glucose-responsive function for these hydrogels, their interaction with non-glucose analytes was next evaluated. Hydrogels were formulated at 2 mM (~2 wt %) macromer concentration, as before, with different amounts of competing analytes. From the initial ITC results, it was hypothesized that the DiPBA hydrogel should be less sensitive to crosslink disruption by non-glucose analytes than would the FPBA hydrogel. The concentrations of the competing analytes studied were 1 mM for fructose and 5 mM for lactate, selected to be on the upper end of their physiologically relevant range of exposure. These results were compared to the hydrogel response resulting from incubation with 22 mM glucose, also on its upper end of diabetic physiological exposure concentration. Oscillatory rheology was performed as before (FIG. 10A), and G' values in the plateau region (20 rad/s) were compared directly for each hydrogel formulation with each analyte (FIG. 10B). These results point to limited responsiveness of the DiPBA hydrogel to 5 mM lactate (G'=143 Pa) and 1 mM fructose (G'=174 Pa) compared to 22 mM glucose (G'=4 Pa, sol). These results support the glucose specificity of DiPBA crosslinking chemistry relative to its response to non-glucose analytes present at their physiological concentrations. The FPBA hydrogel, by comparison, responded comparably to lactate (G'=48 Pa) and fructose (G'=66 Pa) as it did to glucose (G'=81 Pa), indicating no glucose specificity of the crosslinking mechanism in this platform.

Figure 10C:
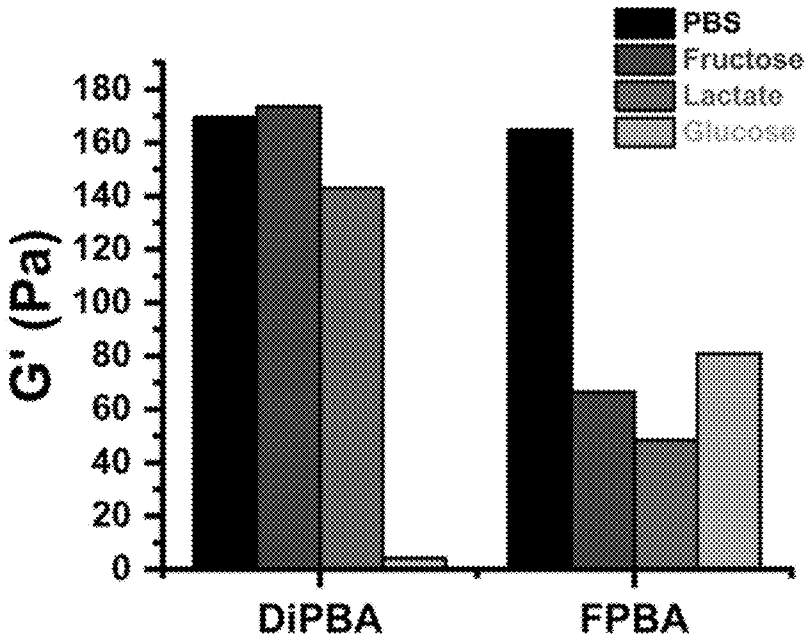
FIG. 10C shows G' (at 20 rad/s) for each hydrogel formulation when exposed to the various analytes.

In the context of insulin therapy, interference from lactate presents an especially problematic outcome for a delivery depot; whereas fructose arises from dietary sources and typically overlaps with glucose consumption and insulin need, lactate is frequently elevated during and after periods of vigorous exercise. Lactate is also known to be elevated in diabetics with poorly managed disease. Thus, the impact of lactate was further explored for its role in triggering undesired insulin release from PBA-diol hydrogels (FIG. 10C). DiPBA-4aPEG or FPBA-4aPEG macromers were mixed with equimolar Diol-4aPEG at 2 mM total macromer concentration and incubated in a buffer containing physiologically relevant glucose and lactate concentrations. Four conditions were selected, combining glucose that was either normal (5 mM) or slightly elevated (10 mM) with physiologically relevant lactate levels mimicking normal (0.5 mM) and elevated (5 mM) states. The presence of lactate caused no significant enhancement in insulin release from DiPBA hydrogels; these instead had release profiles that were fully dictated by glucose level but independent of the addition of either normal or high levels of lactate. The FPBA hydrogels, conversely, showed increased release in response to increases in both glucose and lactate. These findings corroborate data demonstrated previously in both ITC and rheology studies that show FPBA-lactate binding and lactate-driven network disruption, respectively.

Figure 10D:
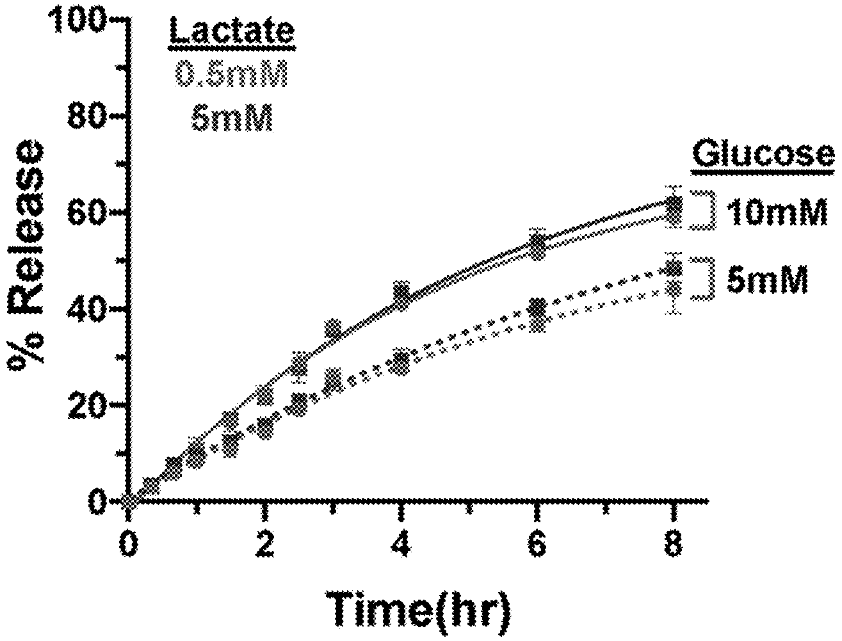
FIG. 10D-E show glucose- and lactate-dependent release of FITC-insulin from hydrogels crosslinked by DiPBA-Diol (FIG. 10D) or FPBA-Diol (FIG. 10E) dynamic-covalent interactions. Glucose concentration was either normal (5 mM, dashed) or moderately elevated (10 mM, solid), while lactate was either normal (0.5 mM, teal) or elevated (5 mM, magenta). Hydrogels were prepared in a volume of 100 μL and 2 mM macromer concentration in 3.5 mL pH 7.4 buffer in all cases, with the addition of glucose and lactate in the bulk phase at the concentrations indicated. The data were fit to a standard first-order release model.
Figure 10E:
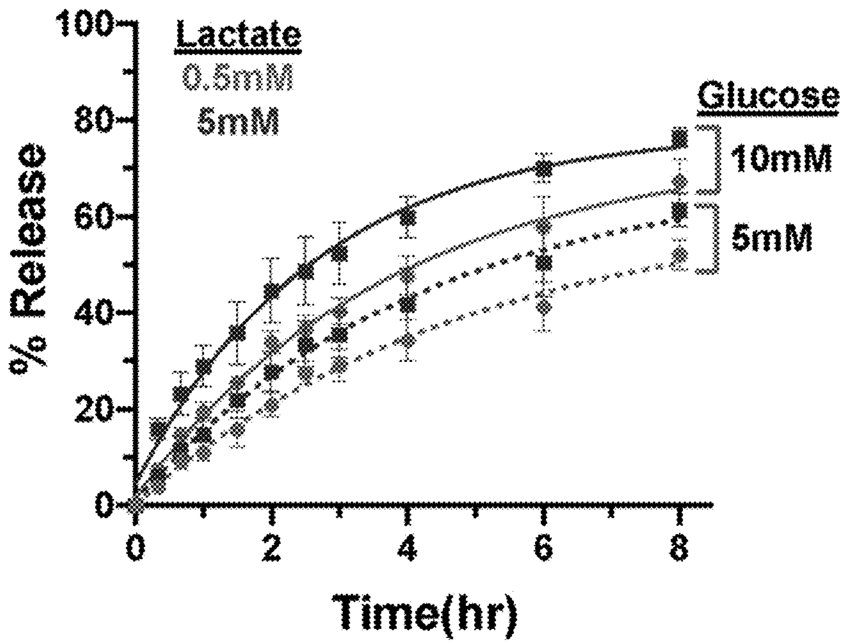
Figure 10F:
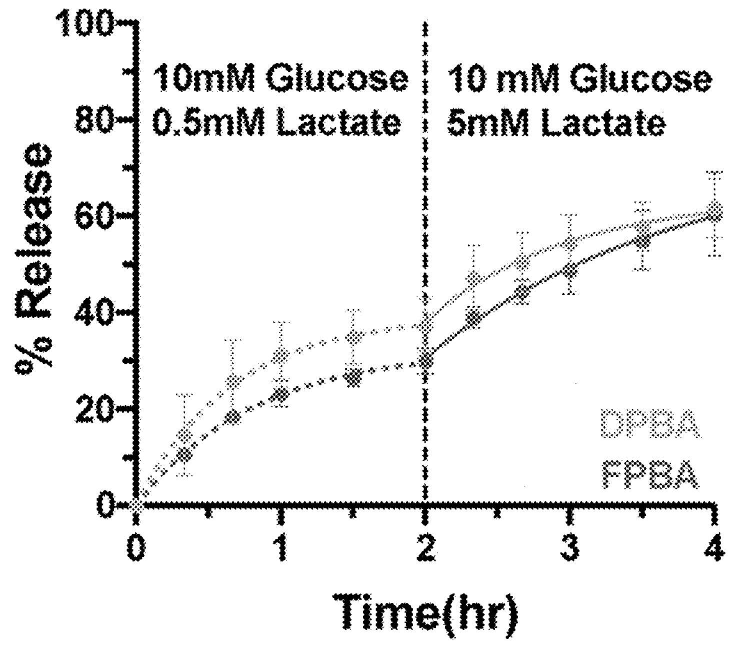
FIG. 10F shows step-change release, beginning with both DiPBA and FPBA hydrogels in a bulk glucose solution of moderately elevated glucose (10 mM) and normal lactate (0.5 mM), with a complete exchange of the bulk buffer after 2 h to one containing the same glucose concentration (10 mM) but elevated lactate (5 mM). The data for each phase were fit to a standard first-order release model.

As lactate levels may rise quickly with vigorous exercise, this scenario was recreated by studying the change in insulin release upon a sudden change in an environment of stable and slightly elevated glucose (10 mM) from low (0.5 mM) to high (5 mM) lactate levels (FIG. 10D). Hydrogels were immersed in a buffer containing 10 mM glucose and 0.5 mM lactate for an initial period of 2 h. Over this time, FPBA hydrogels released 30% of their insulin while DiPBA released 35%, confirming the increased glucose-responsiveness of the DiPBA platform observed previously at elevated glucose. After this initial period, the buffer was then exchanged for a buffer that maintained the 10 mM glucose concentration but increased lactate levels to 5 mM. Over this additional 2 h period at elevated lactate, FPBA hydrogels released an additional 40% of encapsulated insulin, while DiPBA hydrogels released only an additional 25% of encapsulated insulin. These data further support the non-specific sensitivity of FPBA hydrogels, while release from DiPBA hydrogels is not substantially impacted by lactate as a physiologically relevant non-glucose analyte.

Figure 11A:
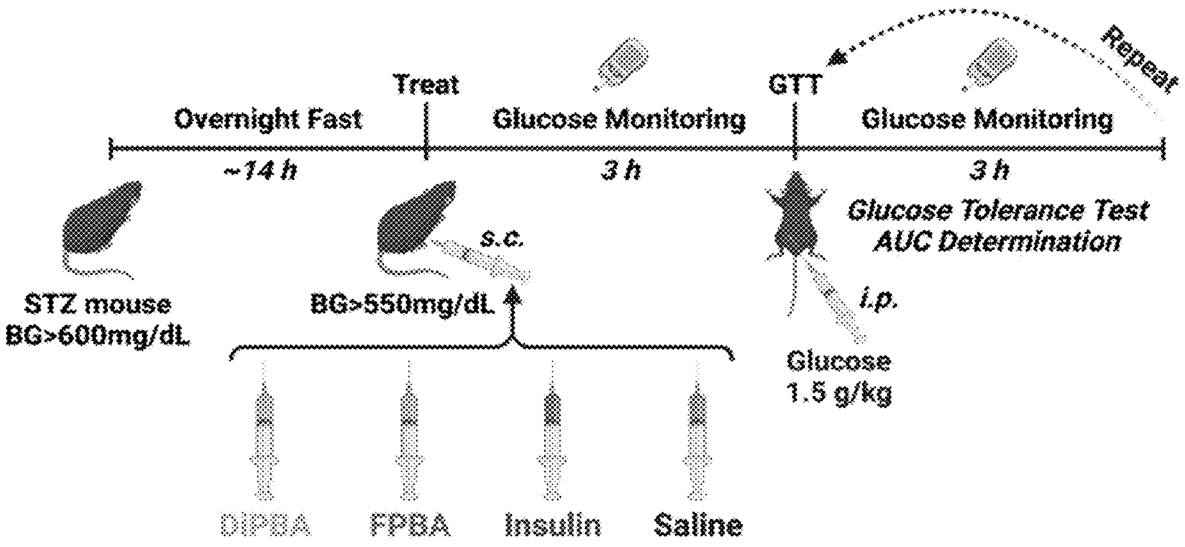
FIG. 11A shows a schematic overview of the experimental procedure to assess the glucose-responsive function of hydrogels in vivo, evaluating the hydrogels in streptozotocin (STZ)-induced diabetic mice with multiple intraperitoneal glucose tolerance tests (GTT).
Figure 11B:
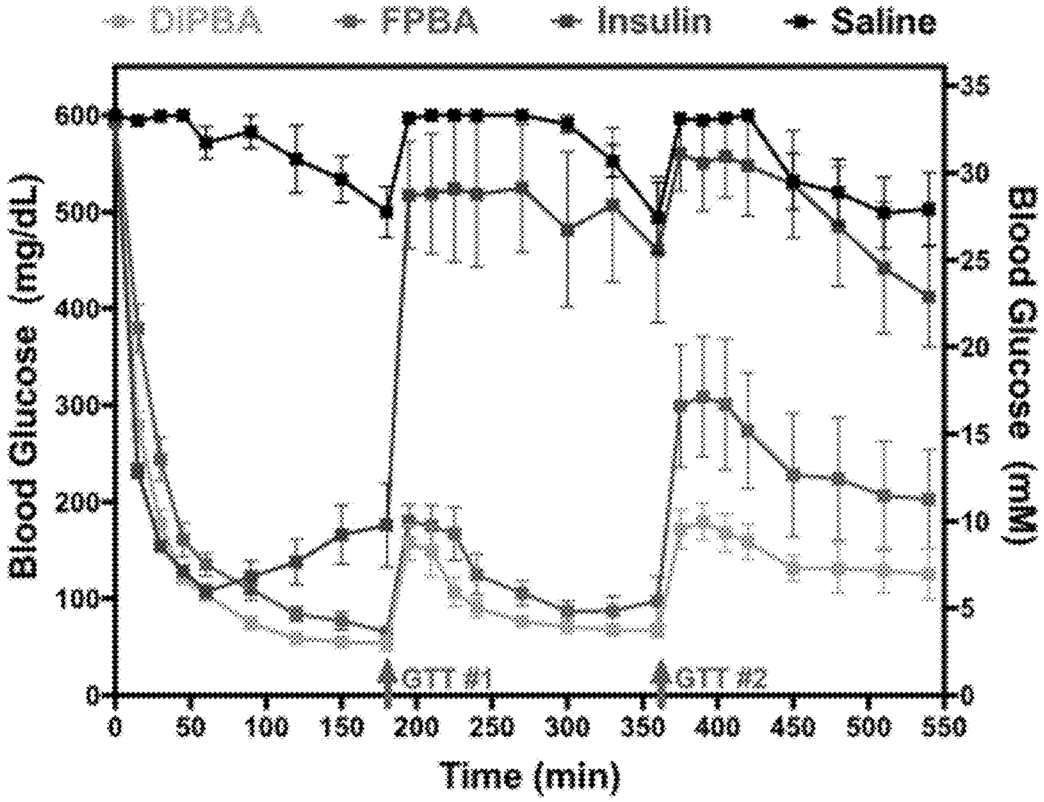
FIG. 11B shows blood glucose monitoring following therapeutic administration (t=0), including two glucose tolerance tests (t=180 and 360 minutes). Mice were randomized into treatment groups with n=5-6 per group.
Figure 11C:
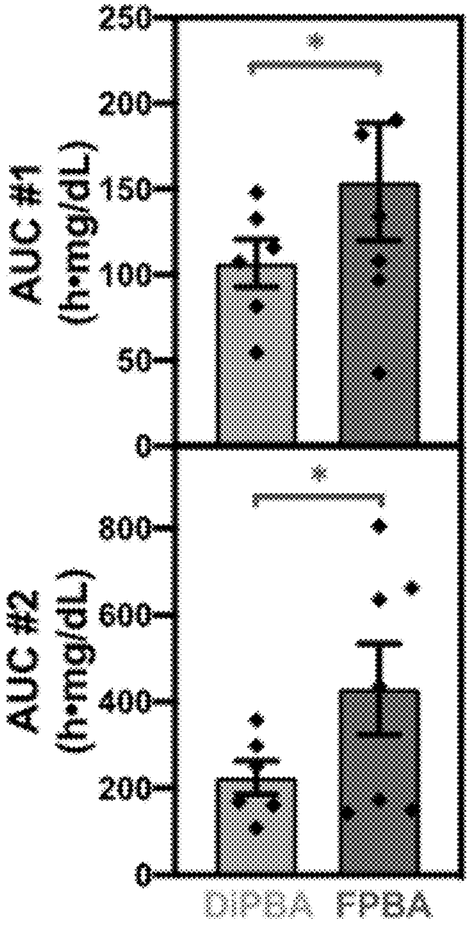
FIG. 11C shows the area under the curve (AUC) following each GTT was quantified by the trapezoidal method and compared for the two hydrogel formulations, with significance (*–P<0.05) determined using Student's t-test.
Figure 12A:
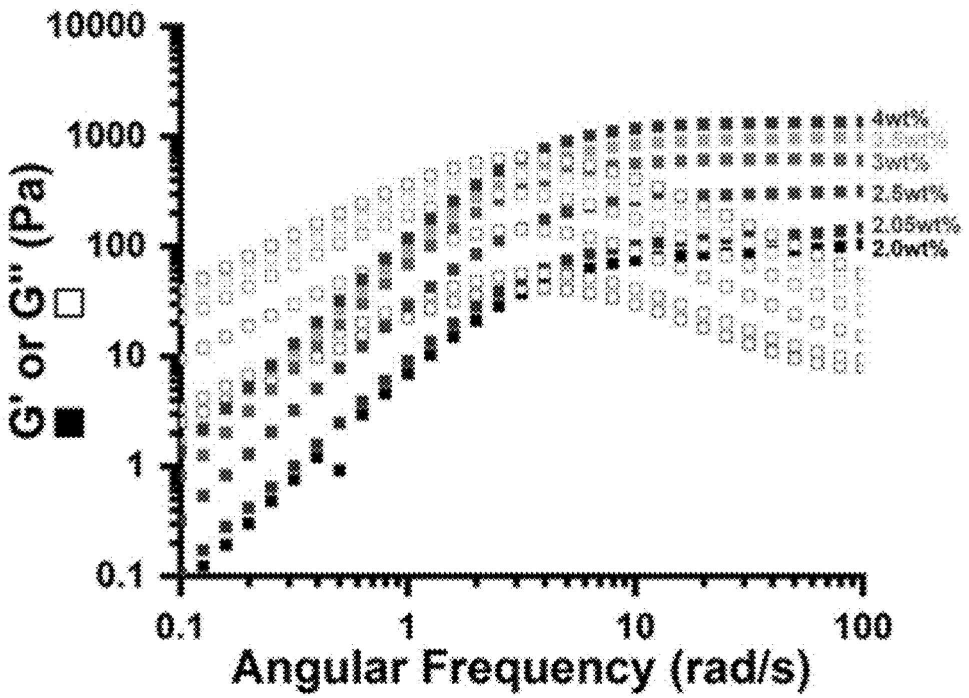
FIG. 12A-B show concentration-dependent frequency sweeps of hydrogel network prepared by 4aPEG-Diol and 4aPEG-FPBA (FIG. 12A) or 4aPEG-PyPBA (FIG. 12B).
Figure 12B:
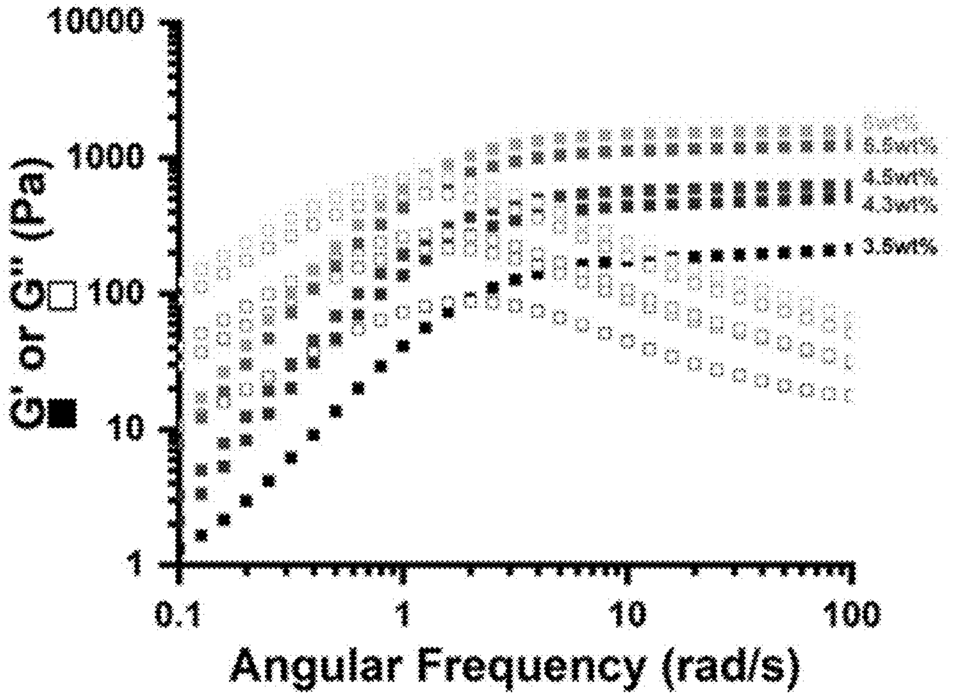
Figure 13:
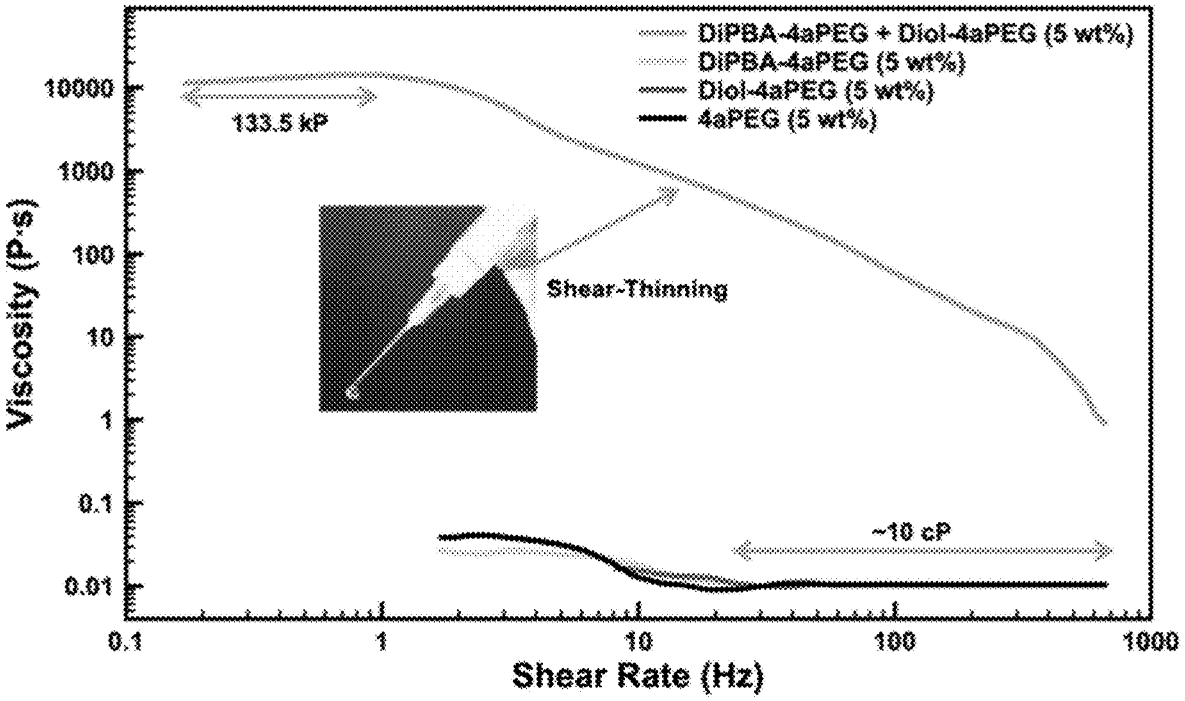
FIG. 13 shows shear viscosity measurements for 5 wt % samples of DiPBA-4aPEG, Diol-4aPEG, 4aPEG-OH, and a hydrogel prepared from mixing equimolar DiPBA-4aPEG with Diol-4aPEG at a total concentration of 5 wt %. The inset photograph illustrates the shear-thinning "injectability" evidenced in shear viscosity data.
Figure 14A:
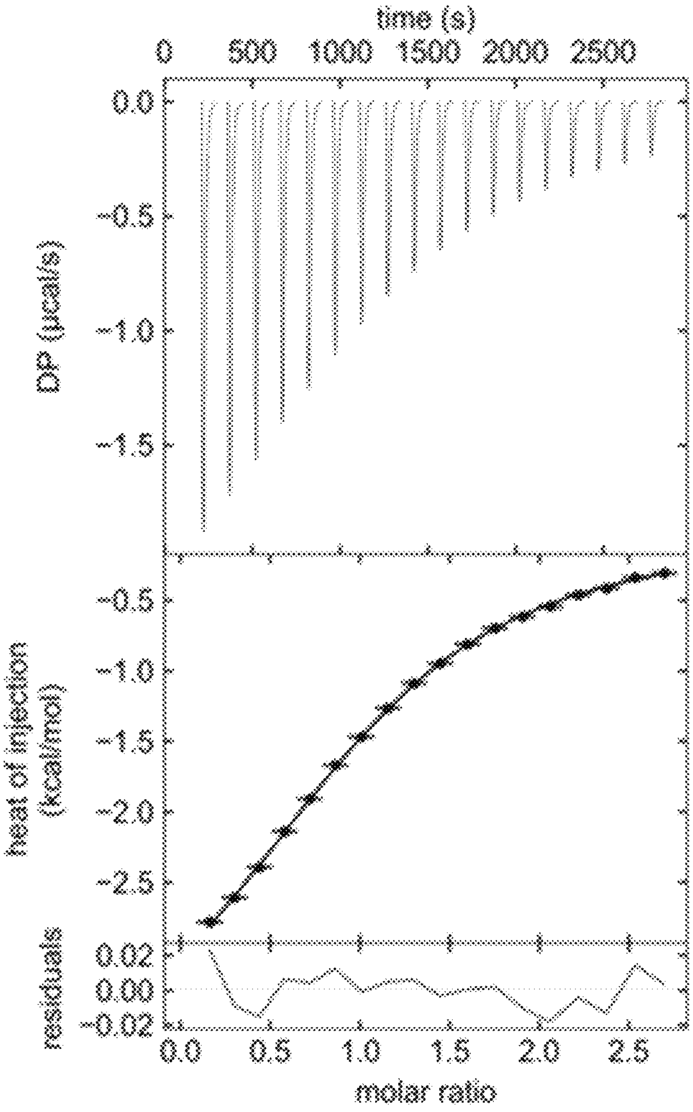
FIG. 14A-B show ITC results comparing DiPBA-diol interactions on small molecules (FIG. 14A) compared to those pendant from 5 kDa mPEG linear polymers (FIG. 14B).
Figure 14B:
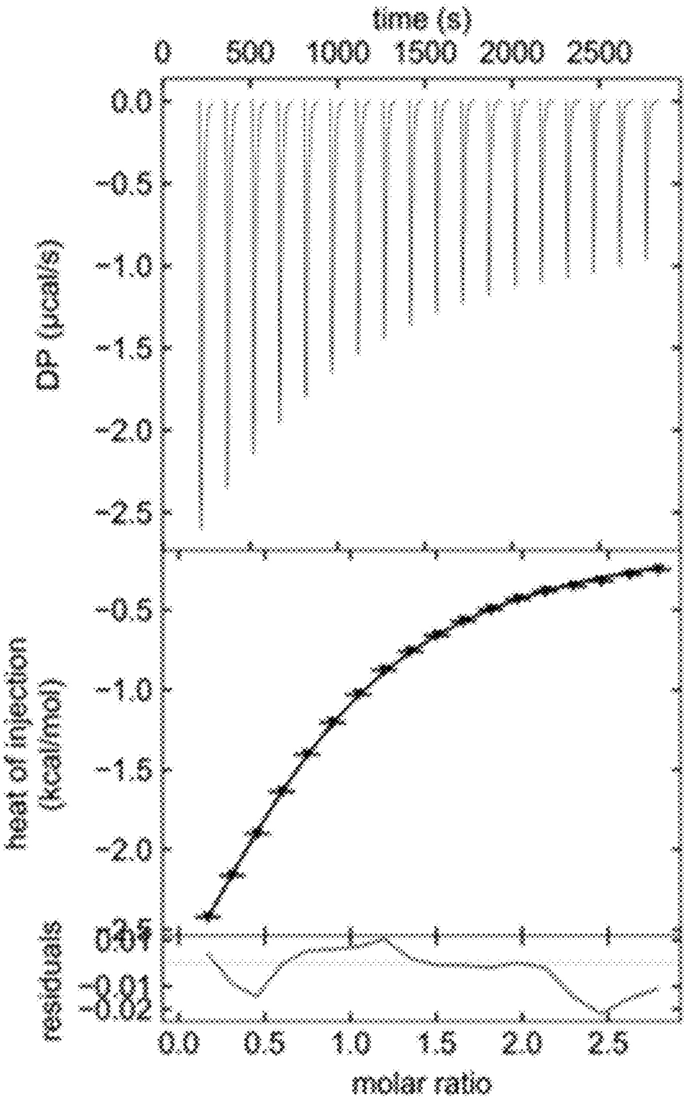
Figure 15A:
FIG. 15A-B show photographs of DiPBA and FPBA networks.
Figure 15B:
Figure 16:
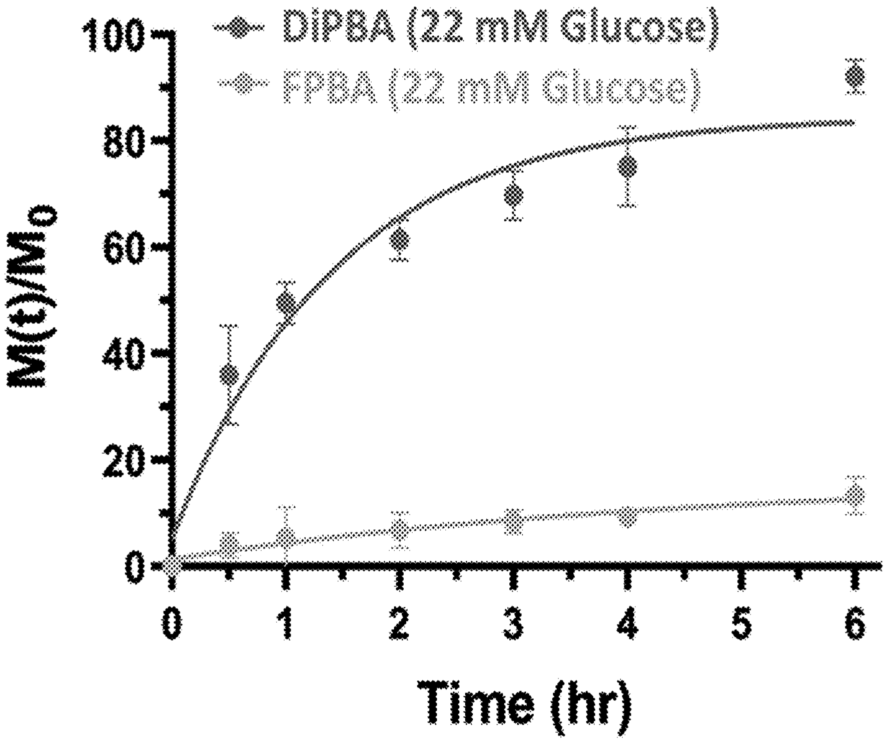
FIG. 16 shows hydrogel erosion quantified by measuring the mass loss, M(t), over time for DiPBA and FPBA hydrogels exposed to 22 mM glucose.
Figure 17A:
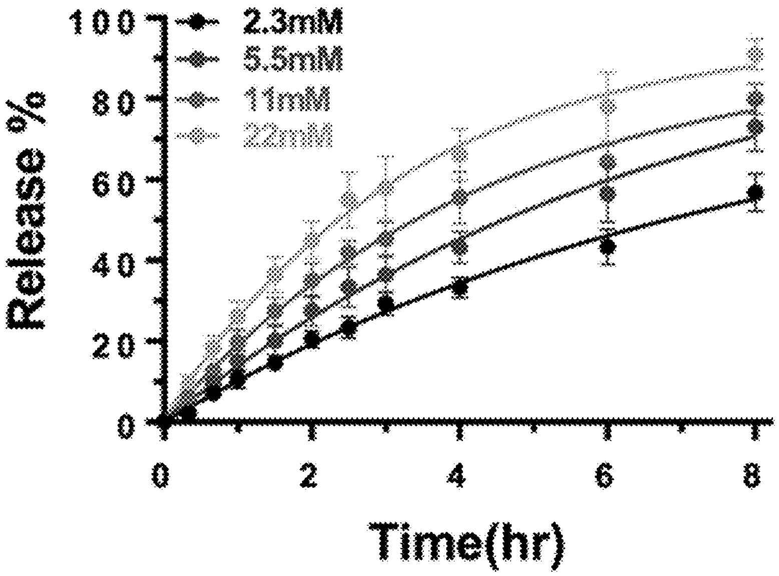
FIG. 17A-B show the glucose-dependent release profile of insulin from 10 wt % DiPBA (FIG. 17A) and 10 wt % FPBA gels (FIG. 17B). This study was conducted with modified methods; the release from hydrogels into a bulk buffer was measured without using molds noted in the methodological details for other release studies. This was possible with more robust 10 wt % hydrogels and done to better align with methods of Yesilyurt et al. *Adv. Mater.* 28: 86-91 (2016); their work showed 10 wt % FPBA hydrogels offer limited glucose-responsive release of insulin. In this way, exploring whether DiPBA motifs could enable glucose-responsive function at 10 wt % was investigated.
Figure 17B:
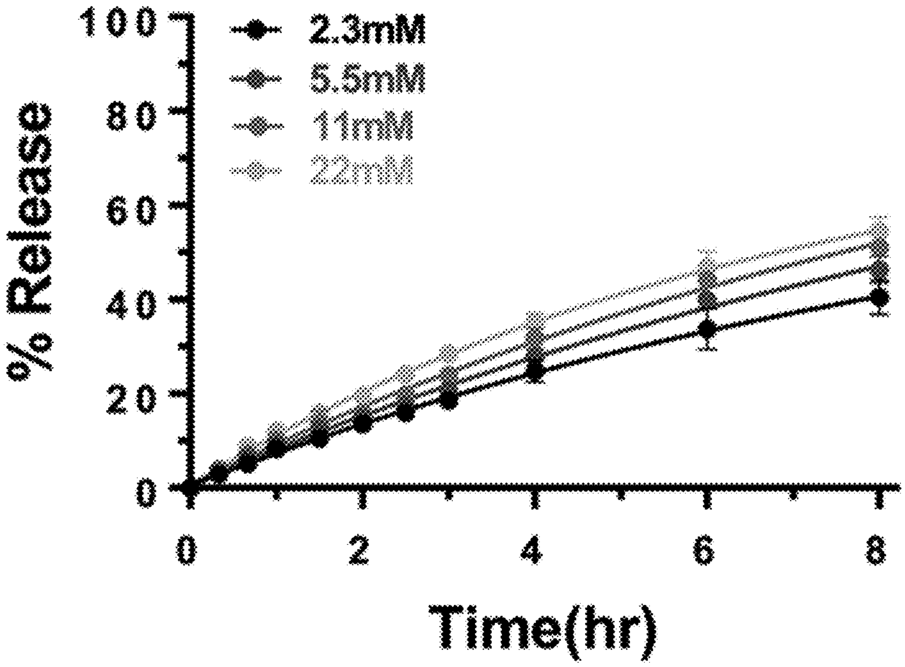
Figure 18A:
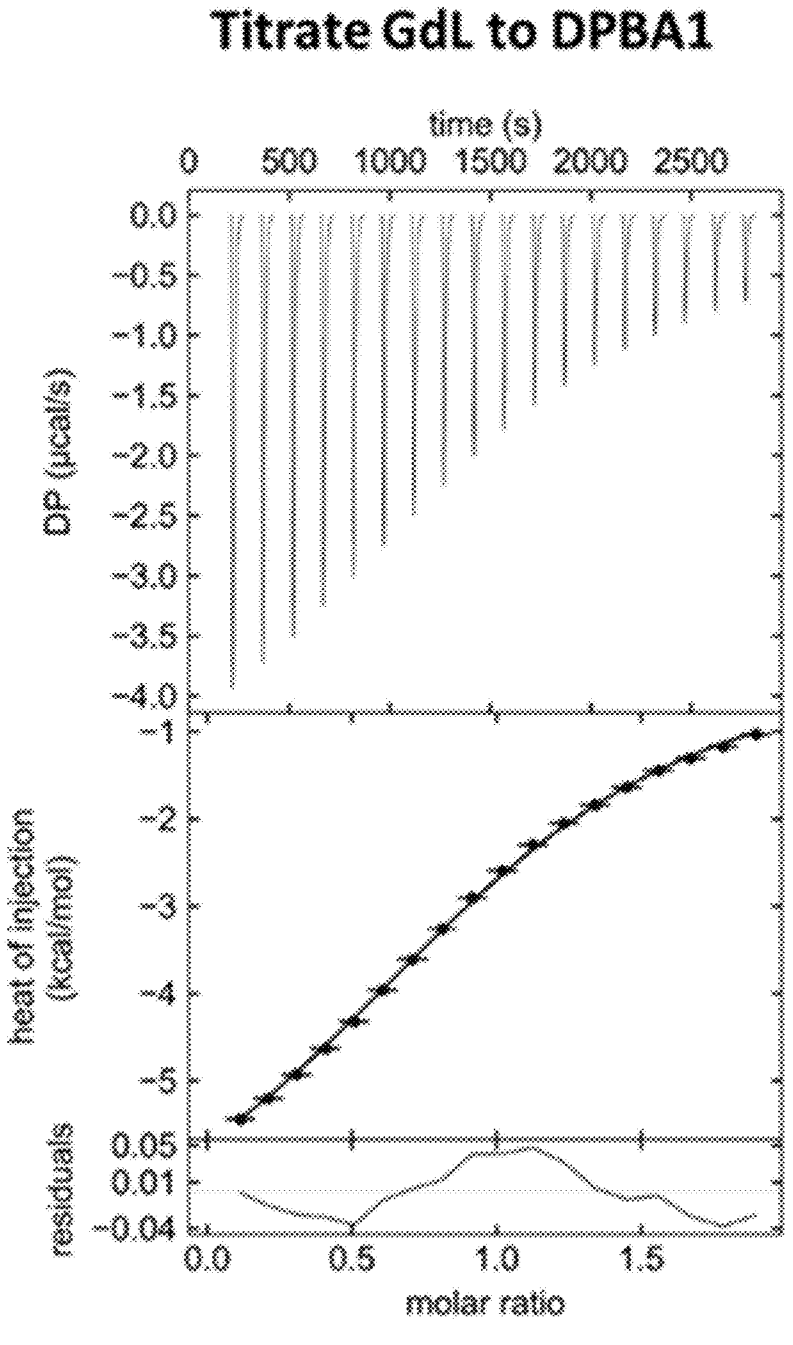
FIG. 18A-B show ITC results comparing interaction of the DiPBA1 small molecule ($DiPBA1_{sm}$) with the GdL-diol (FIG. 18A) or glucose (FIG. 18B).
Figure 18B:
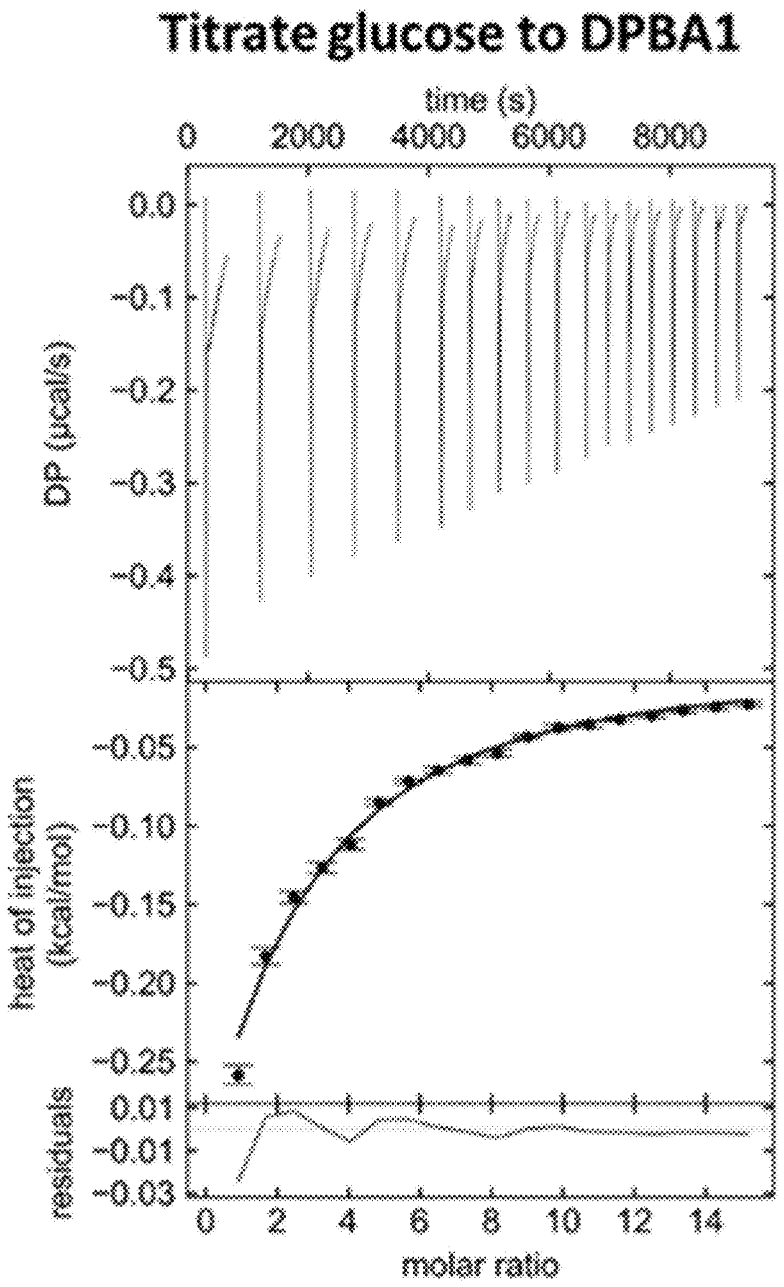
Figure 19A:
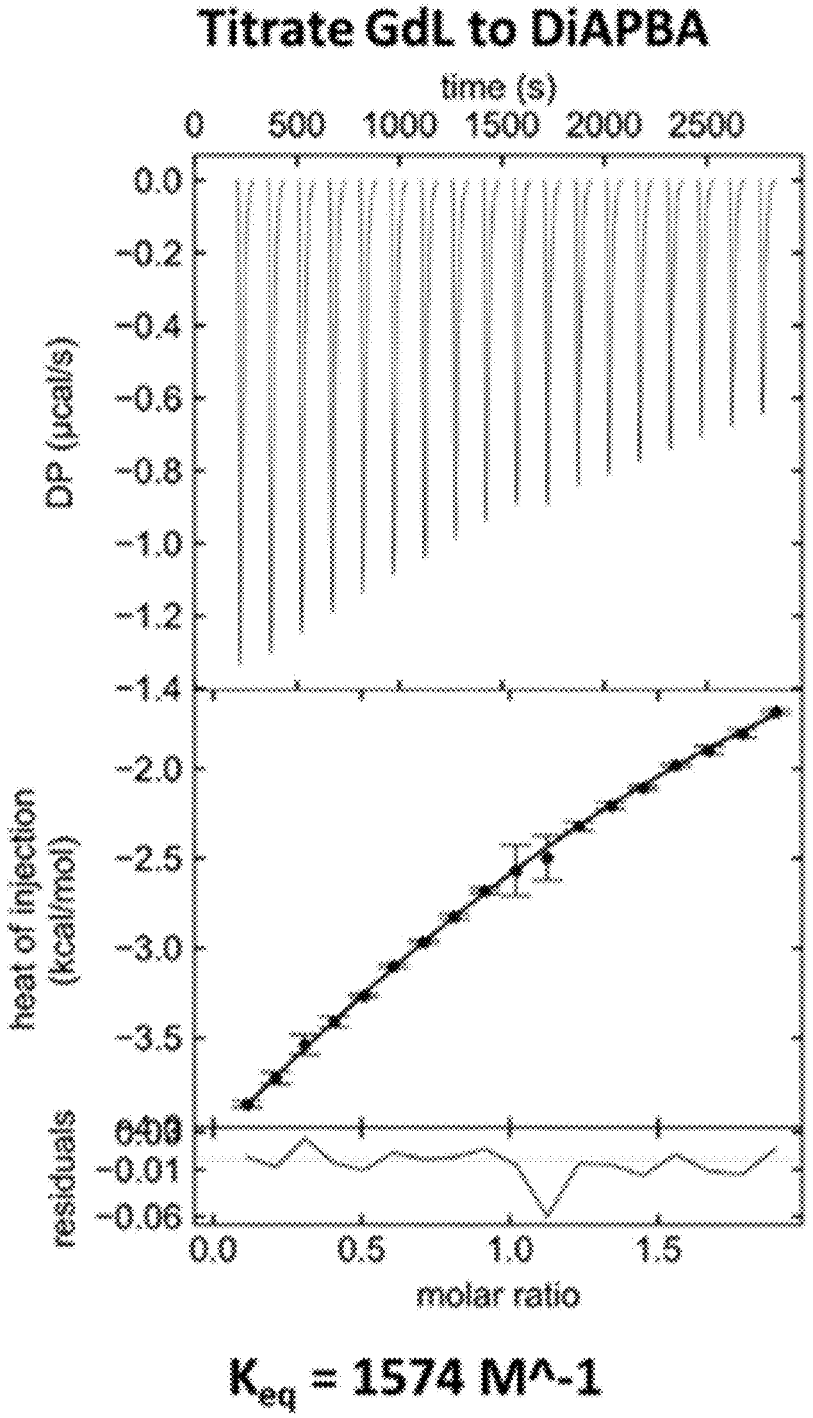
FIG. 19A-B show ITC results comparing interaction of the DiAPBA small molecule ($DiAPBA_{sm}$) with the GdL-diol (FIG. 19A) or glucose (FIG. 19B).
Figure 19B:
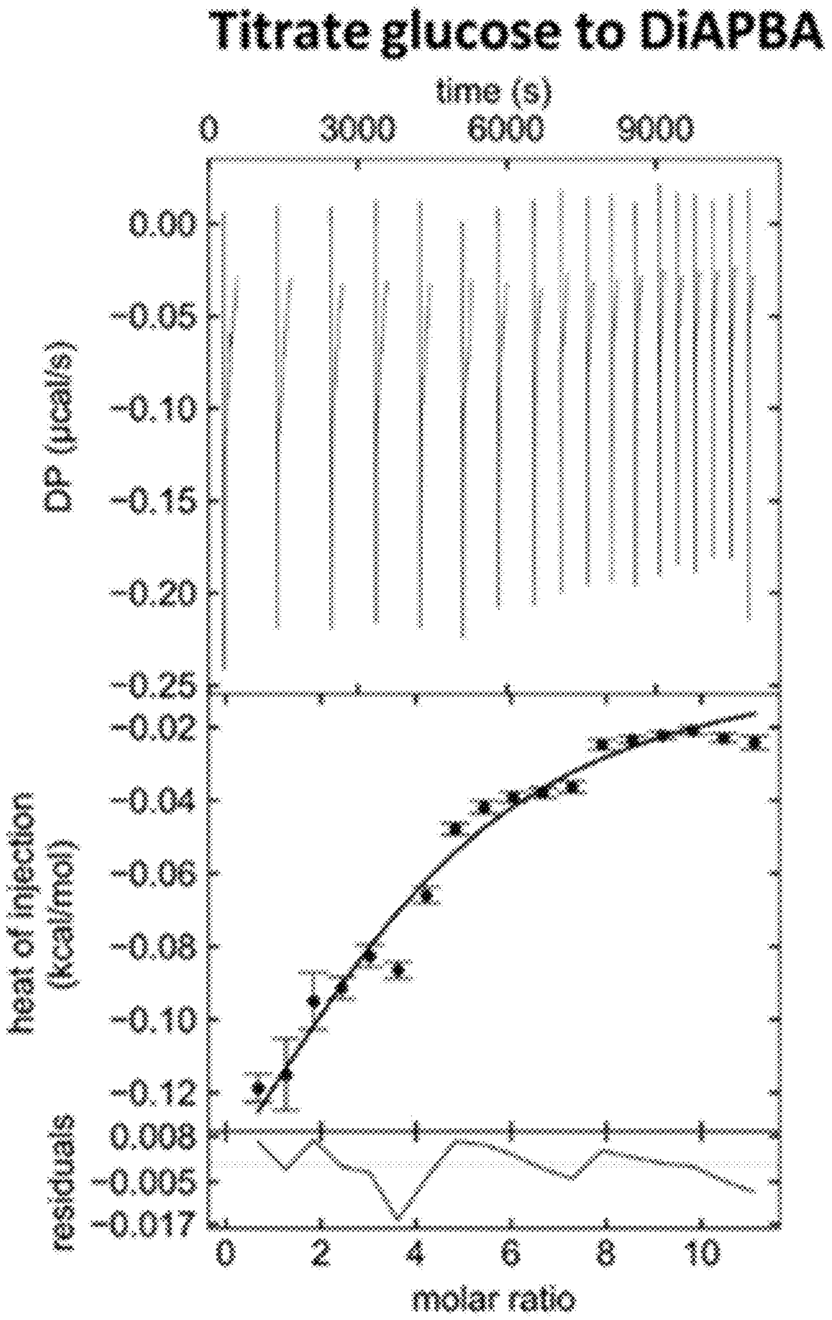
Figure 20A:
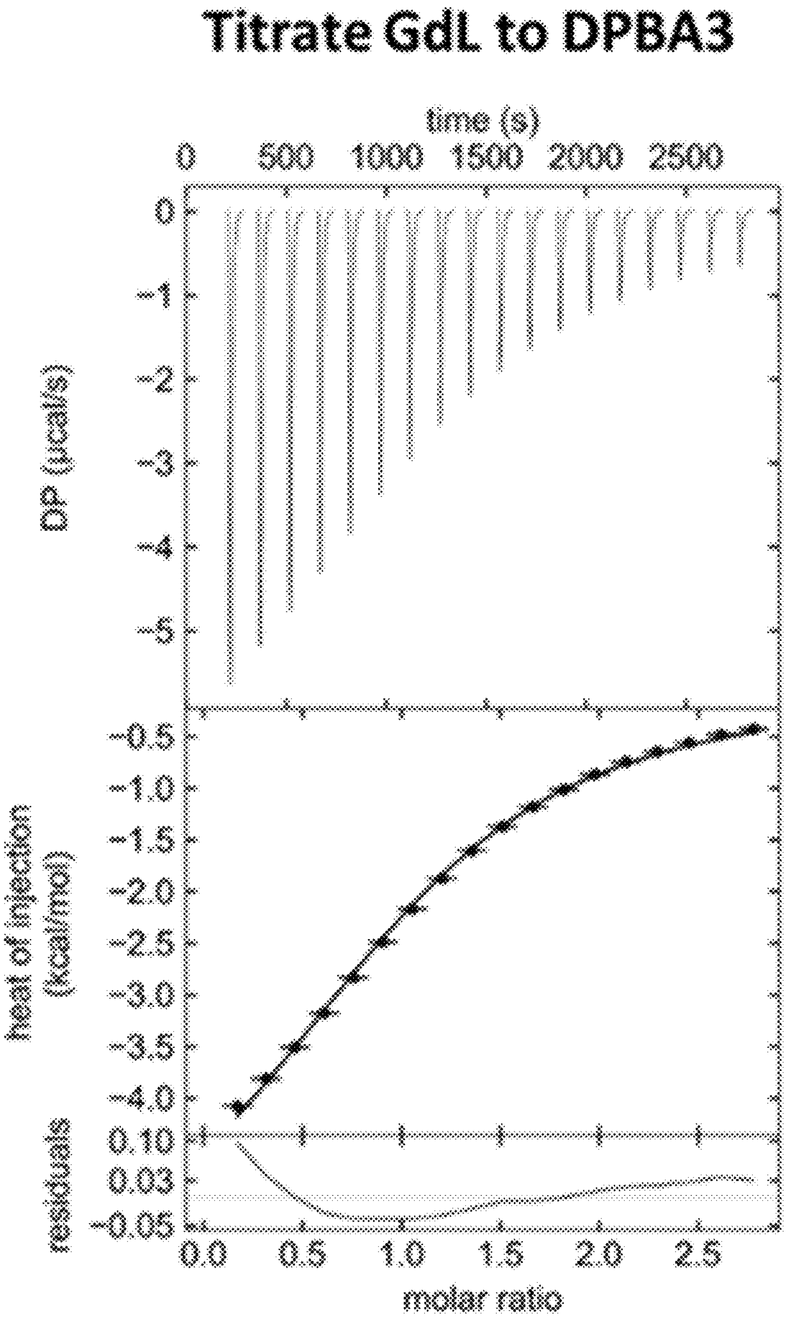
FIG. 20A-C show ITC results comparing interaction of the DiPBA3 small molecule ($DiPBA3_{sm}$) with the GdL-diol (FIG. 20A) or glucose (FIG. 20B), as well as summary of binding for all alternate DiPBA motifs (DiPBA1, DiAPBA, and DiPBA3) to GdL-diol and glucose (FIG. 20C).
Figures 20B, 20C:
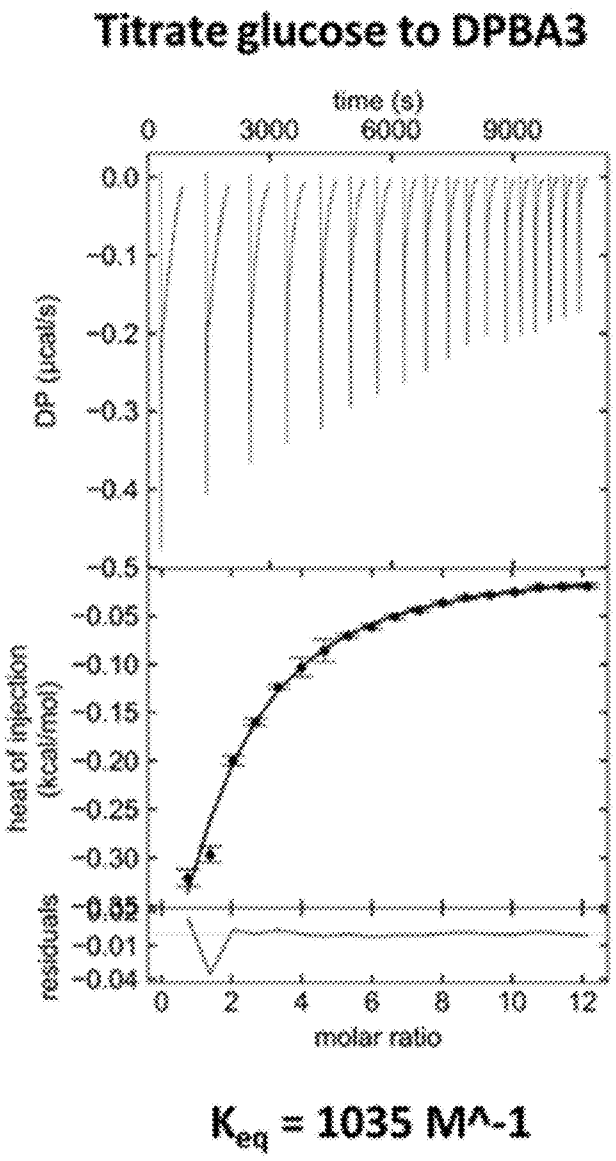
Figure 21A:
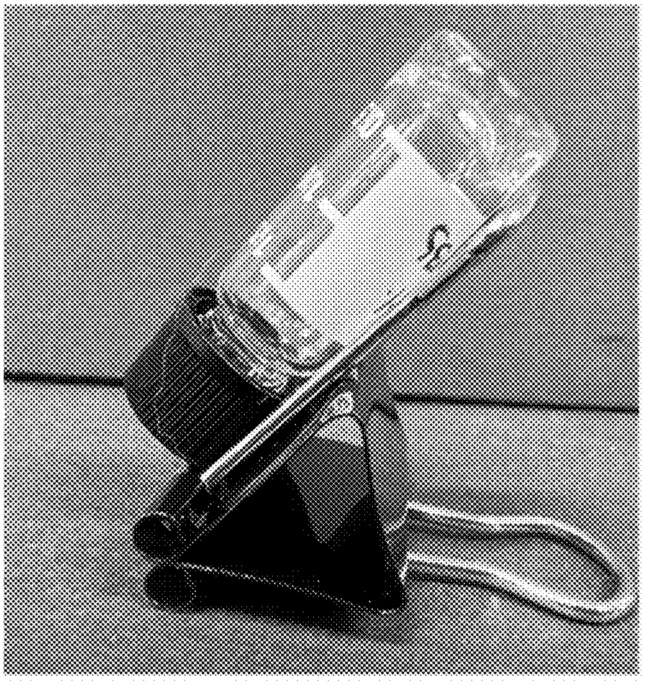
FIG. 21A-B show hydrogels formed between a PAMAM (G6) dendrimer (PAMAM is "Poly(amidoamine) Dendrimer") with 30% of end-groups modified with the DiPBA motif and mixed with 4aPEG-Diol without addition of glucose (FIG. 21A). The same hydrogel formulation with addition of glucose at a concentration of 400 mg/dL (FIG. 21B).
Figure 21B:
Figure 22:
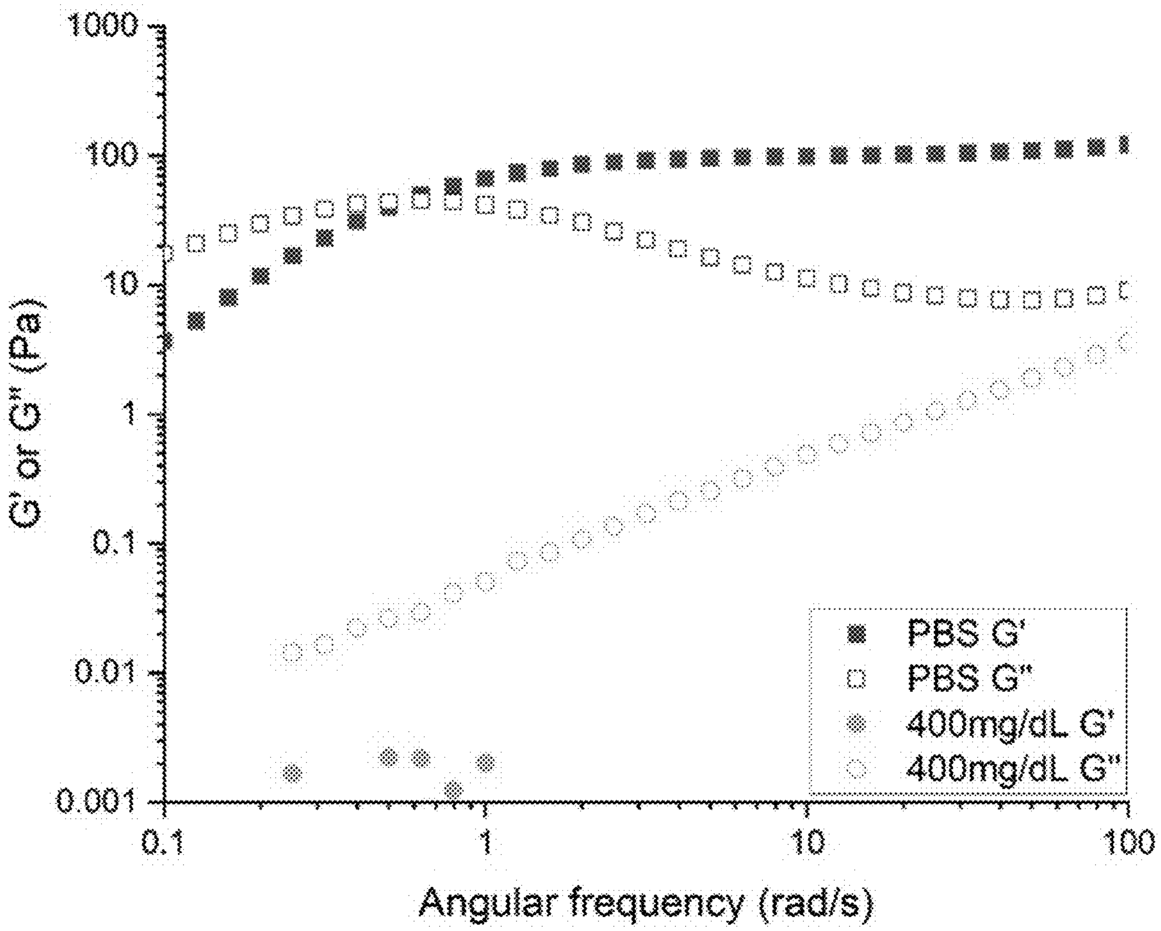
FIG. 22 show rheological frequency sweep for a hydrogel prepared from 4arm-$(PEG)_{10}(Orni)_{32}$ (Orni is "L-Ornithine") mixed with 4aPEG-Diol without glucose (gray squares) or with addition of 400 mg/dL glucose (orange circles).
Figure 23A:
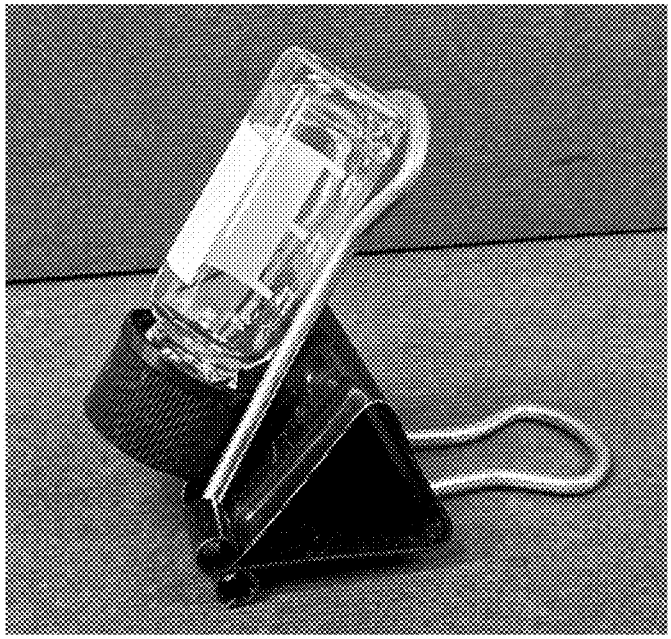
FIG. 23A-B show hydrogels formed between a PAMAM (G2) dendrimer with end-groups modified with the diol motif and mixed with 4aPEG-DiPBA without the addition of glucose (FIG. 23A). The same hydrogel formulation with addition of glucose at a concentration of 400 mg/dL (FIG. 23B).
Figure 23B:
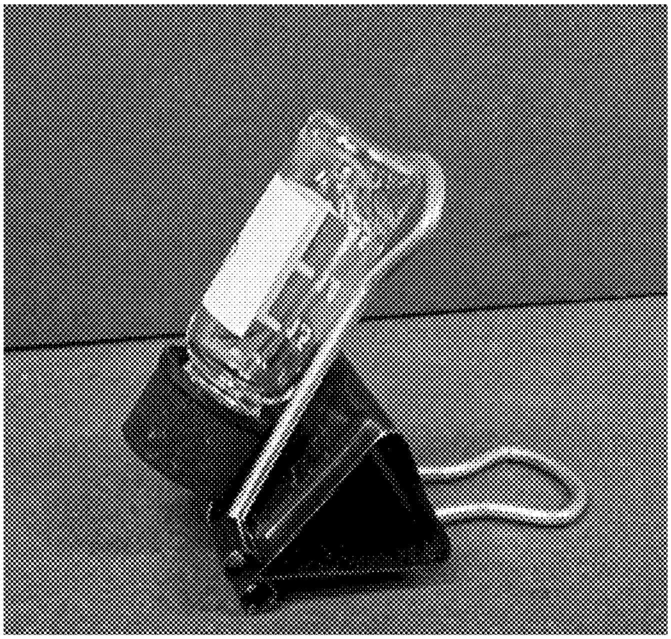
Figure 24A:
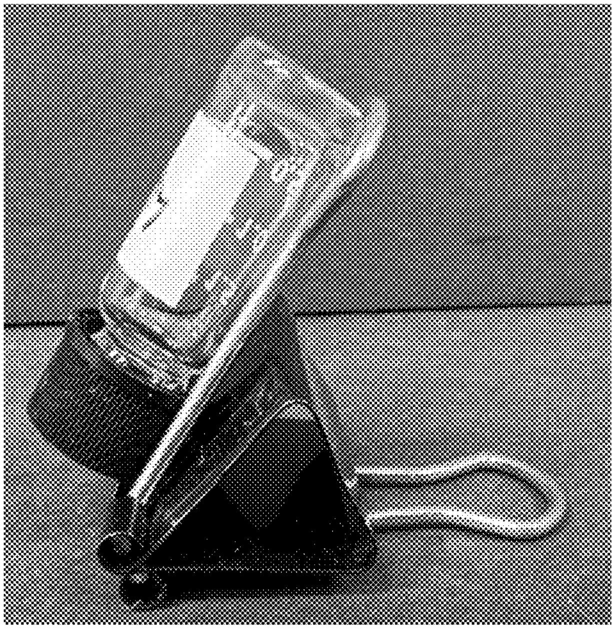
FIG. 24A-B show hydrogels formed between a PAMAM (G6) dendrimer having end-groups modified with the diol motif and mixed with 4aPEG-DiPBA without addition of glucose (FIG. 24A). The same hydrogel formulation with addition of glucose at a concentration of 400 mg/dL (FIG. 24B).
Figure 24B:
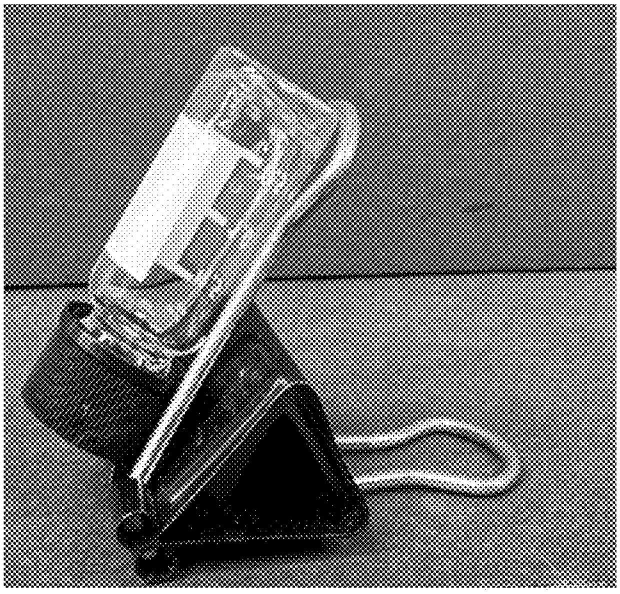
Figure 25:
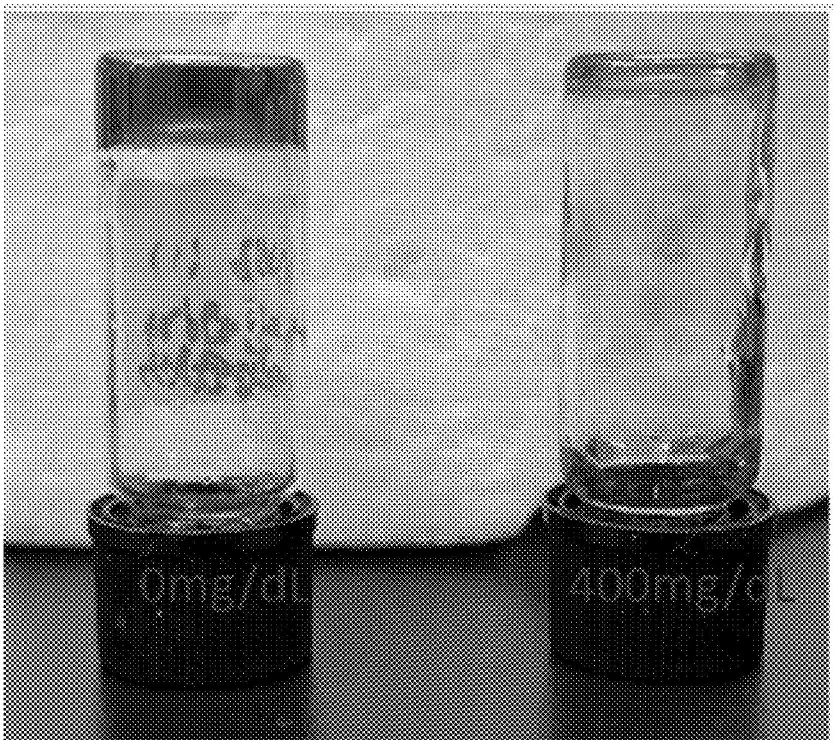
FIG. 25 shows hydrogels formed between 4aPEG-DiPBA and a 4-arm PEG modified with a fructose-like diol with (400 mg/dL) or without (0 mg/dL) the addition of glucose.
Figure 26A:
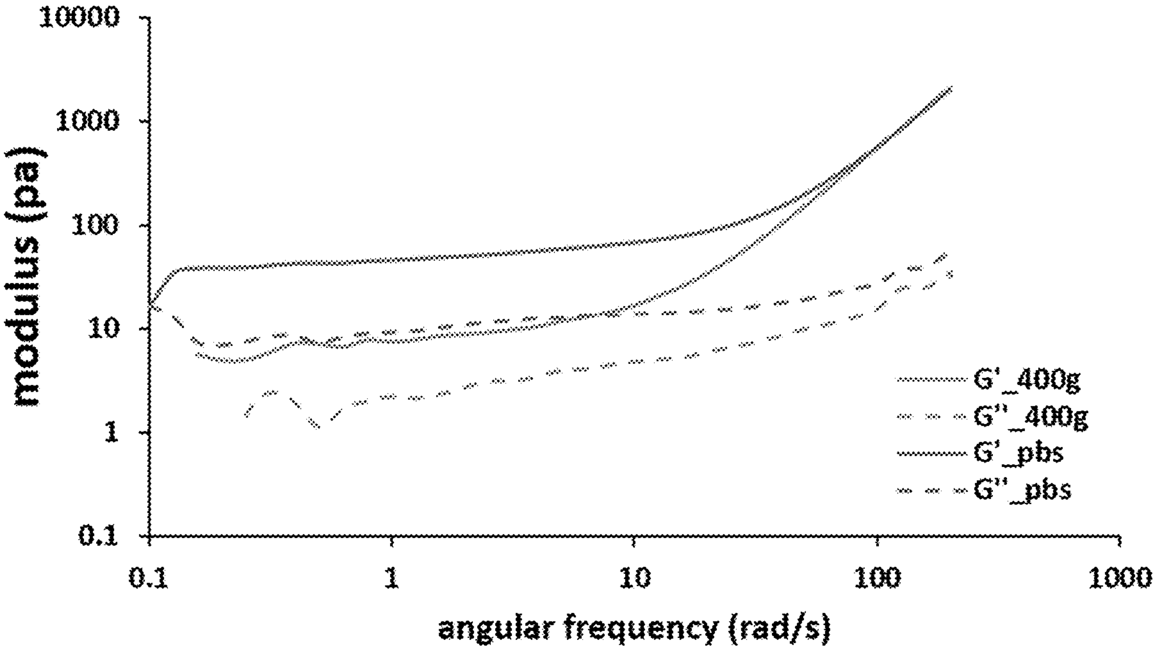
FIG. 26A-B shows rheological frequency sweep data for hydrogels formed between 4aPEG-DiPBA and a 4-arm PEG modified with a fructose-like diol with (400 mg/dL) or without (0 mg/dL) the addition of glucose (FIG. 26A). Rheological strain sweep data for hydrogels formed between 4aPEG-DiPBA and a 4-arm PEG modified with a fructose-like diol with (400 mg/dL) or without (0 mg/dL) the addition of glucose (FIG. 26B).
Figure 26B:
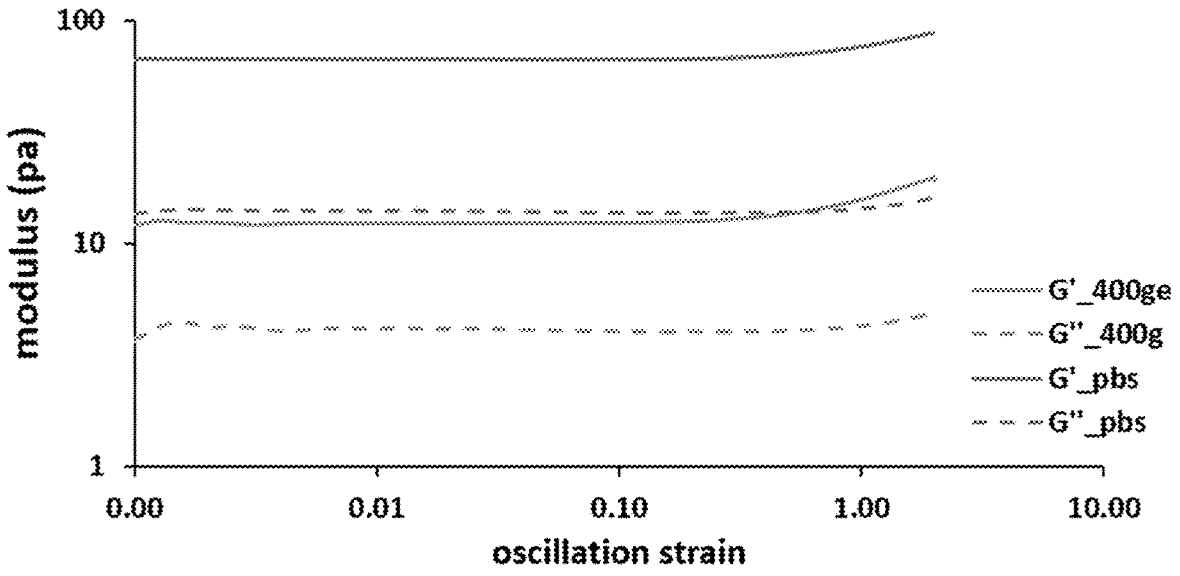

In order to verify therapeutic function of this DiPBA-based hydrogel platform, an in vivo study in streptozotocin-induced diabetic mice was performed (FIG. 11A). This model recreates pathological features of Type-1 diabetes through chemical destruction of pancreatic p-cells, leading to a hyperglycemic and insulin-deficient phenotype. Fasted mice that remained in a state of severe hyperglycemia (>550 mg/dL) were subcutaneously administered DiPBA or FPBA hydrogels with encapsulated insulin, alongside controls of free insulin and saline. Glucose levels were monitored over time using handheld glucometers (FIG. 11B). Treatment with both DiPBA and FPBA hydrogels, as well as that with control insulin, demonstrated blood glucose correction following administration; hydrogels reduced blood glucose to ~60-80 mg/dL and insulin reduced blood glucose to –100 mg/dL. Differences in both the onset and duration of action between the free insulin control and both hydrogels are evident in this early time, with insulin reaching its nadir value at ~1 h and slowly increasing after this time while both hydrogels continued to reduce blood glucose levels to achieve nadir at ~3 h; this corresponds to the expected controlled release of insulin from hydrogels. Saline treatment, meanwhile, demonstrated some blood glucose reduction expected due to continued fasting and recovery from the stimulation of handling and injection. Following administration and blood glucose correction, an intraperitoneal glucose tolerance test (GTT) was performed on all mice. Both hydrogels demonstrated blood glucose recovery approaching their pre-challenge baseline over 3 h, while insulin treated mice had dramatically increased blood glucose without any subsequent correction. This cycle was repeated a second time, where DiPBA and FPBA hydrogels again demonstrated blood glucose correction. Comparing the area under the curve (AUC) following each challenge, the DiPBA hydrogels exhibited significantly improved responsiveness ($P<0.05$) when compared to FPBA hydrogels following both rounds of GTT (FIG. 11C). This effect is especially evident in the second challenge, where AUC values were doubled for FPBA-treated mice compared to DiPBA treatment. The FPBA hydrogels also failed to correct blood glucose back to a normoglycemic range for mice (blood glucose (BG) 5180 mg/dL) within 3 h of the second challenge. The improved control exhibited by DiPBA hydrogels is attributed to its more sensitive and glucose-specific mode of release. At the time of the second challenge, there is less insulin on board hydrogels due to 6 h of prior release. Accordingly, the more rapid responsiveness demonstrated in vitro (FIG. 9D) likely enables increased release of remaining depleted insulin reserve from DiPBA hydrogels in response to the second GTT. It is not possible to place these results in the context of other work on PBA-diol ideal networks, as these prior technologies were not evaluated in a therapeutic capacity in vivo.

Herein, a new DiPBA motif was developed and used for the first time to prepare dynamic-covalent ideal network hydrogels. Molecular-scale binding studies using ITC demonstrated this new DiPBA to have glucose affinity that was 150 times higher than that of a traditional PBA motif. Simultaneously, this DiPBA motif showed reduced binding to fructose and lactate; interference from these non-glucose analytes presents a significant hurdle to the use of PBA-based materials due to the possibility that these physiological analytes may trigger non-specific insulin release. Rheology studies on dynamic-covalent ideal network hydrogels demonstrated DiPBA-diol crosslinking to be more glucose-sensitive than FPBA-diol crosslinking. In addition, hydrogels crosslinked by DiPBA-diol interactions were minimally impacted by non-glucose analytes like fructose and lactate; these analytes were at least as effective as glucose in disrupting crosslinking of FPBA-diol materials. In the context of glucose-responsive insulin delivery for blood glucose management in diabetes, the glucose sensing and specificity of DiPBA-diol crosslinking translated to improved glucose-responsive insulin release from the hydrogels. The improved responsiveness of DiPBA-based crosslinking was further validated in a diabetic mouse model, exhibiting more rapid blood glucose correction following multiple glucose challenges. This approach to use more sensitive and specific DiPBA-diol crosslinking thus offers a new material-centered approach with the potential to achieve the longstanding goal of glucose-responsive insulin therapy, overcoming limitations of commonly used PBA-based crosslinking chemistries.

What is claimed:

1. A hydrogel, the hydrogel comprising:

(i) a diboronate compound of formula (I):

(I)

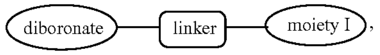

wherein:

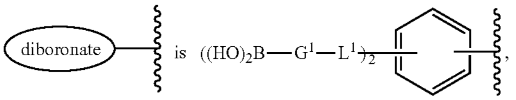

wherein:

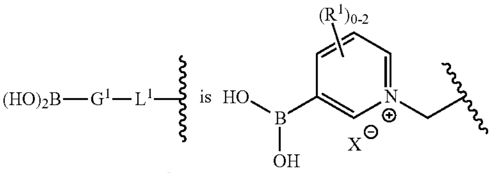

or

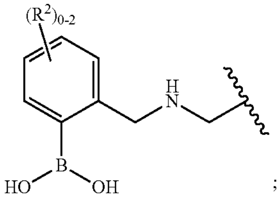

;

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$;

$X^{\ominus}$ is an anion having a net charge of –1;

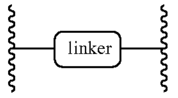

is a linking moiety; and

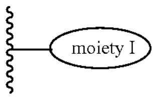

is a first moiety comprising a hydrophilic polymer, a hyperbranched macromolecule, or a combination thereof; and (ii) a diol compound of formula (II):

(II)

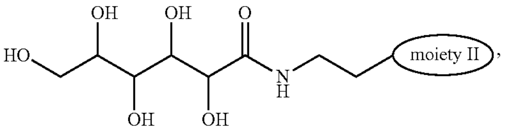

wherein:

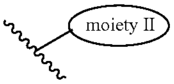

is a second moiety comprising a hydrophilic polymer, a hyperbranched macromolecule, or a combination thereof;

wherein the diboronate compound of formula (I) and the diol compound of formula (II) form crosslinks by dynamic-covalent bonds.

2. The hydrogel of claim 1, wherein

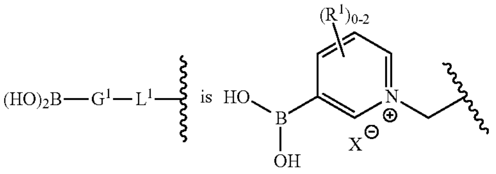

3. The hydrogel of claim 1, wherein

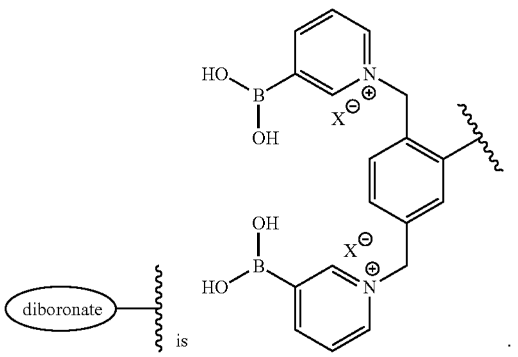

4. The hydrogel of claim 1, wherein $X^{\ominus}$ is $Br^-$, $Cl^-$, $NO_3^-$, $H_2PO_4^-$, $H_2PO_3^-$, $HSO_4^-$, $HSO_3^-$, $H_3C—SO_3^-$, $HCO_3^-$, $HCO_2^-$, $H_3C—CO_2^-$, $HC_2O_4^-$, or $TsO^-$.

5. The hydrogel of claim 1, wherein $X^{\ominus}$ is $Br^-$ or $Cl^-$.

6. The hydrogel of claim 1, wherein

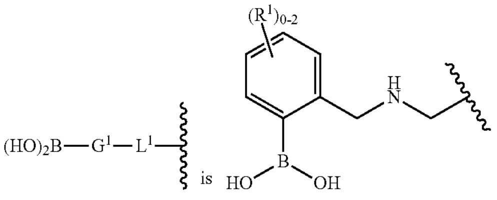

7. The hydrogel of claim 1, wherein

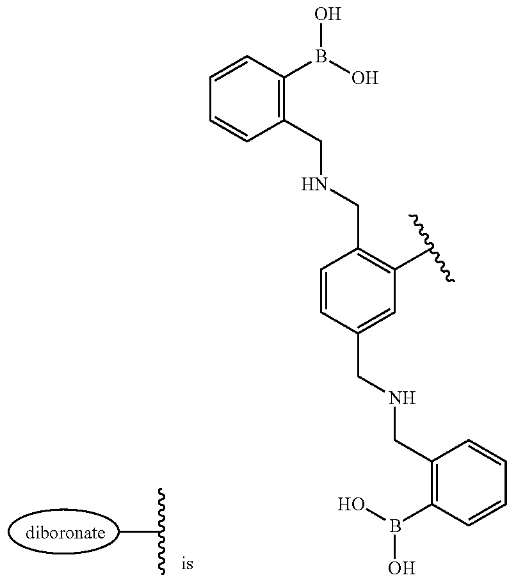

8. The hydrogel of claim 1, wherein

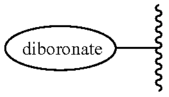

has an equilibrium constant ($K_{eq}$) for binding glucose of at least 350 $M^{-1}$.

9. The hydrogel of claim 1, wherein

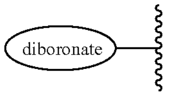

has an equilibrium constant ($K_{eq}$) for binding glucose of at least 1000 $M^{-1}$.

10. The hydrogel of claim 1, wherein

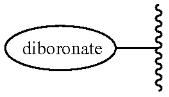

has an equilibrium constant ($K_{eq}$) for binding glucose that is at least 20 times greater than equilibrium constant of

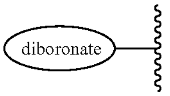

for binding lactate.

11. The hydrogel of claim 1, wherein

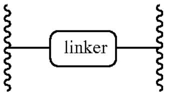

comprises:

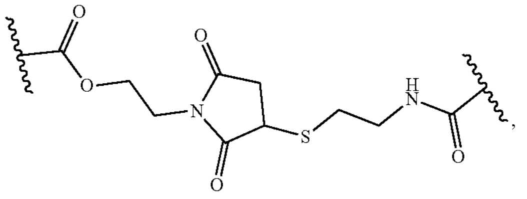

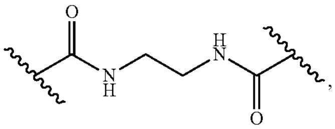

or

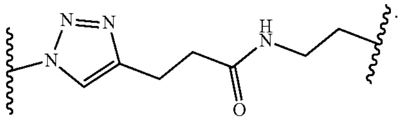

12. The hydrogel of claim 1, wherein

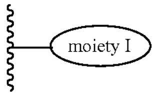

comprises a polyethylene glycol.

13. The hydrogel of claim 12, wherein the diboronate compound of formula (I) comprises:

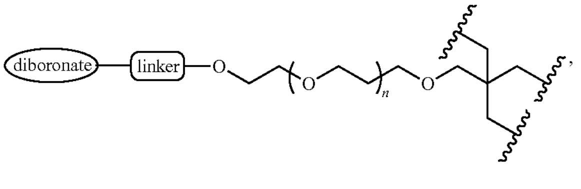

wherein n is 2 to 250.

14. The hydrogel of claim 1, wherein

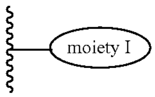

comprises a polyamidoamine dendrimer.

15. The hydrogel of claim 1, wherein

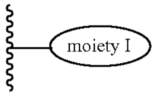

comprises hyaluronic acid.

16. The hydrogel of claim 1, wherein the molar ratio of the diboronate compound of formula (I) to the diol compound of formula (II) is 1:1.

17. The hydrogel of claim 1, wherein

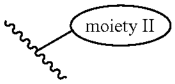

comprises polyethylene glycol.

18. The hydrogel of claim 17, wherein the diol compound of formula (II) comprises:

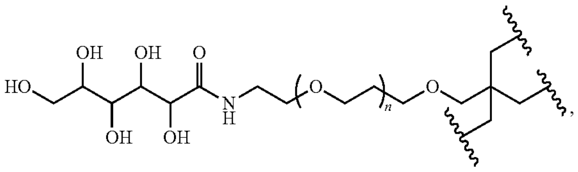

wherein n is 2 to 250.

19. The hydrogel of claim 1, wherein

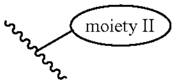

comprises a polyamidoamine dendrimer.

20. A pharmaceutical composition comprising insulin encapsulated within the hydrogel of claim 1.

21. A method of delivering insulin to a subject in need thereof, the method comprising: administering a pharmaceutical composition to a subject in need thereof, the pharmaceutical composition comprising insulin encapsulated within a hydrogel, the hydrogel comprising:

(i) a diboronate compound of formula (I):

(I)

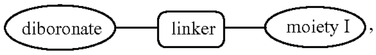

wherein:

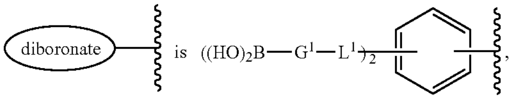

wherein:

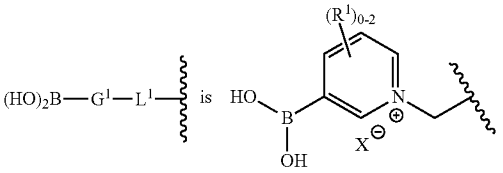

or

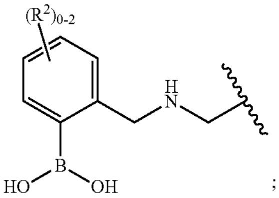

;

$R^1$, at each occurrence, is independently $C_{1-4}$alkyl, cyclopropyl, $C_{1-2}$fluoroalkyl, —F, —CN, or —$NO_2$;

$R^2$, at each occurrence, is independently $C_{1-4}$alkyl, cyclopropyl, $C_{1-2}$fluoroalkyl, —F, —CN, or —$NO_2$; and $X^{\ominus}$ is an anion having a net charge of −1;

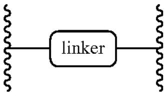

is a linking moiety; and

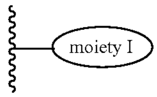

is a first moiety comprising a hydrophilic polymer, a hyperbranched macromolecule, or a combination thereof; and (ii) a diol compound of formula (II):

(II)

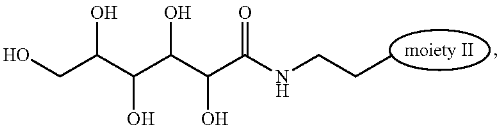

, wherein:

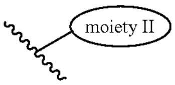

is a second moiety comprising a hydrophilic polymer, a hyperbranched macromolecule, or a combination thereof;

wherein the diboronate compound of formula (I) and the diol compound of formula (II) form crosslinks by dynamic-covalent bonds.

* * * * *